United States Patent
Goldfine et al.

(10) Patent No.: US 6,433,542 B2
(45) Date of Patent: Aug. 13, 2002

(54) APPARATUS AND METHOD FOR OBTAINING INCREASED SENSITIVITY, SELECTIVITY AND DYNAMIC RANGE IN PROPERTY MEASUREMENT USING MAGNETOMETERS

(75) Inventors: Neil J. Goldfine, Newton; James R. Melcher, deceased, late of Lexington, both of MA (US), by Janet D. Melcher, legal representative

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/758,768

(22) Filed: Jan. 11, 2001

Related U.S. Application Data

(62) Division of application No. 09/316,249, filed on May 21, 1999, now Pat. No. 6,252,398, which is a division of application No. 08/854,288, filed on May 9, 1997, now Pat. No. 5,990,677, which is a division of application No. 08/460,664, filed on Jun. 2, 1995, now Pat. No. 5,629,621, which is a division of application No. 07/803,504, filed on Dec. 6, 1991, now Pat. No. 5,453,689.

(51) Int. Cl.[7] .......................... G01R 33/12; G01N 27/72
(52) U.S. Cl. ........................ 324/239; 324/240; 703/4
(58) Field of Search ............... 324/202, 207.17–207.19, 324/225, 227, 229–233, 239–243; 702/38; 703/2–4

(56) References Cited

U.S. PATENT DOCUMENTS

| | | | |
|---|---|---|---|
| 3,249,854 A | 5/1966 | Nevius | 323/108 |
| 3,721,859 A | 3/1973 | Blanyer | 317/5 |
| 3,939,404 A | 2/1976 | Tail | 324/40 |
| 4,058,766 A | 11/1977 | Vogel et al. | 324/61 |
| 4,399,100 A | 8/1983 | Zsolnay et al. | 422/62 |
| 4,423,371 A | 12/1983 | Senturia et al. | 324/61 |
| 4,496,697 A | 1/1985 | Zsolnay et al. | 526/60 |
| 4,757,259 A | 7/1988 | Charpentier | 324/227 |
| 4,799,010 A | 1/1989 | Muller | 324/240 |
| 4,810,966 A | 3/1989 | Schmall | 324/207 |
| 4,814,690 A | 3/1989 | Melcher et al. | 324/61 |

(List continued on next page.)

FOREIGN PATENT DOCUMENTS

| | | |
|---|---|---|
| SU | 502205 | 4/1976 |
| SU | 578609 | 10/1977 |
| SU | 894547 | 12/1981 |
| SU | 1095101 | 5/1984 |

OTHER PUBLICATIONS

Dodd, C.V. and Deeds, W.E., "Absolute Eddy–Current Measurement of Electrical Conductivity," 1981, pp. 387–394. No month.

(List continued on next page.)

*Primary Examiner*—Gerard R. Strecker
(74) *Attorney, Agent, or Firm*—Hamilton, Brook, Smith & Reynolds, P.C.

(57) ABSTRACT

Apparatus and methods are disclosed which provide increased sensitivity, selectivity and dynamic range for non-contact measurement of actual physical and/or kinematic properties of conducting and magnetic materials. The apparatus and methods are based upon various methods for increasing sensitivity, selectivity and dynamic range through proper construction of a magnetometer sensor and for proper selection of operating point parameters for the application. A measurement apparatus for measuring one or more MUT properties includes an electromagnetic winding structure which, when driven by an electric signal, imposes a magnetic field in the MUT and senses an electromagnetic response. An analyzer is provided for applying the electric signal to the winding structure. A property estimator is coupled to the winding structure and translates sensed electromagnetic responses into estimates of one or more preselected properties of the material.

3 Claims, 53 Drawing Sheets

U.S. PATENT DOCUMENTS

| | | | | |
|---|---|---|---|---|
| 4,873,489 | A | 10/1989 | Melcher et al. | 324/453 |
| 4,883,264 | A | 11/1989 | Yoshikawa et al. | 271/110 |
| 4,922,201 | A | 5/1990 | Vernon et al. | 324/236 |
| 5,015,951 | A | 5/1991 | Melcher | 324/232 |
| 5,041,785 | A | 8/1991 | Bogaerts et al. | 324/207.24 |
| 5,059,902 | A | 10/1991 | Linder | 324/207 |
| 5,086,274 | A | 2/1992 | Gobin et al. | 324/239 |
| 5,182,513 | A | 1/1993 | Young et al. | 324/232 |
| 5,223,796 | A | 6/1993 | Waldman et al. | 324/687 |
| 5,237,271 | A | 8/1993 | Hedengren | 324/232 |
| 5,262,722 | A | 11/1993 | Hedengren et al. | 324/242 |
| 5,315,234 | A | 5/1994 | Sutton, Jr. et al. | 324/242 |
| 5,345,514 | A | 9/1994 | Mahdavieh et al. | 382/8 |
| 5,389,876 | A | 2/1995 | Hedengren et al. | 324/242 |
| 5,453,689 | A | 9/1995 | Goldfine et al. | 324/239 |
| 5,621,332 | A | 4/1997 | Inkpen et al. | 324/650 |

OTHER PUBLICATIONS

Dodd, C.V. and Simpson, W.A., "Measurement of Small Magnetic Permeability Changes by Eddy Current Techniques," Oct. 1971, pp. 217–221.

Rose, J.H. And Nair, S.M., "Exact Recovery of the DC Electrical Conductivity of a Layered Solid," 1991, pp. L31–L36. No month.

Krampfner, Yehuda D. and Johnson, Duane D., "Flexible Substrate Eddy Current Coil Arrays," Review of Progress in Quantitative Nondestructive Evaluation, vol. 7A, pp. 471–478 1988. No month.

Goldfine, Neil J. et al., "Dielectrometers and magnetometers, suitable for in–situ inspection of ceramic and metallic coated components," SPIE Conference, Nondestructive Evaluation of Aging Infrastructure, Jun. 1995, 6 pages.

Goldfine, Neil J. et al., "A New Eddy–Current Based Technology For Repeatable Residual Stress and Age Degradation Monitoring," *ASNT International Chemical and Petroleum Industry Inspection Technology IV*, Houston, Texas, Jun. 19–22, 1995, 3 pages.

Zaretsky, M. et al., "Model Approach to Obtaining Continuum Properties From Interdigital Electrode Dielectrometry," Lees Technical Report, TR–86–019, Jul., 1986, pp. 1–43.

Auld, B.A. et al., "Eddy–Current Signal Analysis and Inversion for Semielliptical Surface Cracks," Journal of Nondestructive Evaluation, vol. 7, Nos. 1/2, 1988, pp. 79–94. No month.

*Large Radius Parts*

*Small Radius Parts*

*Spiralled Sensor Construct*

| | MAGNETOMETER PARAMETERS | | | | | | | | |
|---|---|---|---|---|---|---|---|---|---|
| | Geometric (lengths in mm) | | | | | | | | |
| Construct | $\lambda$ | $\Delta$ | $c$ | $d$ | $g$ | $l$ | $m$ | $\sigma$(mhos/m) | $z_l$ | freq |
| original | 12.7 | 0.025 | 1.27 | 0.65 | 0.6 | 100 | 10 | 5.8E7 | $\infty$ | scan |
| (a) | 10.0 | 0.05 | 2.00 | 0.100 | 0.100 | 100 | 10 | 5.8E7 | $\infty$ | scan |

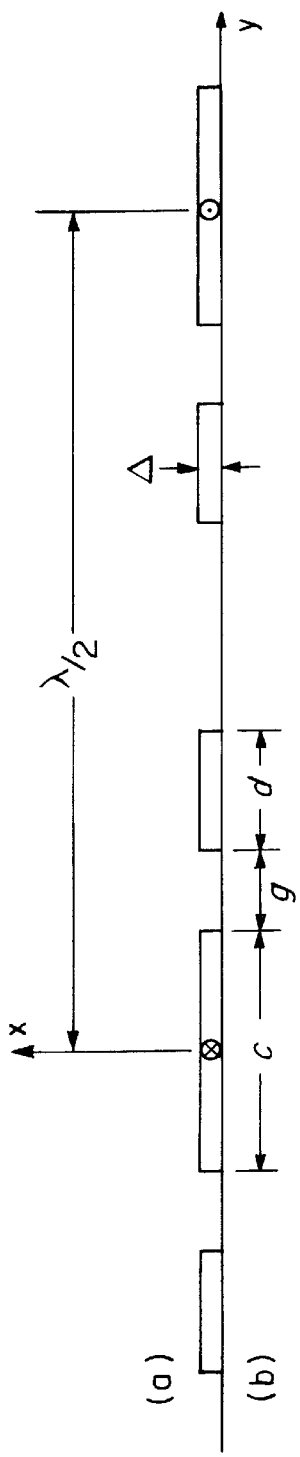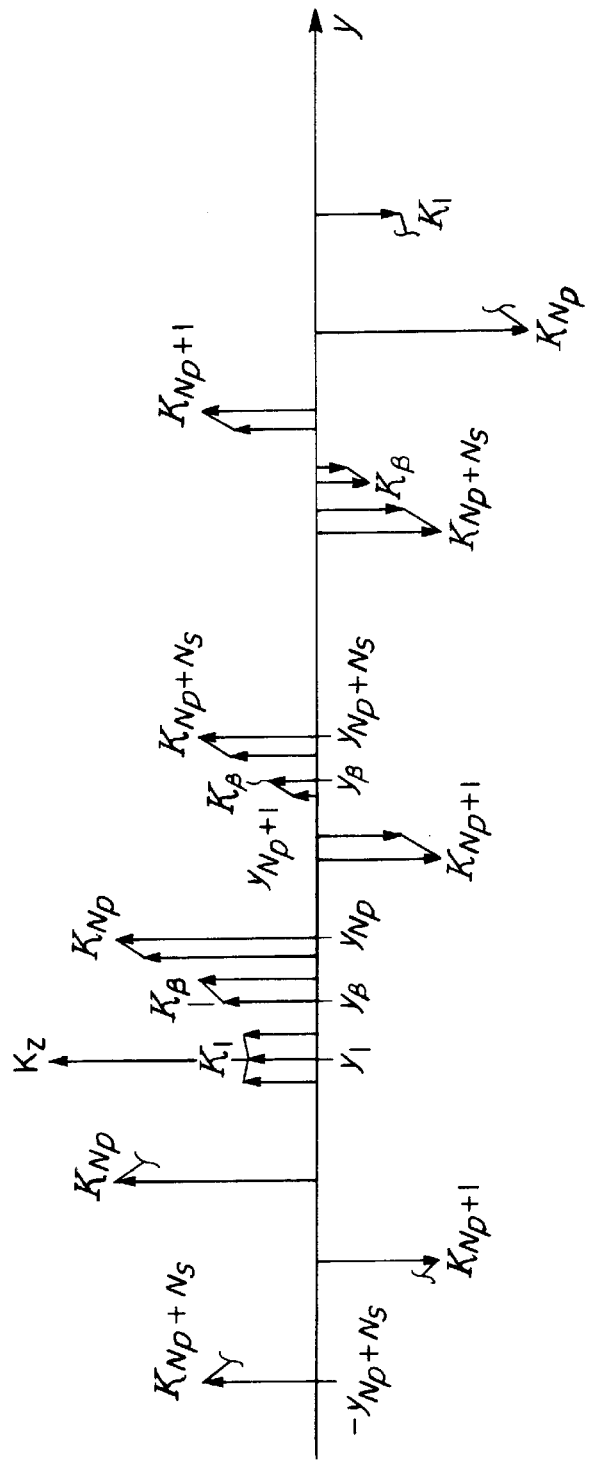
FIG. 24a
FIG. 24b

| log (freq.) | Transinductance $v_2/j\omega i_1$ | | | |
|---|---|---|---|---|
| | magnitude ($\mu\Omega$sec/rad) | | phase (degrees) | |
| | $h_a(3)=0$ | $h_a(3)=0.8$mm | $h_a(3)=0$ | $h_a(3)=0.8$mm |
| 4.4 | 0.374 | 0.393 | -9.9 | -5.4 |
| 4.6 | 0.348 | 0.376 | -11.8 | -6.5 |
| 4.8 | 0.321 | 0.359 | -12.8 | -6.9 |
| 5.0 | 0.296 | 0.342 | -12.6 | -6.8 |
| 5.2 | 0.276 | 0.329 | -12.1 | -6.3 |
| 5.4 | 0.259 | 0.318 | -11.1 | -5.7 |
| 5.6 | 0.244 | 0.310 | -10.1 | -5.0 |
| 5.8 | 0.232 | 0.302 | -8.9 | -4.3 |
| 6.0 | 0.223 | 0.297 | -7.8 | -3.59 |
| 6.2 | 0.216 | 0.293 | -6.71 | -2.95 |
| 6.4 | 0.211 | 0.292 | -5.68 | -2.4 |
| 6.6 | 0.209 | 0.294 | -4.80 | -1.95 |

FIG. 51a

| log (freq.) | Complex Magnetic Susceptibility | |
|---|---|---|
| | $\chi_m^*$ First Guess | $\chi_m^*$ Estimate |
| 4.4 | -.10-j.20 | -.2176-j.2542 |
| 4.6 | -.20-j.20 | -.3242-j.2493 |
| 4.8 | -.25-j.18 | -.4120-j.2232 |
| 5.0 | -.30-j.15 | -.4709-j.1883 |
| 5.2 | -.40-j.10 | -.5245-j.1549 |
| 5.4 | -.55-j.09 | -.5701-j.1227 |
| 5.6 | -.60-j.08 | -.5932-j.1028 |
| 5.8 | -.62-j.06 | -.6164-j.0829 |
| 6.0 | -.64-j.05 | -.6338-j.0673 |
| 6.2 | -.66-j.04 | -.6459-j.0545 |
| 6.4 | -.68-j.03 | -.6543-j.0438 |
| 6.6 | -.70-j.02 | -.6570-j.0356 |

FIG. 51b

APPARATUS AND METHOD FOR OBTAINING INCREASED SENSITIVITY, SELECTIVITY AND DYNAMIC RANGE IN PROPERTY MEASUREMENT USING MAGNETOMETERS

RELATED APPLICATIONS

This application is a Divisional of Application No. 09/316,249 filed on May 21, 1999, now U.S. Pat. No. 6,252,398, which is a Divisional of Application No. 08/854,288, filed on May 9, 1997, now U.S. Pat. No. 5,990,677, which is a Divisional of application Ser. No. 08/460,664, filed on Jun. 2, 1995, now U.S. Pat. No. 5,629,621 which is a Divisional of application Ser. No. 07/803,504, filed on Dec. 6, 1991, now U.S. Pat. No. 5,453,689. The entire teachings of the above applications are incorporated herein by reference.

BACKGROUND OF THE INVENTION

The technical field of this invention is magnetometry and, in particular, the nondestructive electromagnetic interrogation of materials of interest to deduce their physical properties and to measure kinematic properties such as proximity. The disclosed invention applies to both conducting and magnetic media.

Conventional application of magnetometers, specifically eddy current sensors, involves the excitation of a conducting winding, the primary, with an electric current source of prescribed temporal frequency. This produces a time-varying magnetic field at the same frequency. The primary winding is located in close proximity to the material under test (MUT), but not in direct contact with the MUT. This type of nondestructive electro-magnetic interrogation is sometimes called near field measurement. The excitation fields and the relevant spatial and temporal variations of those fields are quasistatic. The magnitude and phase (or the real and imaginary parts) of the impedance measured at the terminals of the primary winding (i.e., the measured voltage at the primary winding terminals divided by the imposed current) or the transimpedance (i.e., the voltage measured at a secondary winding terminals divided by the imposed current in the primary winding) is used to estimate the MUT properties of interest.

The time-varying magnetic field produced by the primary winding induces currents in the MUT that produce their own magnetic fields. These induced fields have a magnetic flux in the opposite direction to the fields produced by the primary. The net result is that conducting MUTs will tend to exclude the magnetic flux produced by the primary windings. The measured impedance and transimpedance at the terminals of the sensor windings is affected by the following: the proximity to the MUT, the physical properties (e.g., permeability and conductivity) of the MUT and the spatial distribution of those properties; the geometric construct of the MUT; other kinematic properties (e.g., velocity) of the MUT; and the existence of defects (e.g., cracks, corrosion, impurities).

The distribution of the currents induced within conducting MUTs and the associated distribution of the magnetic fields in the MUT, in the vicinity of the MUT, and within the conducting primary and secondary windings are governed by the basic laws of physics. Specifically, Ampere's and Faraday's laws combined with Ohm's law and the relevant boundary and continuity conditions result in a mathematical representation of magnetic diffusion in conducting media and the Laplacian decay of magnetic fields. Magnetic diffusion is a phenomena that relates the distribution of induced currents in conducting materials to the distribution of the imposed and induced magnetic fields. Laplacian decay describes the manner in which a magnetic field decays along a path directed away from the original field source.

Magnetometers, such as eddy current sensors, exploit the sensitivity of the impedance or trans-impedance (measured at the sensor winding terminals) to the physical and geometric properties of the MUT. This is sometimes accomplished by using multiple temporal excitation frequencies. As the primary winding excitation frequency is increased, the currents in a conducting MUT exclude more and more flux until all the induced currents in the MUT are confined to a thin layer near the surface of the MUT. At frequencies for which the induced currents are all at the surface of the MUT, the MUT can be represented theoretically as a perfect conductor. In other words, at high enough frequency variations, the conductivity of the MUT will no longer affect the impedance or transimpedance measured at the sensor windings.

This effect has been used in proximity measurement relative to a conducting media. Measurement of proximity to a metal surface is possible at a single excitation frequency, if that frequency is high enough that the MUT can be treated as a perfect conductor. For proximity measurement at lower frequencies, it is necessary to account for the effects of the conductivity of the MUT on the measured impedance, either by physical modeling or by calibration.

In applications requiring the measurement of conductivity, it is necessary to operate at frequencies low enough that the measurements at the terminals of the conducting windings are sensitive to the MUT conductivity. Such applications include the monitoring of aging in conducting media, as well as the direct measurement of conductivity for quality monitoring in metal processing and manufacturing process control. For example, the accurate measurement of the case depth (e.g., the thickness of a heat-affected zone at the surface of a metal after heat treatment) requires a sensor winding geometry and excitation conditions (e.g., frequency, proximity to the MUT) that produce the required sensitivity to the conductivity and thickness of the heat-affected zone.

Two methods are available for determining the desired conditions: (1) experimentation and calibration, and (2) physical modeling and response prediction from basic principals. In practice, each of these techniques has met with some success. The principal limitations of experimentation and calibration are the need for fabrication of expensive calibration test pieces (standards) for each new application, the relatively small dynamic range (i.e., the small range of permissible MUT property variations over which the measurement specifications can be met), and the inaccuracies produced by variation in uncontrolled conditions such as temperature and lift-off errors.

The principal limitations of the physical modeling approach are the inaccuracies introduced by modeling approximations and the existence of unmodeled effects. These limitations are most severe for sensor winding constructs that are not specifically designed to minimize unmodeled effects.

In spite of these limitations, the successful use of conducting windings driven by a current source, as in eddy current sensors, to measure physical and kinematic properties has been widely demonstrated.

For example, eddy current sensors have been used to measure the thickness of conducting strips of known conductivity, as disclosed in Soviet Patents 578,609 and 502,205. Eddy current sensors have also been used for flaw detection, as disclosed in U.S. Pat. No. 3,939,404. Other eddy current sensor applications include measurement of the conductivity-thickness product for thin conducting layers, measurement of the conductivity of conducting plates using calibration standards, and measurement of proximity to conducting layers. Such sensors are also used in proximity measurement for control of machines and devices.

The ability to resolve distributions of parameters and properties of different layers in multi-layered materials has been addressed in U.S. Pat. No. 5,015,951. The referenced patent introduced the concept of multiple wavenumber magnetic interrogations of the material of interest, by imposing several different spatial magnetic field excitations, using multiple preselected sensor winding constructs, each with a different wavelength.

There is a substantial need for enhancements to the measurement performance capabilities of magnetometers. This includes the ability to measure (1) the conductivity and thickness of thin metallic layers independently to improve quality control in deposition and heat treatment processes (in practice, only the product of conductivity and thickness can be measured for thin layers for which the conductivity-thickness product is below a certain threshold); (2) more than one property independently with reliable and predictable performance over a wide dynamic range to provide a more accurate characterization of the MUT; (3) geometric or physical properties over a wide dynamic range without calibration to reduce cost and measurement setup time; (4) material properties such as permeability and conductivity of ferrous metallic layers or conductivity of deposited metallic layers, for quality control and property monitoring after processing (e.g., in situ monitoring of permeability for sheets of transformer core alloy, or conductivity measurement for thin metallic layers of different conductivity that form on metallic surfaces during heat treatment); (5) the thickness of conducting layers or heat affected zones on conducting substrates that do not have conductivities which are significantly different from that of the surface layer, to control heat treatment and monitor MUT properties; (6) the independent measurement of both the conductivity and height (i.e., the distance between the sensor windings and the MUT) of a conducting layer, to accurately account for lift-off affects in applications such as crack detecting (i.e., air gaps between the sensor windings and the MUT surface); and (7) measurement of kinematic properties such as proximity and relative velocity to conducting and magnetic media for actuator and process control.

Furthermore, there is a need for measurement methods that provide estimates of the actual physical properties of the MUT. Current techniques often measure "effective" properties that are only indirectly related to the actual physical properties (e.g., permeability and conductivity at a specified excitation frequency). These "effective property measurements often provide insufficient characterization of the MUT. For example, multiple temporal excitation frequencies are often used to obtain estimates of conductivity or permeability. This is not acceptable if these physical properties vary with temporal excitation frequency. In applications such as monitoring of aging and fatigue in ferrous and nonferrous metal alloys, it may be necessary to completely characterize the dispersive properties of the MUT, including the variations of conductivity and permeability with temporal excitation frequency. Thus, a technique is required that provides accurate estimates of actual physical and geometric properties of the MUT from measurements at a single temporal excitation frequency.

SUMMARY OF THE INVENTION

To overcome the aforementioned limitations in current practice, magnetometers must provide increased sensitivity, selectivity and dynamic range as well as the capability to measure actual MUT properties without calibration when required. Note that sensitivity is defined herein as the incremental change in the transimpedance measured at the sensor terminals in response to an incremental change in the geometric or physical MUT property of interest. Selectivity is defined herein as a measure of the ability to independently estimate two distinct properties (e.g. conductivity and thickness of a thin conducting layer). Dynamic range is defined herein as the range of MUT properties over which sufficient sensitivity and selectivity can be achieved.

In accordance with the present invention, apparatus and methods are disclosed which provide increased sensitivity, selectivity and dynamic range for non-contact measurement of actual physical and/or kinematic properties of conducting and magnetic materials. The disclosed invention is based upon various methods for increasing sensitivity, selectivity and dynamic range through proper construction of the magnetometer sensor and proper selection of operating point parameters for the application under consideration.

In one embodiment, a measurement apparatus for measuring one or more MUT properties includes an electromagnetic winding structure which, when driven by an electric signal, imposes a magnetic field in the MUT and senses an electromagnetic response. An analyzer is provided for applying the electric signal to the winding structure. A property estimator is coupled to the winding structure and translates sensed electromagnetic responses into estimates of one or more preselected properties of the material. In accordance with the present invention, the temporal excitation frequency of the electric signal applied to the winding structure is proximal to a transverse diffusion effect (TDE) characteristic frequency of the winding structure.

The TDE characteristic frequency is defined as the temporal excitation frequency at which the currents within a primary winding of the winding structure transition from a nearly uniform distribution throughout the primary winding cross-section to a distribution in which the currents are confined to a thin layer near the surface of the primary winding. In many applications, the sensitivity of response measurements to specific MUT properties of interest, or the selectivity for two MUT properties of interest, is increased when the frequency of the electric signal is near the TDE characteristic frequency. As such, the TDE-based apparatus is intentionally constructed to amplify the effects of the TDE. To that end, the winding structure comprises an optional permeable substrate and an optional conducting backplane for tuning (i.e., intentionally altering) the TDE characteristic frequency of the winding structure.

The electromagnetic winding structure in the preferred embodiments comprises a plurality of electromagnetic windings forming a meandering pattern. The meandering winding structure is a significant feature of the invention in that its geometry provides physical behavior which may be accurately modeled. As such, the magnetometer is capable of accurately estimating preselected material properties based on sensed responses obtained by the meandering winding structure.

A TDE-based apparatus may further comprise a model which is successively implemented by the property estimator for generating a property estimation grid which translates sensed electromagnetic responses into estimates of preselected MUT properties. The model provides for each implementation a prediction of electromagnetic response for the preselected properties based on a set of properties characterizing the winding structure and the MUT. The model is described in more detail below in accordance with a method for generating a property estimation grid.

A TDE-based magnetometer may be manipulated to obtain multiple responses for various operating conditions. For example, sensed responses may be obtained by the winding structure at multiple proximities to the MUT and converted to material property estimates. In another example, sensed responses may be obtained by the winding structure for a plurality of positions along a surface of the MUT. Further, for each position relative to the MUT the winding structure may be adjusted to obtain sensed responses for various proximities and orientations relative to the MUT. In yet another example, the magnetometer winding structure may be capable of being adapted to conform to a curved surface of the MUT for obtaining sensed responses and providing estimates of MUT properties. In another example, the frequency of the electric signal may be varied for obtaining a plurality of frequency related sensed responses with the winding structure.

A TDE-based magnetometer may be employed in a plurality of specific applications to provide substantially independent estimates of specified properties of interest. To that end, a TDE-based magnetometer is capable of providing independent estimates of each of a pair of properties at a single temporal excitation frequency from a single sensed response. This enables the TDS-based magnetometer to obtain estimates of dispersive properties of single and multiple layered MUTs. Potential pairs of MUT properties include (1) conductivity and thickness, (2) conductivity and proximity, (3) conductivity and permeability, (4) thickness and permeability, (5) permeability and proximity and (7) the real and imaginary parts of the complex permeability. The MUT property estimates may then be processed to estimate other MUT properties such as aging/fatigue, bulk and surface crack location and heat affected zone properties.

In other preferred embodiments, it is desirable to shift the TDE characteristic frequency away from the characteristic transition frequency associated with magnetic diffusion in the MUT in order to measure preselected MUT properties with required levels of sensitivity, selectivity and dynamic range. This is accomplished by changing the physical and geometric properties of the magnetometer.

In one embodiment in which the TDE characteristic frequency may or may not be significant, a magnetometer has a winding structure comprising a primary winding capable of imposing a magnetic field in the MUT when driven by an electric signal. The winding structure also includes one or more secondary windings for sensing electromagnetic responses. In this winding structure, the primary winding has a width which is substantially greater than the width of the gap between the primary and secondary windings. Further, the width of the primary winding may also be substantially larger than the thickness of the primary. The winding structure of this embodiment preferably forms a meandering pattern. An analyzer is provided for applying an electric signal to the primary for imposing the magnetic field in the MUT, and a property estimator translates sensed responses into estimates of preselected MUT properties. Preferably, the magnetometer employs a model which is implemented by the property estimator for generating a response prediction table which translates sensed electromagnetic responses into estimates of the preselected MUT properties.

As in the other embodiments, the magnetometer may be used to obtain multiple responses for a plurality of operating conditions. To that end, in one example the magnetometer winding structure may be capable of being adapted to conform to a curved surface of the MUT for obtaining sensed responses and providing estimates of MUT properties. In another example, the winding structure may be adjusted to obtain sensed responses at multiple proximities to the MUT. In yet another example, a magnetometer with a winding structure comprising a single primary and single secondary may be employed for estimating dispersive properties of an MUT with responses obtained at a single temporal excitation frequency and for single or multiple proximities to the MUT. In yet another example, the winding structure may be adjusted to obtain sensed responses for a plurality of positions along a surface of the MUT. Further, for each position the winding structure may be adjusted to obtain sensed responses for multiple proximities and orientations relative to the MUT. In another example, the frequency of the electric signal applied to the winding structure may be varied for each sensed response.

Devices which are constructed to incorporate both magnetoquasistatic (MQS) inductive coupling terms and electroquasistatic (EQS) capacitive coupling terms are referred to as M.S./EQS devices. These devices have applications for materials having properties of interest which are out of the dynamic range of existing M.S. magnetometers and EQS dielectrometers. The introduction of capacitive coupling corrections permits the extension of the dynamic range for MUT properties of interest by allowing responses to be obtained at temporal excitation frequencies at which capacitive coupling is significant in order to increase sensitivity to the MUT properties of interest.

Accordingly, in another embodiment of the invention, an M.S./EQS device provides estimates of distributed properties of a layered MUT. The M.S./EQS device includes an electromagnetic winding structure capable of imposing a magnetic field and an electric field in the MUT when driven by an electric signal and sensing electromagnetic and electric responses. The winding structure comprises a primary winding, a plurality of coplanar first secondary windings and an optional second secondary winding positioned in a different plane. An analyzer provides electric signals to the winding structure and a property estimator translates sensed responses into estimates of preselected properties of the MUT.

Depending on the application, the M.S./EQS device may be operated in an M.S. mode and/or an M.S./EQS mode and/or an EQS mode. Accordingly, when the input current temporal excitation frequency is within the M.S. range for the device, the input current is applied to the primary winding for imposing a magnetic field in the MUT. Sensed electromagnetic responses are obtained at the first secondary windings for each layer of the MUT. When the input current temporal excitation frequency is within the M.S. range and an input voltage temporal excitation frequency is within an EQS range, the input current is applied to the primary to impose a magnetic field and the input voltage is applied to the first secondary windings in a push-pull sense to impose an electric field in the MUT. Sensed electromagnetic responses are obtained at the second secondary winding for each layer of the MUT. When the input current temporal excitation frequency is within the EQS range, the input voltage is applied to the first secondary windings to impose an electric field in the material. Sensed electric responses are obtained at the primary winding for each layer of the MUT. The property analyzer is employed for translating the sensed responses into estimates of preselected distributed properties of each layer of the layered MUT.

The present invention also comprises a method for generating property estimates of one or more preselected properties of an MUT. Accordingly, an electromagnetic structure, an analyzer and a property estimator are provided. The first step in the method requires defining dynamic range and property estimate tolerance requirements for the preselected properties of the material. Next, a winding geometry and configuration is selected for the electromagnetic structure. A continuum model is used for generating property estimation grids for the preselected material properties as well as operating point response curves for preselected operating point parameters.

The grids and curves are subsequently analyzed to define a measurement strategy. Next, operating point parameters and a winding geometry and configuration are determined to meet the dynamic range and tolerance requirements. To accomplish this, property estimation grids and operating point response curves are generated and analyzed for various operating points. Next, sensed electro-magnetic responses are obtained at each operating point and converted by the property estimator into estimates of the preselected material properties. Property estimate tolerances are then estimated as a function of values of the estimated preselected properties over the defined dynamic range using the property estimation grids and operating point response curves. If the property estimate tolerance requirements are not achieved, the process is repeated for different operating point parameters and winding dimensions.

As stated previously, the property estimator implements a model for generating a property estimation grid which translates sensed responses into preselected material property estimates. Accordingly, the present invention includes a method for generating a property estimation grid for use with a magnetometer for estimating preselected properties of a MUT. The first step in generating a grid is defining physical and geometric properties for a MUT including the preselected properties of the MUT. Next, operating point parameters and a winding geometry and winding configuration for the magnetometer are defined.

The MUT properties, the operating point parameters and the magnetometer winding geometry and configuration are input into a model to compute an input/output terminal relation value. Preferably, the input/output terminal relation is a value of transimpedance magnitude and phase. The terminal relation value is then recorded and the process is repeated after incrementing the preselected properties of the MUT. After a number of iterations, the terminal relation values are plotted to form a property estimation grid.

The present invention also includes a method of selection of a magnetometer winding structure and operating point for measuring one or more preselected properties of an MUT which achieves specified property estimate requirements. The first step includes defining physical and geometric properties for the MUT including preselected properties of the MUT. Next, the magnetometer operating point parameters, winding geometry and winding configuration are defined.

The MUT properties and the magnometer operating point parameters, winding geometry and configuration are then input into a model for computing an input/output terminal relation value. The preselected properties of the material are then adjusted to compute another terminal relation value. Using the terminal relation values, Jacobian elements are computed. Note each Jacobian element is a measure of the variation in a terminal relation value due to the variation in a preselected material property.

Next, a singular value decomposition is applied to the Jacobian to obtain singular values, singular vectors and the condition number of said Jacobian. An evaluation is then made of the sensitivity, selectivity and dynamic range of the magnetometer winding structure and operating point parameters using the singular values, singular vectors and condition number. If the material property estimate requirements are not met, the process is repeated with adjusted magnetometer operating point parameters, and winding geometry and configuration until the material property estimate requirements are achieved.

BRIEF DESCRIPTION OF THE DRAWINGS

FIG. 24a is a cross-sectional view of one half wavelength of the Inter-Meander Magnetometer and FIG. 24b is a schematic representation of the collocation surface current density approach used in the continuum model.

FIG. 51a is a table of experimental data using the Inter-Meander Magnetometer prototype with the original geometry for measurements on a granular aluminum layer at 0 and 0.8 mm above the winding plane, and FIG. 51b is the first guess and estimated values of the complex magnetic susceptibility estimated using the experimental data for the layer immediately above the winding plane.

DETAILED DESCRIPTION OF THE INVENTION

Figure 1:
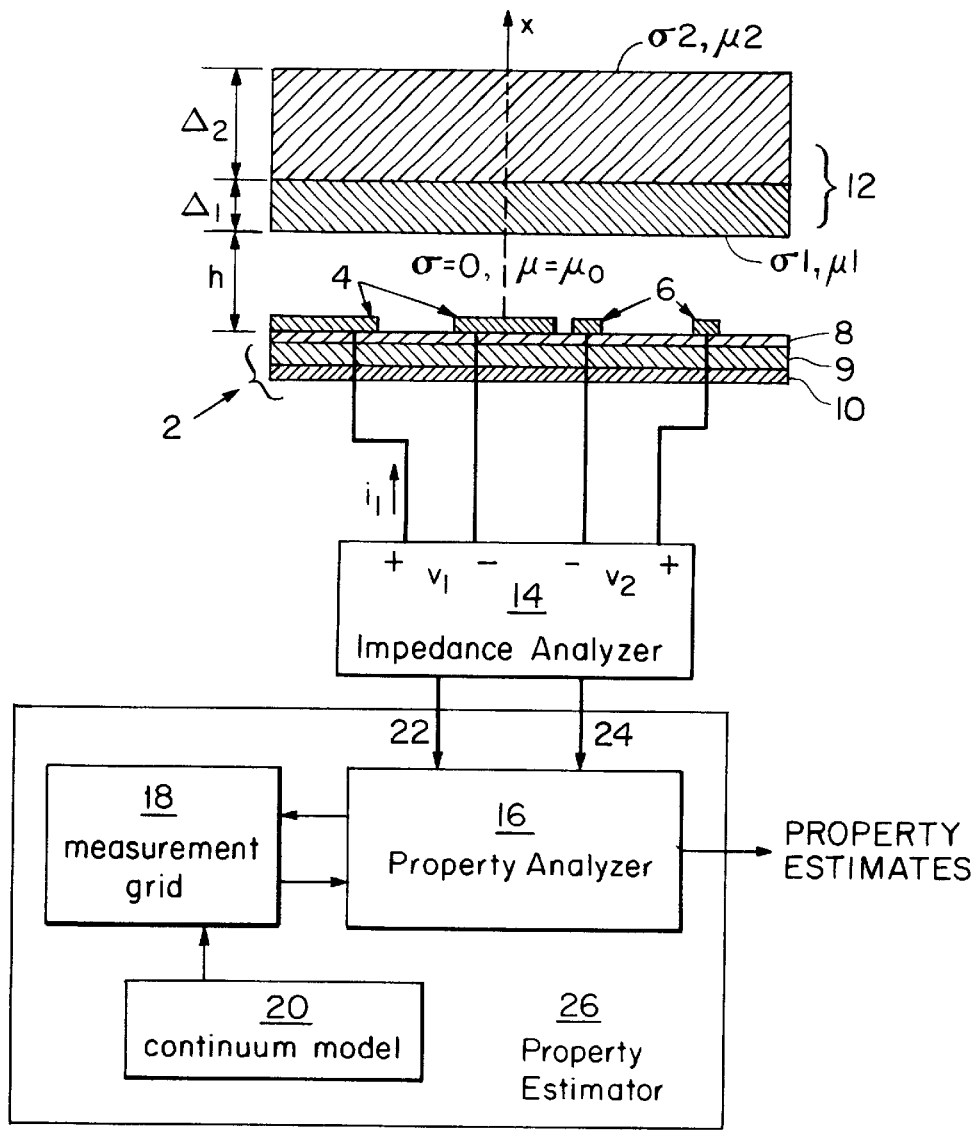
FIG. 1 is an overall schematic diagram of an apparatus for measuring the physical and kinematic properties of a material under test according to the present invention.

Apparatus, devices, methods, and techniques are disclosed for non-contact measurement of physical and kinematic properties of a Material Under Test (MUT). The disclosed measurement apparatus is depicted in FIG. 1. The measurement apparatus includes an electromagnetic element 2 comprised of a primary winding 4, secondary winding 6, an insulating substrate 8, an optional highly permeable substrate 9, and an optional conducting backplane 10. The primary winding 4 (also called the driven winding) is driven by an input current or voltage source at a temporal excitation frequency, f, measured in cycles per second where $f = \omega/2\pi$ and $\omega$ is the angular frequency of the input electric signal, measured in radians per second. The voltage induced at the terminals of the secondary winding 6 (also called the sensing winding) divided by the current applied to the primary winding 4 is called the transimpedance (or transfer impedance). The transimpedance is measured by an impedance analyzer 14. The magnitude 22 and phase 24 of the transimpedance are inputs to a property estimator 26 which uses a measurement grid 18 to estimate pre-selected properties of a single or multiple layered MUT 12. The measurement grid can be generated either with a continuum model 20 or through experimental measurements on calibration test pieces. The model, measurement grid(s), and property analyzer are part of a property estimator 26 that converts measurements at the sensor terminals for single or multiple operating points (e.g., multiple temporal excitation frequencies) to estimates of pre-selected MUT properties of interest.

The disclosed invention is founded upon the ability to increase sensitivity, selectivity, and dynamic range through proper design of the electro-magnetic element 2 and methods for proper selection of operating point(s) parameters. In many cases, the disclosed invention is the enabling component of measurement systems for MUT properties of interest that are not measurable with alternative winding designs (e.g., independent non-invasive measurement of conductivity and thickness for thin conducting films on conducting or insulating substrates).

The Transverse Diffusion Effect Sensitivity (TDES)

A principal feature of the disclosed invention is a phenomenon hereinafter referred to as the Transverse Diffusion Effect Sensitivity (TDES). The key factors in the design of TDES-based sensors are (1) the distribution of the currents within the conducting windings of the sensor construct (i.e., the spatial variation of the current density, J, within the conducting windings in the direction transverse, perpendicular, to the direction of the imposed current flow; this distribution is also called the primary winding transverse-current distribution), (2) the sensitivity of this distribution to the properties of the MUT, (3) the selectivity (i.e., the ability to independently measure two or more MUT properties of interest), and (4) the dynamic range for the pre-selected MUT properties of interest, over which high sensitivity and selectivity can be achieved.

Design methods for conventional eddy current sensors assume the current density within the sensor windings is either uniformly distributed, or confined to a thin layer along the winding surface, and that variations in the transverse-current-distribution has no significant effect on the measurements at the terminals of the sensor windings. A TDES-based sensor is intentionally designed to amplify the effects of the transverse-current-distribution on the measurements at the terminals of the primary and secondary windings.

This is accomplished by introducing cross-sectional shape to the primary and secondary windings. The dependence of the transverse-current-distribution in the primary on the MUT properties of interest provides increased sensitivity, selectivity, and dynamic range for property estimation in many applications of interest. However, measurements at the terminals of the primary and secondary windings will not be sensitive to the primary winding transverse-current-distribution, unless the windings are properly designed to provide increasing inductive coupling to the secondary as the currents crowd-out closer and closer to the primary winding surface in the direction transverse to the direction of the imposed current flow (i.e., as the current density distribution transitions from a uniform distribution at low temporal excitation frequencies to a distribution with the currents confined to a thin layer at the surface of the conducting windings at high temporal excitation frequencies).

Increased sensitivity, selectivity, and dynamic range can be achieved for many common applications of conventional eddy current sensors and other magnetometers by amplifying these effects and by increasing the sensitivity of the transverse-current-distribution within the windings to the MUT properties of interest. The sensitivity of measurement at the terminals of the windings to this distribution is primarily controlled by the winding geometry and dimensions. The sensitivity of this transverse-current-distribution to the MUT properties of interest is controlled by the physical, geometric, and dimensional properties of the winding construct (e.g., winding dimensions, sensor substrate permeability, winding conductivity, and back-plane conductivity and proximity to the windings) as well as the MUT physical, geometric and dimensional properties.

One specific embodiment is shown in FIG. 2c. In this winding construct, the winding geometry is designed so that the width c of the primary 4, is larger than the gap g between the primary 4 and the secondary 6. In the embodiment of FIG. 2c, the thickness, $\Delta$, of the deposited conducting winding material 28 is small compared to the widths, c and d, of the primary and secondary conducting windings respectively. Other winding constructs could exhibit significant TDES without having the major axis of the winding cross-section (c, in this embodiment) much larger than the minor axis ($\Delta$, in this case). For example, a circular cross-section primary and secondary, with the diameter of the primary large compared to the gap between the primary and secondary windings, may provide significant TDES and be more desirable for specific applications. Typically, it is also desirable to have the primary width c larger than the secondary width d.

The transverse diffusion effect characteristic frequency (TDECF) is defined as the temporal excitation frequency of the input electric signal at which the currents within the primary windings transition from a nearly uniform distribution throughout the primary cross-section, as shown in FIG. 2a, to a distribution for which the currents are confined to a thin layer near the surface of the conducting windings. Near the TDECF, the distribution in the span-wise direction, y, cannot be approximated as uniform or as confined to a thin layer at the edge of the windings, as shown in FIG. 2b. In this range, it is necessary to account for the effects of this distributed current density on the measurements at the sensor winding terminals.

Often, the sensitivity to specific MUT properties of interest or the selectivity for two MUT properties of interest is increased when the frequency of the input electric signal is near the TDECF. The TDECF occurs at $f_{TD}=1/\tau_m$, where $\tau_m=\mu\sigma l^2$. In this relationship, $\mu$ and $\sigma$ are an effective permeability and conductivity, respectively. For example, the effective time constant $\tau_m$ for diffusion of magnetic fields within an aluminum ball that is surrounded by a highly permeable medium is somewhere between the permeability of the aluminum ball and that of the surrounding medium. Similarly, the diffusion of magnetic fields within the primary winding is not only controlled by the properties of the winding, but also it is influenced by the properties, proximity and shape of the neighboring media. The same logic holds for the effective conductivity, $\sigma$; that is, the effective conductivity which influences the diffusion of magnetic fields within the conducting sensor windings is not only influenced by the conductivity of the winding material 28, but also it is influenced by the conductivity, proximity, and shape of the neighboring media 8. The characteristic length, l, for diffusion of magnetic fields within the sensing windings derives from the geometry and dimensions of the windings themselves.

It is important not to mistake the TDECF for the common characteristic frequencies which produce the dominant phase shift in conventional eddy current sensors. In conventional eddy current sensors, the characteristic magnetic diffusion transitions within the MUT dominate the frequency response of the sensor. For example, a conventional eddy current sensor will observe a phase transition for measurements on a metal plate at the characteristic frequency which is related to the time constant of magnetic diffusion, $\tau_m$ within the MUT, where $\tau_m=\mu\sigma l^2$; but, now $\mu$, $\sigma$ and l are the effective properties within the MUT and $\tau_m$ is the time required for currents to redistribute, or for perturbations in the magnetic field to diffuse, across the characteristic length l, which is now representative of the MUT geometry and dimensions.

Often, conventional eddy current sensor measurements are made near this characteristic frequency of magnetic diffusion within the MUT. For TDES-based sensors, the sensitivity, selectivity, and dynamic range is often much higher near the TDECF, which is generally different than the characteristic frequency of magnetic diffusion within the MUT.

In fact, it is sometimes necessary to intentionally shift the TDECF away from the characteristic transition frequency associated with magnetic diffusion within the MUT in order to measure the preselected MUT properties of interest with the required levels of sensitivity, selectivity, and dynamic range. The designer has the ability to vary the TDECF by changing the characteristic lengths for the winding construct, altering the electric properties and cross-section shape of the windings themselves, or by adding a conducting back-plane with specified properties or a magnetic substrate of known complex permeability with or without a controlled bias field. Each of these provide the designer with additional design degrees-of-freedom to permit adaption to new applications and material properties.

Figure 2:
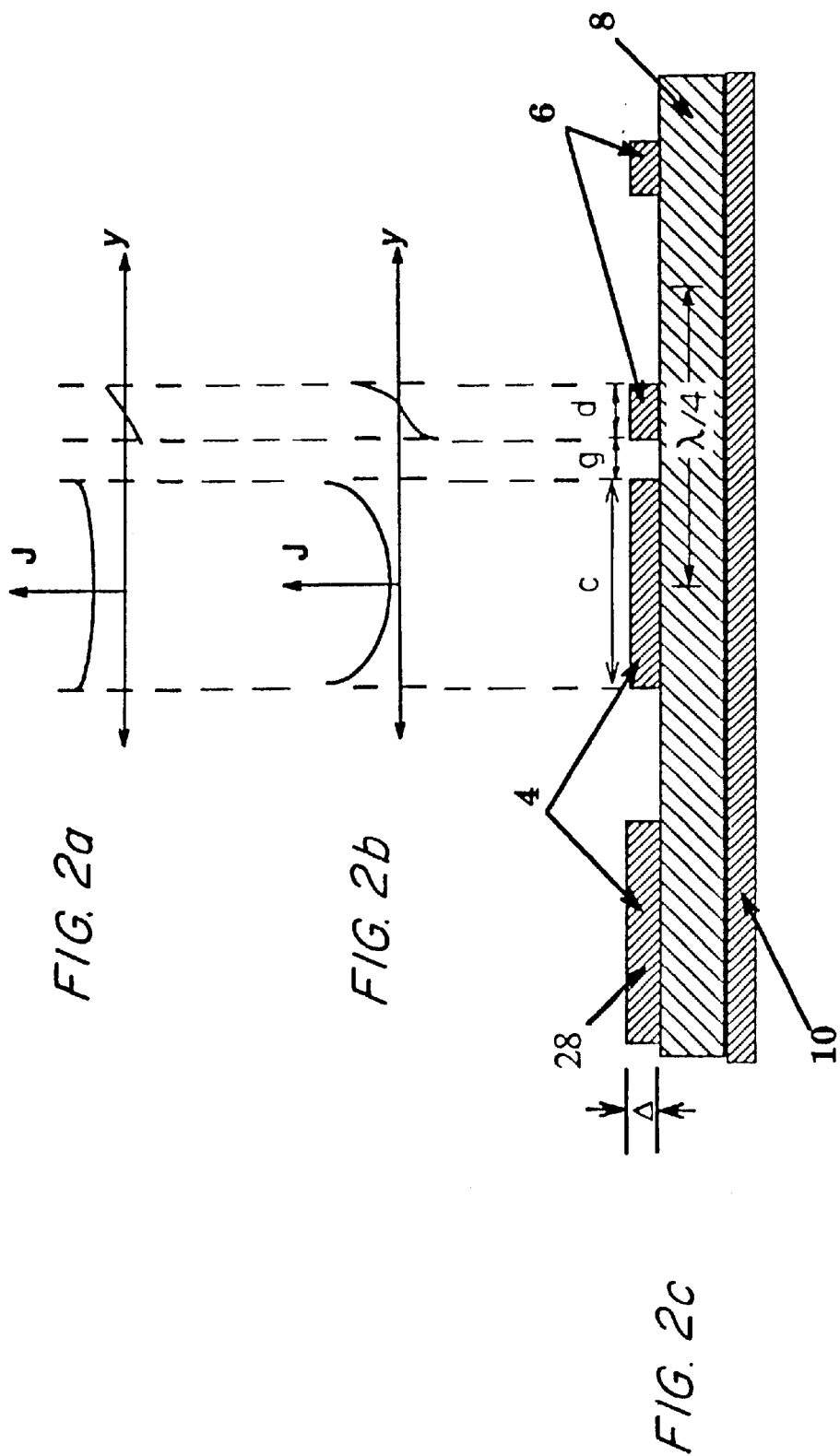
FIG. 2c is a schematic cross-sectional view of a sensor winding construct showing an embodiment of the invention which has a primary width larger than the gap between the primary and the secondary winding, and FIGS. 2(a–b) show the distribution of the current density, J, in the span-wise (transverse) direction at two different temporal excitation frequencies.

Although TDES-based sensors with circular windings may be desirable for some applications, there are advantages to the winding geometry illustrated in FIGS. 2(a-c) with c>d>>$\Delta$. These advantages are explained in the following few paragraphs.

At input excitation frequencies well below the TDECF, the current density, J, within the primary winding is essentially uniform throughout the winding cross-section. As the excitation frequency is raised, the currents begin to "crowd out" towards the surface of the conducting windings. This effect, referred to as transverse or span-wise diffusion of currents within the conducting windings, results from the tendency of conductors to act in a manner which excludes magnetic flux when it is changing rapidly with time. This is often referred to as the skin effect, because at high enough frequencies, the currents within conducting media are confined to a thin layer, "skin", near the surface of the conductor. The approximate thickness of this layer is commonly referred to as the skin depth, and is given by $\delta=\mathrm{SQRT}[2/(\omega\mu\sigma)]$. At frequencies well above the TDECF, the surfaces of the conducting windings become equipotentials and the windings act as perfect conductors.

For TDES-based sensors with c>>$\Delta$, there is a range of frequencies over which the effects of span-wise diffusion, in the transverse direction y, (i.e., in the direction perpendicular to the imposed current flow and along the winding plane) on measurements at the winding terminals are significant, but the currents are essentially uniform with respect to the transverse direction x, (i.e., the direction perpendicular to the imposed current flow and perpendicular to the winding plane). In this frequency range, it is possible to accurately model and predict the response of specific winding geometries for a wide range of MUT properties of interest.

Figure 10:
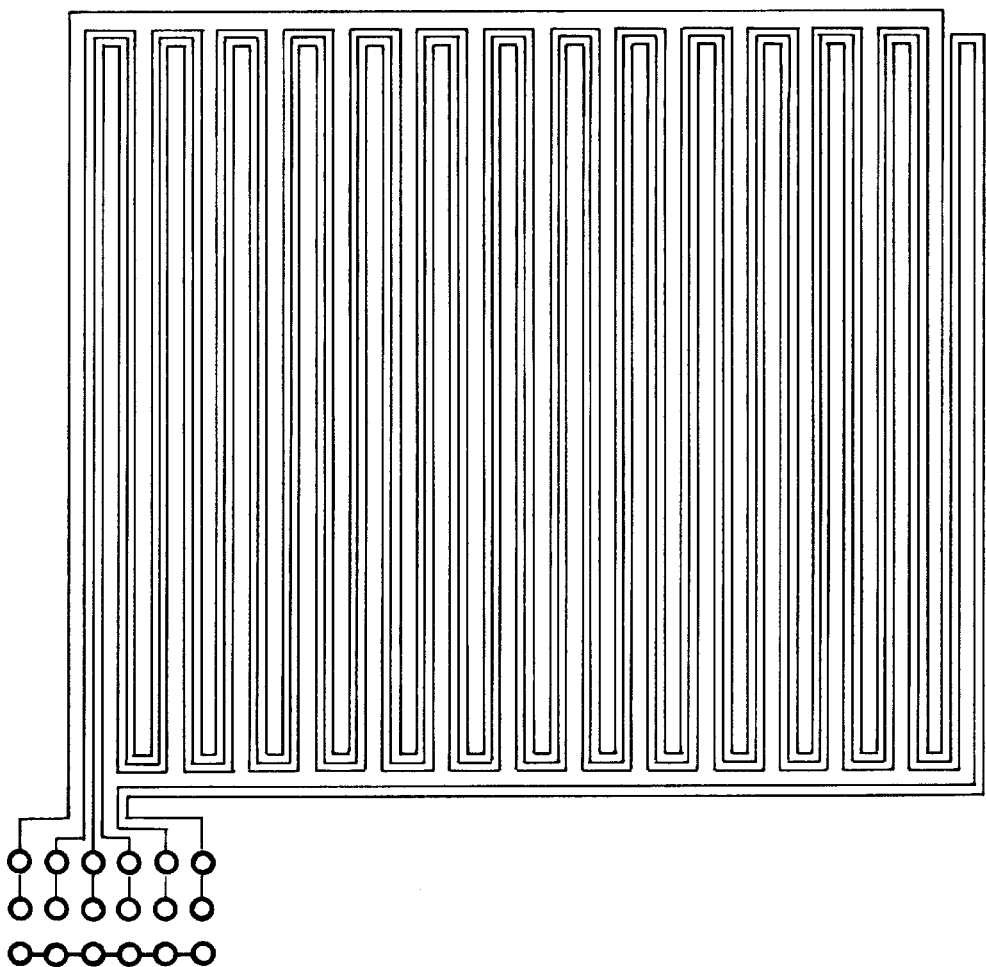
FIG. 10 is a top view of a mask for an embodiment of the invention called the Inter-Meander Magnetometer, an example of a meandering array that applies a magnetic potential to the MUT with several cycles of the same spatial wavelength.

One such winding construct which may be accurately modeled is the Inter-Meander Magnetometer construct. The mask for this winding construct is shown in FIG. 10. The primary winding 4 meanders through several wavelengths, $\lambda$, and has terminal measurements ($v_1$, $i_1$). Two secondary windings 6 meander on opposite sides of the primary. As described in the Magnetometer Windings section, these terminals can be connected in several different ways to achieve different measurement objectives. In the principal usage, the secondaries are connected in parallel, and the secondaries links flux over the same area. This winding design is discussed further in the Inter-Meander Magnetometer Design Section. A complete continuum model for this magnetometer is presented in later sections. Examples of parameter estimation grids and measurement optimization techniques are also included for specific applications.

For the Inter-Meander Magnetometer construct shown in FIG. 10, with $\lambda > c > d > g$ and $c >> \Delta$, the ability to accurately predict the response at the terminals of the sensor winding results in the accurate estimation of absolute material properties, without the need for calibration or measurements on calibration test pieces. The ability to accurately predict this response is the result of careful design of the Inter-Meander Magnetometer winding geometry and construct to intentionally provide physical behavior which is easily modeled. This is different than the standard approach of designing the winding geometry for high sensitivity, without considering the modeling consequences. The model described in detail later, uses modal analysis techniques (Fourier series solutions of partial differential equations), with numerical solutions based on the method of weighted residuals to handle the boundary (jump) conditions at the interfaces between homogeneous layers, and the continuity constraints.

The inclusion of multiple meandering wavelengths minimizes the unmodelled effects at the winding edge on the response at the winding terminals and provides increased sensitivity to MUT properties of interest for many applications. The measurement of actual, absolute physical properties is possible under many conditions without the use of calibration test pieces. This results in significant cost saving potential for a wide range of applications, as well as a substantial increase in the usefulness of such property measurements for quality monitoring and control, process control, and other applications requiring accurate measurement of single or multiple physical or geometric MUT properties over a wide dynamic property range.

Other winding geometries, that do not include multiple wavelengths, such as those in FIGS. 4 through 9, must be modeled in a different manner. Continuum models for these geometries could use modal analysis with Fourier Transforms, or 2- and 3-dimensional finite element techniques. Model stability and accuracy is the key to accurate response prediction, which is the key to accurate and repeatable estimation of single and multiple MUT properties. The model must be a continuum model, as lumped parameter models will not include the effects of transverse diffusion in the windings, and will not be able to produce the required sensitivity to MUT properties of interest for many applications of interest. A variety of different winding geometries are possible, as shown in FIGS. 4 through 11. These are described in some detail in the Magnetometer Windings and Sensor Construct section.

Generalized Material Under Test Property Estimation Framework

The methods and techniques of the disclosed invention comprise a general property estimation framework. A typical measurement procedure flow would include the following steps (also shown in the procedure flow diagram in FIG. 3):

Step 1 Define MUT property measurement requirements—define the dynamic range and measurement tolerance requirements for the MUT properties of interest.

Step 2 Select sensor winding geometry and configuration—select a sensor winding geometry and configuration (i.e., referring to FIG. 1, the structure, shape and design of the primary 4 and secondary 6 windings, and the back-plane 10 and substrate 8 and 9 characteristics, with c>g). Selection is based on test and evaluation of property estimation sensitivity, dynamic range, and selectivity, using the predicted responses and measurement grids 18 generated by the continuum model 20 or through experimental measurements on calibration test pieces over the required range of properties for a variety of winding geometries, dimensions and configurations.

Figure 14:
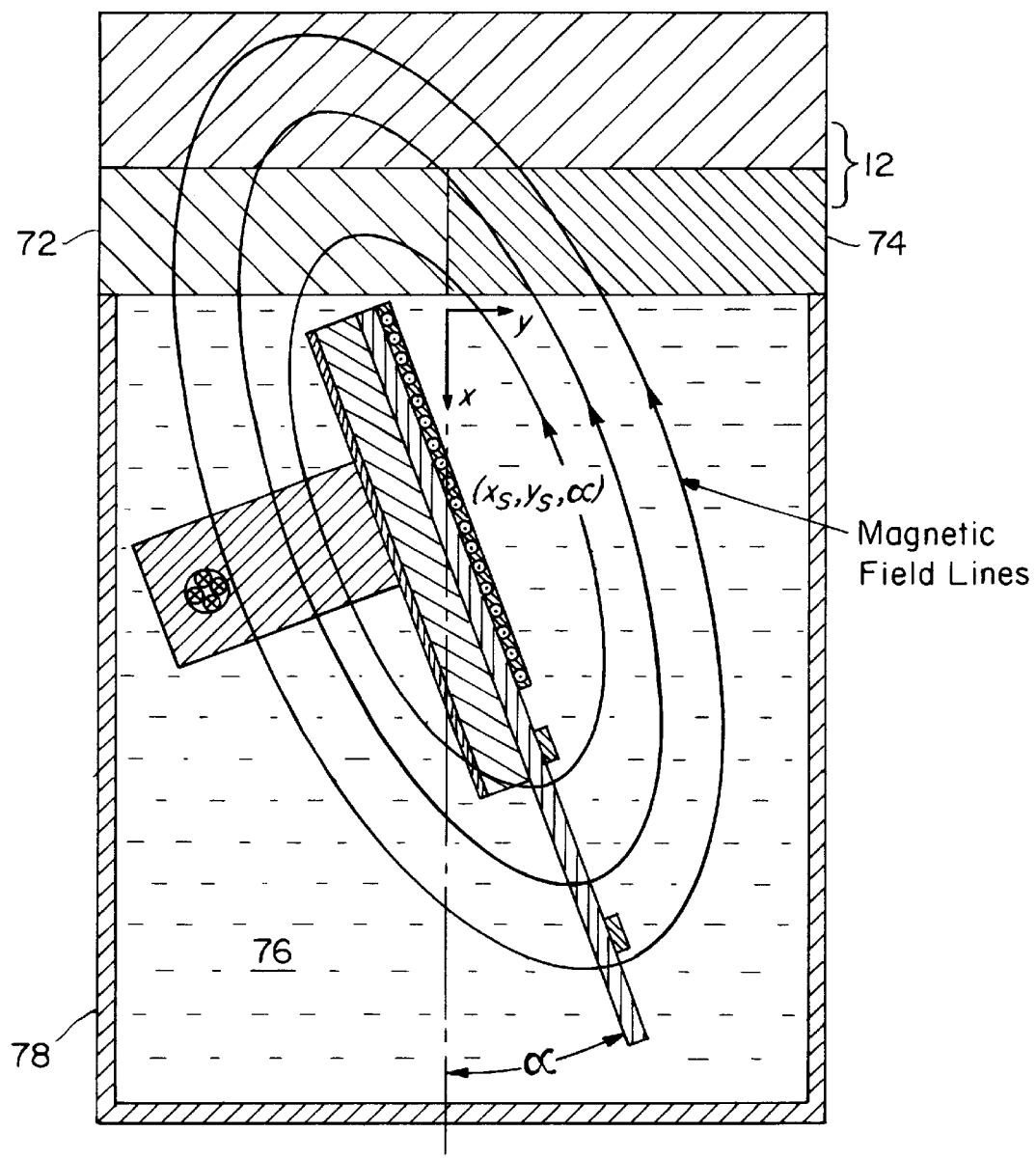
FIG. 14 is a cross-sectional view of a sensor winding construct that has its relative position to the material under test defined by the coordinates ($x_s$, $y_s$, $\alpha$).

Step 3 Analyze the property estimation grids and Operating point responses to define the measurement strategy—the measurement strategy includes the number of measurements required at different operating points and with different sensor geometries, dimensions and configurations. A continuum model 20 or set of experiments is used to generate property estimation grids 18 and a set of response curves which are functions of operating point parameter variations. Operating point response curves include (1) the standard temporal frequency response, and responses to (2) variations in the defined spatial wavelength of the sensor winding construct (the defined spatial wavelength $\lambda$, is the wavelength of the dominant eigenfunction, or Fourier component, in the magnetic potential distribution imposed along the surface of the MUT; the defined spatial wavelength can be adjusted in actual measurements by including several similar winding constructs, each with a different defined spatial wavelength, as described in U.S. Pat. No. 5,015,951), (3) the relative position of the winding construct to the MUT (including the height above or below the MUT surface, $x_s$, the position along the surface, $y_s$, and the orientation relative to the surface, $\alpha$, as shown in FIG. 14), and (4) adjusting the geometry of the winding construct (including the distance between the primary 4 and secondary 6, g; the relationship between the primary width, c, and the defined spatial wavelength, $\lambda$; the relative position of the back-plane 10 to the winding plane; and in the case of magnetic media the magnitude, direction, and spatial or temporal variation of an applied DC or AC bias field.

Step 4 Determine optimal operating point(s) and winding dimensions—a set of operating point parameters, for one operating point, includes the proximity to the MUT, h, the temporal excitation frequency, f, and all other adjustable parameters described in step 3. Singular value decomposition on the Jacobian, relating variations in the transimpedance magnitude and phase to variations in the MUT properties of interest, is used when an accurate continuum model is available to determine the relative performance potention at different operating points (if such a model is not available, a set of carefully designed calibration experiments can be used, along with models of related winding and MUT geometries to provide additional insight). Relative performance potential includes sensitivity to variations in the MUT properties of interest, selectivity for pairs of properties of interest, and dynamic range for each property of interest. Then parameter estimation grids 18 are generated at optimal/selected operating points along with operating point response curves for use in property estimation, Step 6.

Step 5 Measure transimpedance for MUT at each operating point—measure the transimpedance at each prescribed operating point defined in the measurement strategy, using the impedance analyzer 14.

Step 6 Estimate the preselected MUT properties—estimate the MUT properties of interest, using root-searching techniques, trial and error, table look-up and interpolation; or graphical interpolation from measurement grids 18 generated with the continuum model 20 (or calibration experiments). This is accomplished in the property estimator 26.

Step 7 Estimate the property estimation tolerances—using measurement grids 18 and operating point response curves generated with the continuum model 20 (or calibration experiments) and the measurement tolerance specifications of the impedance analyzer 14, estimate the measurement tolerances and tolerance variations over the dynamic range of interest for each pre-selected MUT property of interest. If the property estimation measurement requirements are not achieved, repeat steps 2 through 7.

For any application, calibration experiments can be used to tune the model parameters and improve MUT property estimation accuracy. Such calibration, although not always required, should always be used when available.

Magnetometer Windings and Sensor Construct

As shown in FIGS. 4 through 11, there are many winding geometries and constructs that can provide the required relationship, c>g, for the sensor winding dimensions. In each of these winding constructs, the deposited windings are confined to one surface as in FIGS. 4 through 7 or two surface as in FIGS. 8, 9 and 11(a–b). These surfaces can be planes in Cartesian coordinates (as in FIGS. 4 through 11(a–b), cylinders or arcs in cylindrical coordinates, as in FIGS. 12a and 12b, or spiral surfaces (each layer approximately cylindrical, as in FIG. 12c) when it is desirable to wrap the winding construct around a circular cylinder for measurements on surfaces with other complex shapes.

Figure 12A:
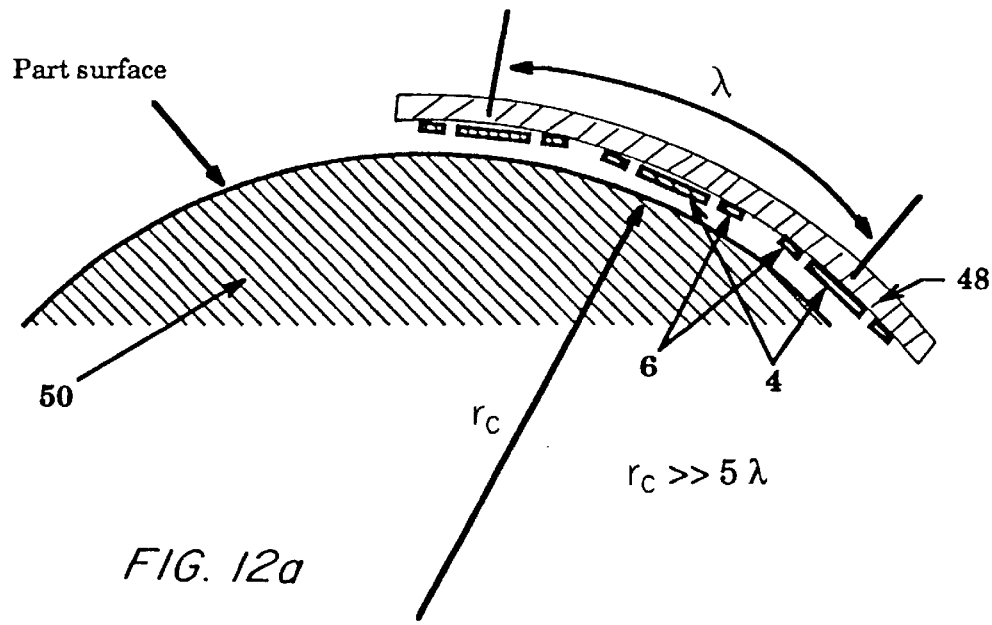
FIGS. 12a, b and c are cross-sectional views of three winding geometries for measurement of physical and geometric properties of curved parts.
Figure 12B:
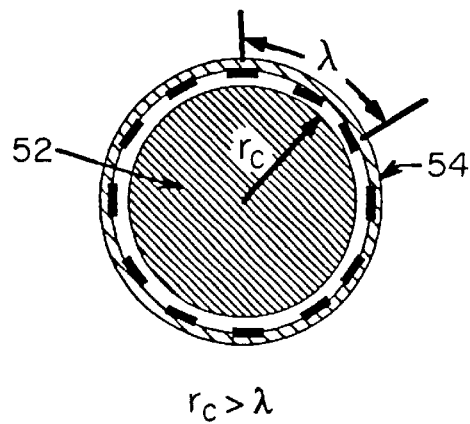
Figure 12C:
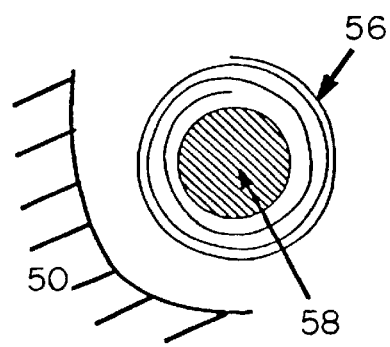

Examples of cylindrical 54, wrapped 56, and curved 48 winding constructs are shown in FIGS. 12(a–c). If the local radius of curvature is much larger than 5 times the defined spatial wavelength of the winding construct for the Inter-Meander Magnetometer, then the Cartesian continuum model, presented for the Inter-Meander Magnetometer, can be used to obtain accurate MUT property estimates without calibration. For a smaller radius of curvature, either calibration is required or models must be formulated in cylindrical coordinates. For small cylindrical parts, it is also possible to wrap the winding construct around the part as shown in FIG. 12c (this is accomplished by depositing the winding onto a flexible substrate material 56). The windings can also be wrapped around a cylindrical insulating, conducting or magnetic core 58 (i.e., as opposed to wrapping the flexible sensor around a cylindrical MUT 52) to make measurements on curved or flat surfaces 50, which are in close proximity to the cylindrical core 58.

Figure 13:
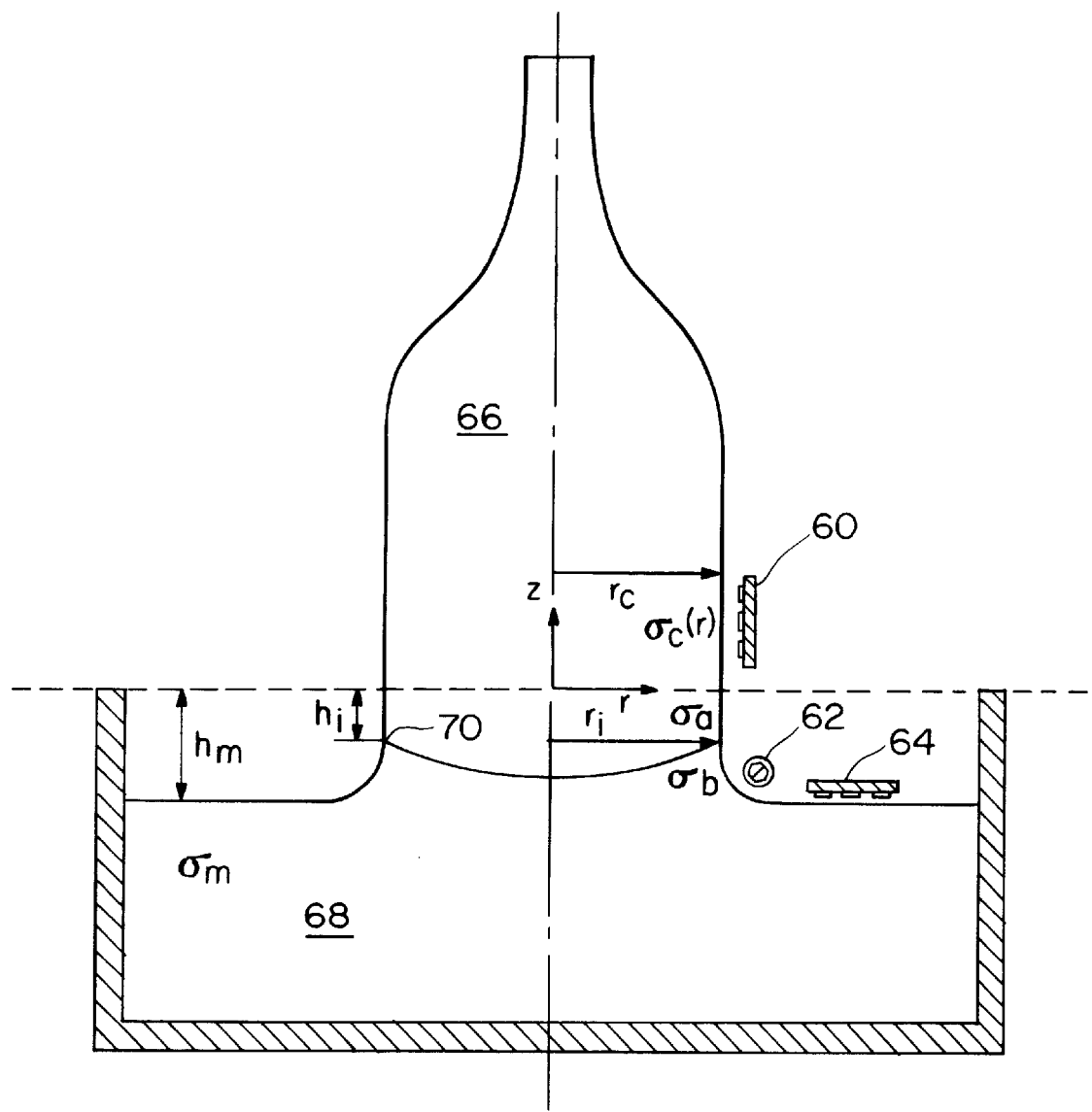
FIG. 13 is a cross-sectional view of a III-V compound crystal growth process with a melt-condition-probe, a liquid-solid interface-condition-probe and a crystal-condition-probe.

One application which could use a wrapped Inter-Meander Magnetometer winding construct with multiple turns around a magnetic 58 or insulating cylindrical core is the control of III-V crystal growth processes, such as for gallium arsenide or indium phosphide. An illustration of this application is shown in FIG. 13. The melt-condition-probe 64 could first establish the position of the melt height at the exposed melt surface. Then, the Interface-condition-probe 62 could be moved in towards the liquid-solid interphase three-phase-point 70 to obtain estimates of the diameter, $2r_i$ and height, $h_i$, of the liquid-solid interface. The melt-condition-probe 64 could be the standard Cartesian coordinate Inter-Meander Magnetometer shown in FIG. 10. Once stable crystal growth is achieved, with essentially uniform constant diameter, a crystal-condition-probe 60 could be used to measure the diameter and the physical properties near the surface of the solid gallium arsenide crystal, just above the liquid-solid interface. For example, the nature of changes in the electrical properties of a thin layer at the crystal surface a few centimeters above the liquid-solid interface is of interest to the control of the growth process.

The instantaneous position of the liquid-solid interface, solidification front, may be measured for other MUT geometries as well. For the example in FIG. 14, the MUT material in the horizontal layer closest to the sensor might be divided, as shown, into two regions. On the left 72, the material might be solid, and the material on the right 74 of the vertical interface (e.g., solidification front) might be liquid. By moving the probe relative to the MUT surface and monitoring its response, the location of the liquid-solid interface and the properties in each region could be estimated. It is also possible to use multiple probes at multiple incremental positions along the MUT surface.

Figure 11A:
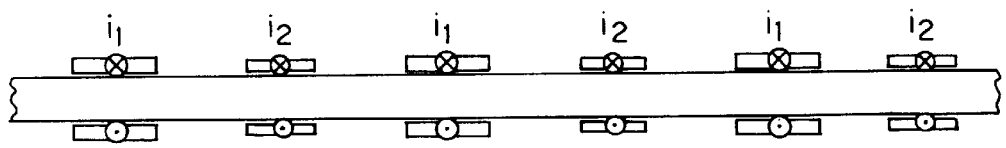
FIG. 11a is a cross-sectional view and FIG. 11b top view of a sensor winding geometry and construct that has the primary and secondary confined to two planes and applies a magnetic potential to the MUT with several cycles of the same spatial wavelength.
Figure 11B:
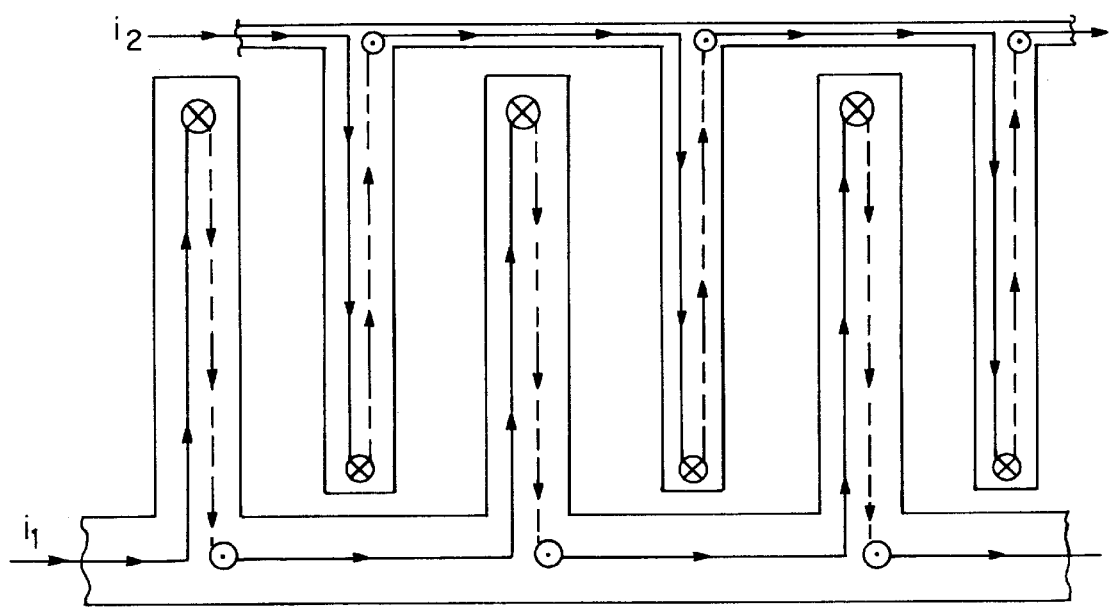

Furthermore, the winding constructs can incorporate multiple defined spatial wavelengths, as shown in FIGS. 10, 11(a–b) and 12(a–c), or single spatial wavelengths as shown in FIGS. 4 through 9. Also, it is possible to design a TDES-based sensor with only a primary winding 4 (i.e., no secondary 6) and measure only the impedance at the terminals of the primary winding. However, with only a primary winding, the effects of variations in the contact resistance must be carefully accounted for. The selection of winding geometry and construct will depend on the nature and configuration of the MUT and the MUT properties of interest, for each application.

The input electrical signal and the measurements at the terminals may vary with application. In the principal embodiment, the primary winding 4 is excited by a controlled current source, $i_1$, with a prescribed temporal excitation frequency, f, by an impedance analyzer 14. The output is the transinductance, $\Gamma = v_2/(j\omega i_1)$ where $v_2$ is the voltage measured at the terminals of the secondary winding 6 by the impedance analyzer 14. The transinductance is simply the derivative with respect to time of the transimpedance (i.e., the transimpedance divided by $j\omega$ where $j=SQRT(-1)$).

Figure 5:
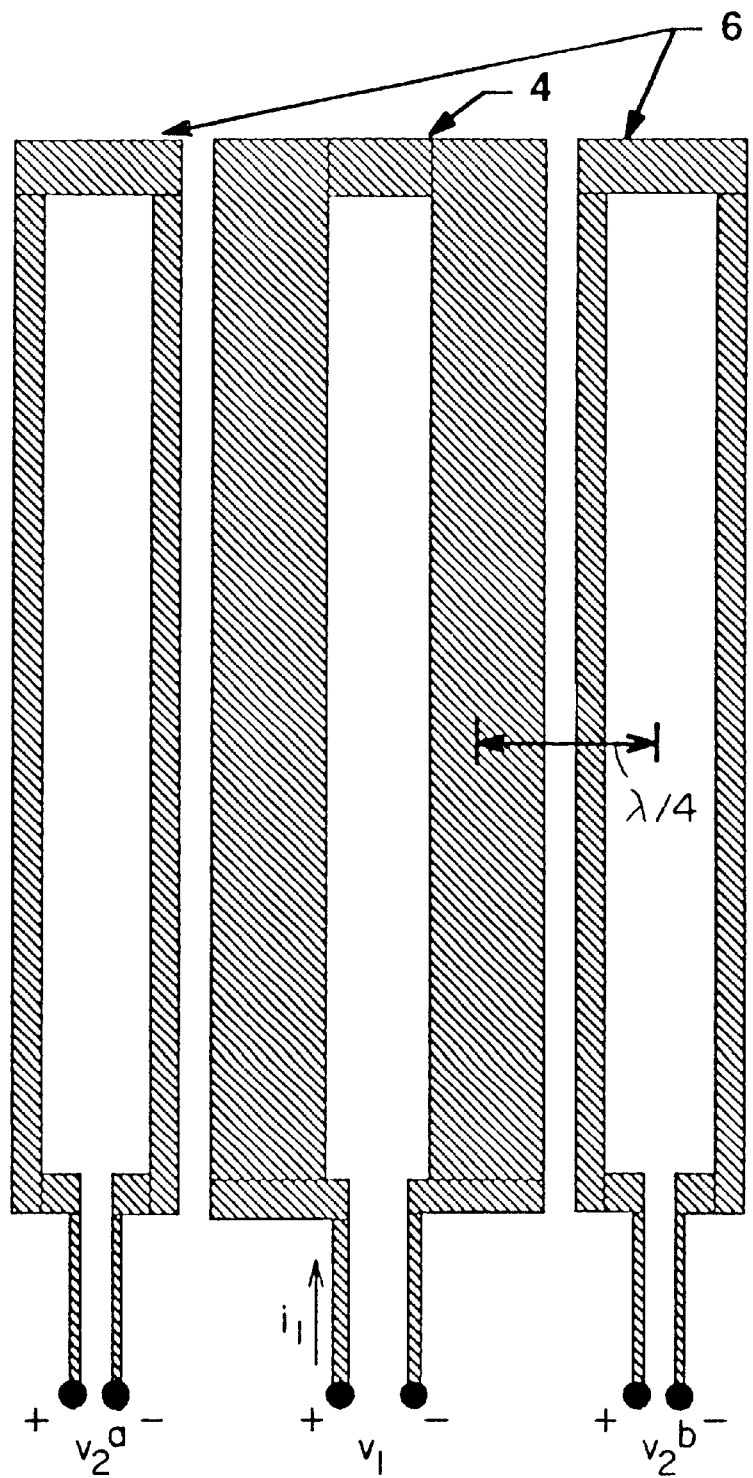
FIG. 5 is a top view of the winding geometry for an example of a single wavelength sensor construct with two secondaries to provide a differential measurement designed to provide increased TDES.
Figure 6:
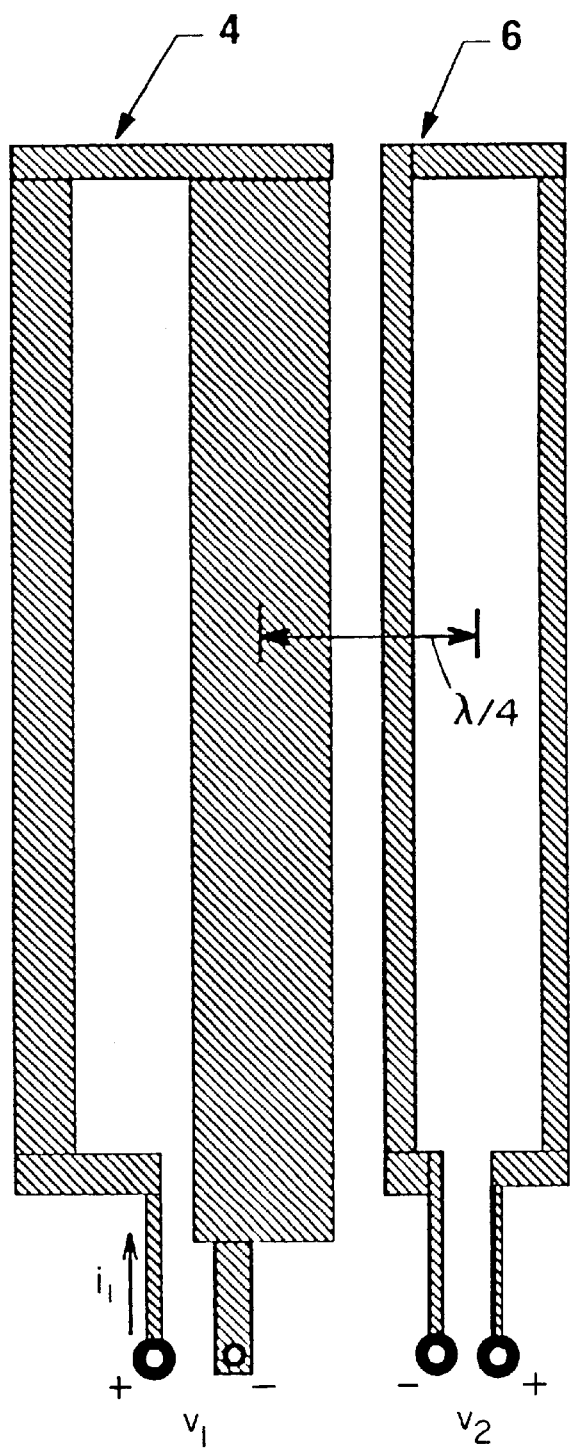
FIG. 6 is a top view of the winding geometry for another example of a single wavelength sensor construct designed to provide increased TDES.
Figure 7:
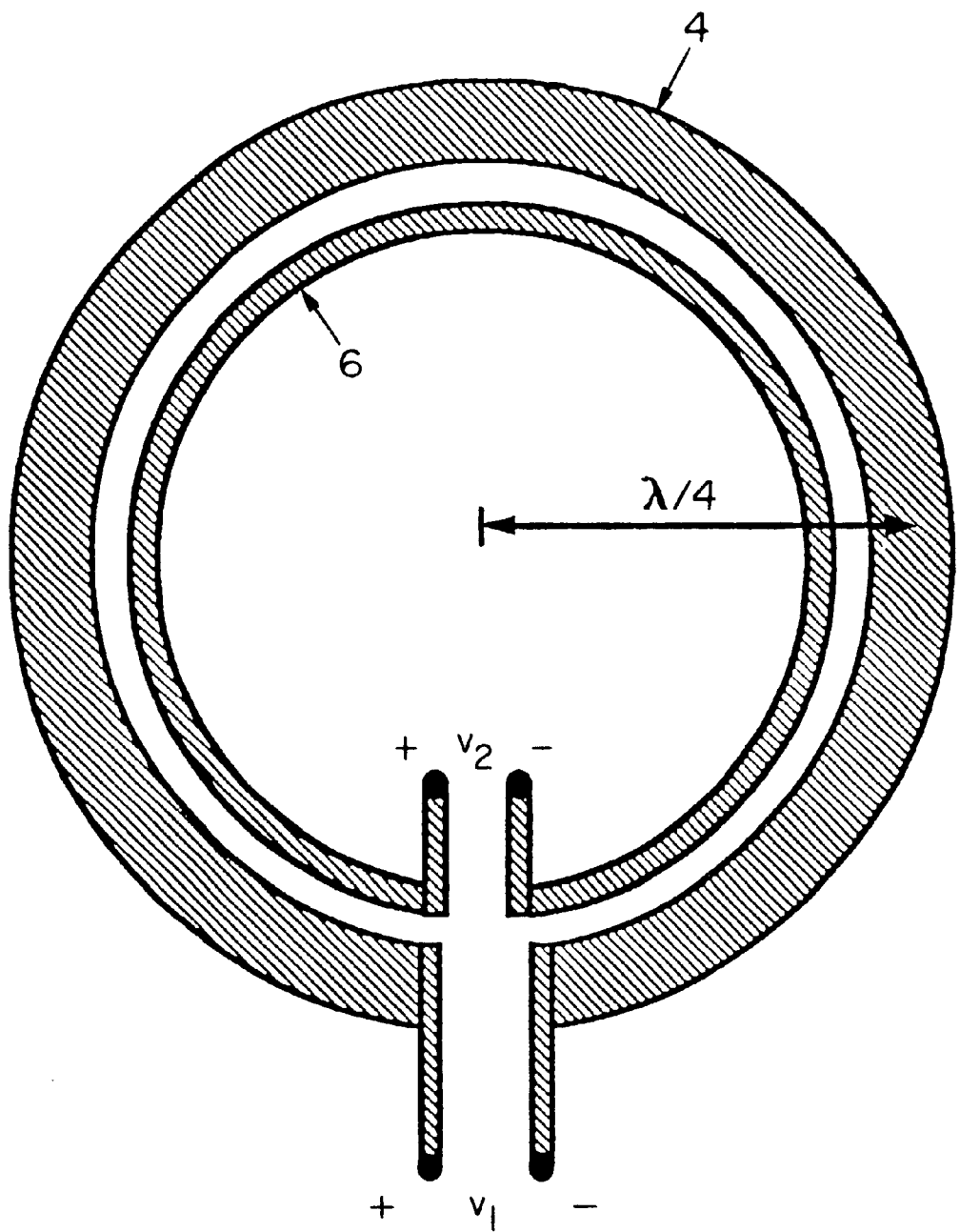
FIG. 7 is a top view of an example winding geometry for a single turn winding construct with a primary and a secondary designed to provide increased TDES.

It is also possible to have two or more secondary windings 4 placed in different proximity to the primary winding 6, as shown in FIG. 5; this is referred to as a differential measurement sensor. The differential measurement sensor will provide increased sensitivity to MUT property variations, surface shape variations, or proximity of the MUT when these variations occur in the direction defined by y in FIGS. 2(a–c), (i.e., along the winding plane and transverse to the direction of current flow). Also, the differential sensor might be used with a highly permeable substrate 9 to measure the relative motion of a liquid metal at low frequencies by intentionally shifting the TDECF so that measurements at the terminals of the sensor winding are sensitive to velocity variations in the liquid metal. The TDECF is shifted by altering the properties of the substrate 9 and back-plane 10 materials in the sensor construct.

Figure 8:
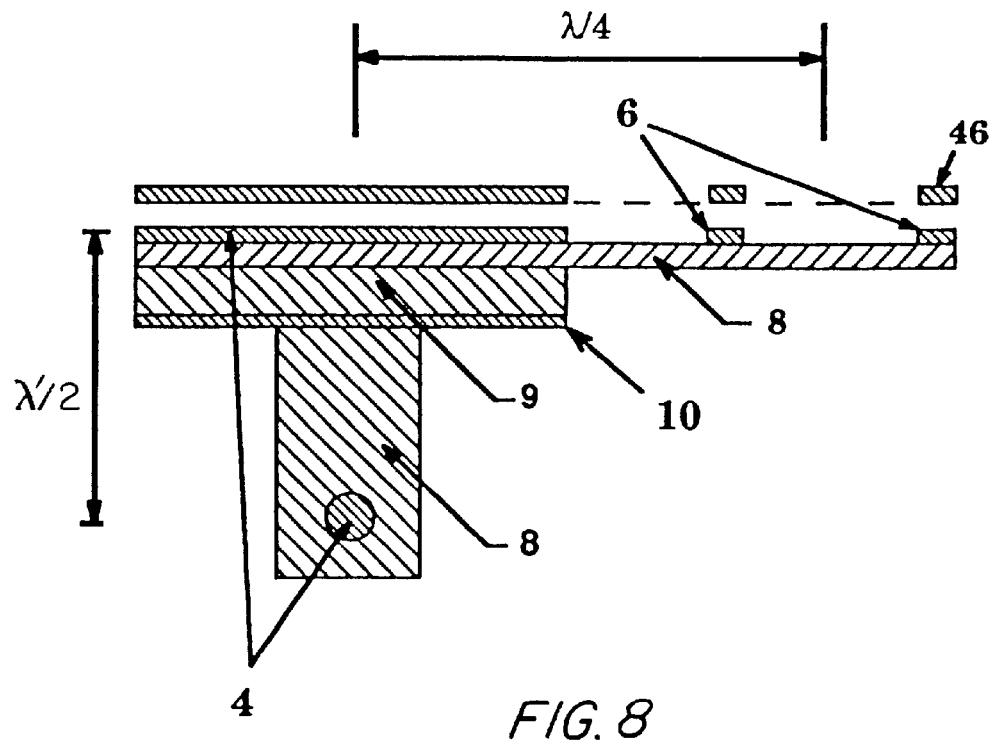
FIG. 8 is a cross-sectional view of an example single wavelength winding geometry and sensor construct with the primary and secondary confined to two planes (levels) and the current in the primary circulating in a direction perpendicular to the winding planes and designed to provide increased TDES.
Figure 9:
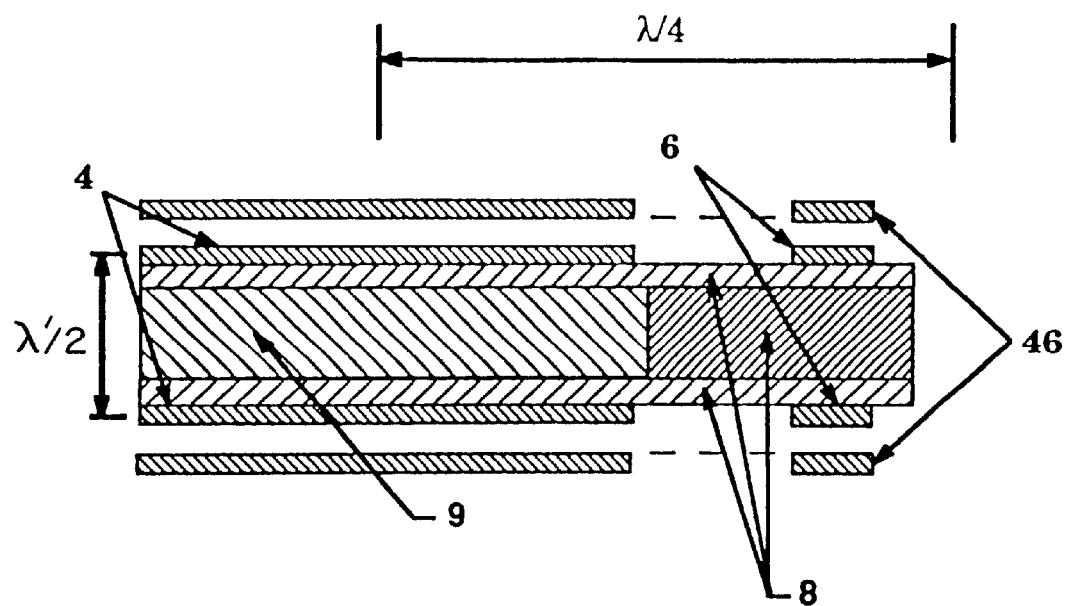
FIG. 9 is a cross-sectional view of an example single wavelength winding geometry and sensor construct with the primary and secondary confined to two planes (levels) and the current in the primary circulating in a direction perpendicular to the winding planes and designed to provide increased TDES.
Figures 15A, 15B:
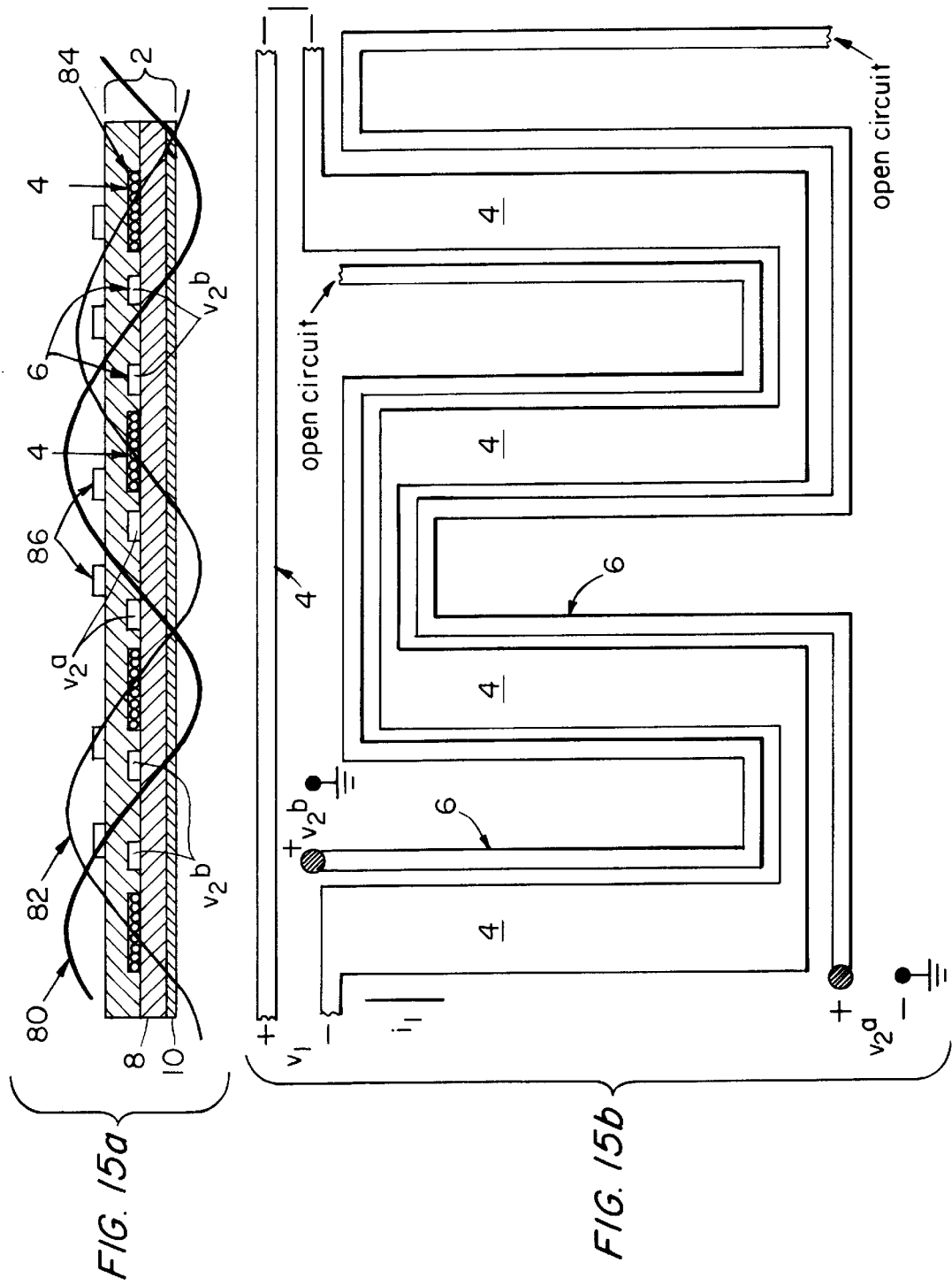
FIG. 15a is a cross-sectional view and FIG. 15b is a top view of a sensor winding construct that uses the Inter-Meander Magnetometer winding geometry at the drive plane to induce orthogonal electric and magnetic potentials, and has an optional secondary on a second level.

It is also possible to conceive TDES-based winding constructs that have the secondary 6 and primary windings 4 confined to different parallel surface levels, as shown in FIGS. 15(a–b), or in perpendicular planes. FIG. 8 provides a variation on the latter case, where the currents in the primary circulate in the plane perpendicular to the secondary winding surface, but the primary winding 4 has a cross-section in the plane of the secondary winding 6, with its major axis along that plane. The primary winding has a simple circular cross-section when it is not aligned with the secondary plane. This could be accomplished by depositing the secondary winding 6 and that portion of the primary winding which has its major axis along the secondary winding plane onto an insulating 8 or permeable substrate 9, and then driving the ends of the primary with cables which are carefully fixed to the desired geometry in the plane perpendicular to the secondary winding plane. One advantage of this geometry is the ability to include multiple primary winding turns by introducing a passivating layer between primary layers, to prevent current flow between turns. However, the effects on the TDECF must be carefully considered when multiple turns are used in such close proximity to each other. When the primary and secondary windings are not confined to single or multiple parallel planes, then a second defined spatial wavelength, $\lambda'$, is introduced for completeness, as shown in FIGS. 8, 9 and 11.

FIG. 14 illustrates the concept described earlier for scanning the relative position and orientation of the sensor to the MUT surface in order to provide additional parameter estimation information. The position $(x_s, y_s, \alpha)$, of the sensor relative to the MUT surface at the instant the measurement is made is considered part of the operating point specifications. If one operating point parameter (e.g., $x_s$) is varied while keeping all other operating point parameters (e.g., f, $\lambda$, $y_s$, $\alpha$) constant, the measurements at different values of that one parameter form an operating point response curve that can be used to improve parameter estimates over estimates obtained at a single operating point parameter set. Further, the estimation of more than two properties requires sensor terminal measurements at more than one operating point. For example, the magnitude and phase of the transinductance measured at one operating point can at best provide enough information to estimate two parameters.

An example of a multiple height, h=$x_s$, measurement to produce an operating point parameter response, with all other operating point parameters constant and with $\alpha$=90° is described later for measurement of the conductivity of a metal plate (using the Inter-Meander Magnetometer construct). The ability to independently measure the conductivity and air-gap height of the thick metal layer is also demonstrated. Many measurements of the conductivity are obtained, one at each height. This eliminates the common problem of lift-off error in measurements on conducting parts.

This independent conductivity and height measurement provides an enabling component of measurement systems designed to monitor aging/fatigue and detect cracks in metal parts. These systems would be far less costly if the lift-off error did not effect the accuracy of the MUT property measurements. One key capability is the ability to accurately measure dispersive (frequency dependent) conductivity, which would be significantly altered by the presence of macro- and micro-cracks at the surface and in the bulk of the MUT. Further, the variations caused by the presence of different sized cracks would vary with temporal excitation frequency, as well as with variations in other operating point parameters such as the defined spatial wavelength, $\lambda$. This supports the potential to estimate the depth below the surface, the size of large cracks, and the density of microcracks, by investigating the variation of the measured dispersive conductivity with the input current temporal excitation frequency. This is not possible with conventional techniques.

One additional variation on the apparatus illustrated in FIG. 1 is the inclusion of a magnetic coupling media which increases the coupling of the magnetic flux to the MUT in a manner similar to the common practice of introducing a coupling media for ultrasonic matching for ultrasonic measurement probes. The introduction of a magnetic media (liquid or solid) surrounding the sensor windings might also be used to alter the TDECF for the sensor.

Figure 35:
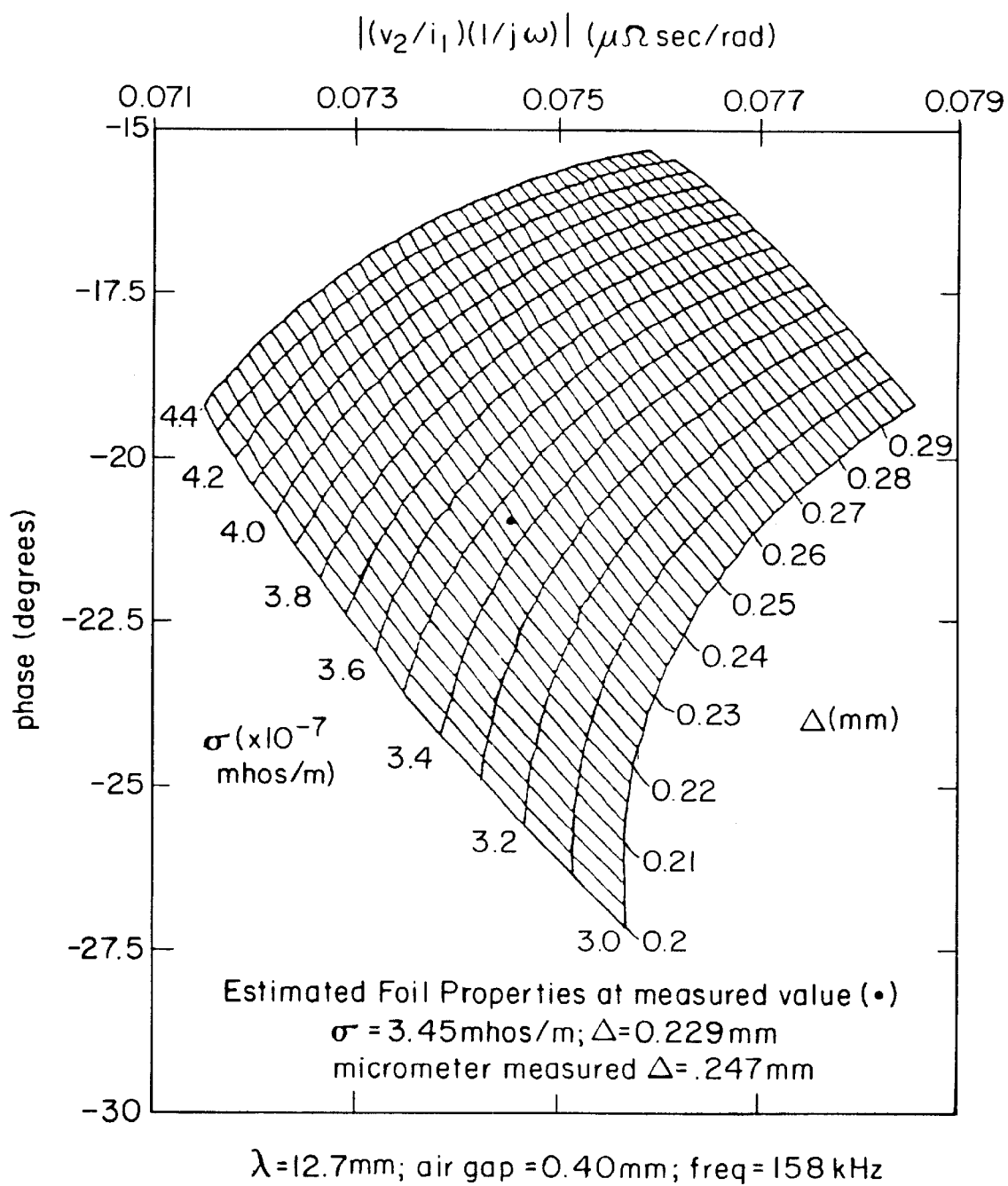
FIG. 35 is an example of a two-dimensional property estimation grid for conductivity and thickness measurement on a metal foil.
Figure 36:
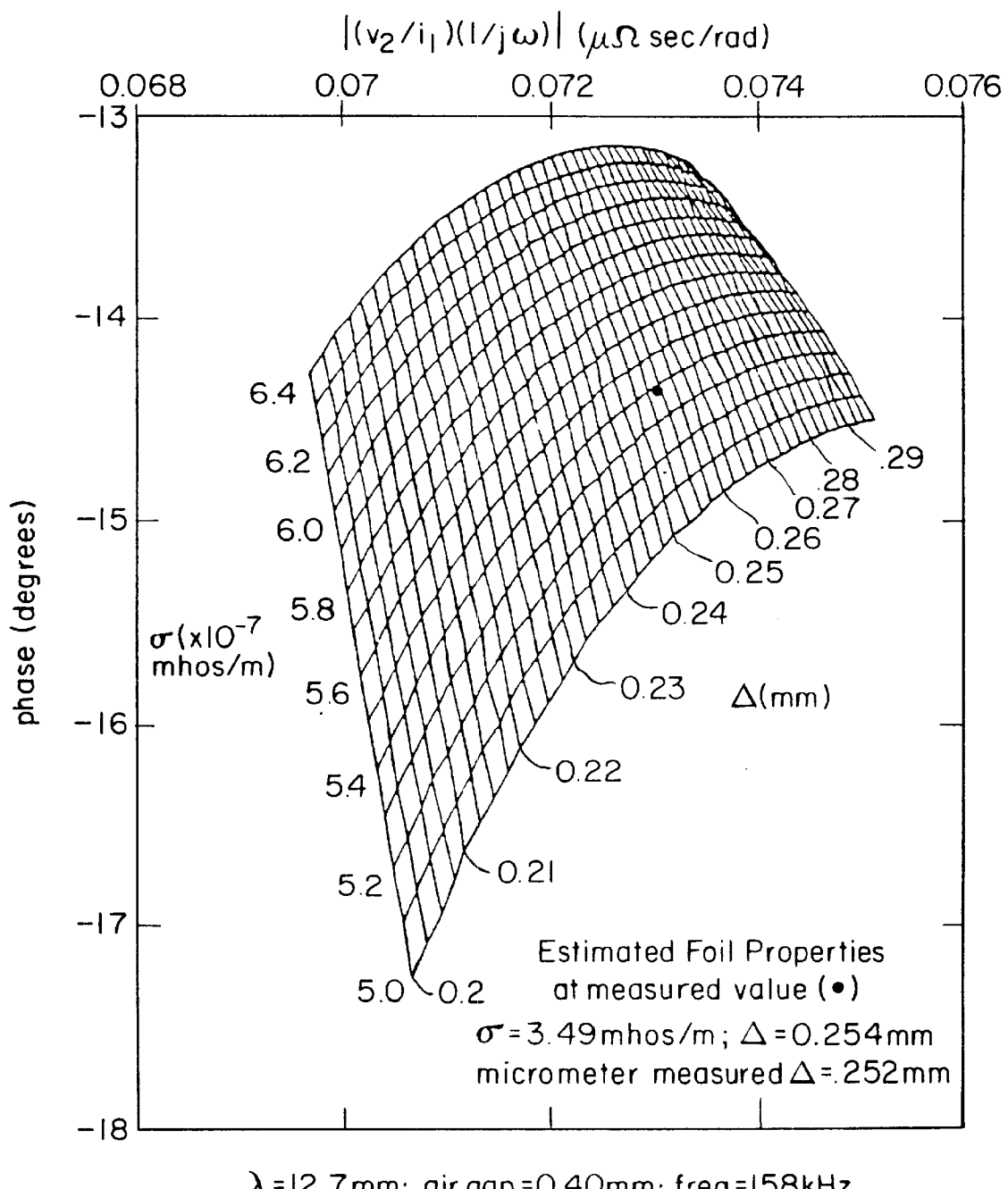
FIG. 36 is another example of a two-dimensional property estimation grid for conductivity and thickness measurement on a metal foil.

In many measurements, TDES is the enabling feature (e.g., the independent measurement of conductivity and thickness for thin metal layers, demonstrated in FIGS. 35 and 36). However, in other applications the special design of the Inter-Meander Magnetometer and the accuracy of the continuum model 20 provide the enabling features without requiring operation near the TDECF. For example, the accurate measurement of conductivity-thickness product can be achieved, as demonstrated in FIGS. 37(a–b) and 38(a–b), for thin conducting layers by obtaining a simple frequency response, without operating near the TDECF. The measurement optimization methods described later may be employed to maximize sensitivity, selectivity, and dynamic range to MUT properties of interest, both with and without operating near the TDECF.

Another variation on TDES-based sensors, is the use of a driven electroquasistatic electrode, or electrode pair, to alter the distribution of currents within the primary sensor winding 4. As illustrated in FIGS. 15(a–b), a sensing winding 86 could then be located on a parallel plane at a different level. One embodiment, shown in FIGS. 15(a–b), includes the application of an imposed electric potential 82 that is 90° out-of-phase with the imposed magnetic potential 80. The key feature is the capacitive coupling between the wide primary 4, which is driven by a current source, and the two secondaries 6, which are driven by voltage sources, $v_2^a$ and $v_2^b$, in "push-pull" manner. Variations on this design permit some active control of the distribution of currents within the conducting windings, and may allow increased sensitivity, selectivity, and dynamic range for specific applications. The principal use of this type of measurement is for MUT properties that are outside the dynamic range of the magnetometer without this added capacitive coupling. Note that the winding geometry, shown in FIGS. 15(a–b), for the drive-plane 84, with top view shown in FIGS. 15(a–b), is identical to the Inter-Meander Magnetometer geometry, where the primary 4 is driven with a current source and the secondary 6 is now separated into two driven electrodes with independent or dependent voltage sources. The mask for the Inter-Meander Magnetometer, shown in FIG. 10, was designed to support this usage. The user adjusts the terminal connections and drive sources appropriately for the MUT property measurements required.

One method for parameter estimation, using the Inter-Meander Magnetometer construct involves the addition of a correction for the capacitive coupling between the primary and secondary windings. This correction could be included in a lumped parameter modeling sense by adding a lumped capacitance to the continuum model in parallel to the mutual inductance between the primary and secondary windings. The result is the addition of a capacitive coupling correction term which is proportional to the angular frequency, ω, of the input electric signal raised to the third power. The terminal current, i, and voltage, v, are then related by $$\hat{i} = j\omega C \hat{v} + \frac{\hat{v}}{j\omega L} \quad (1)$$

resulting in a transimpedance with a clear frequency dependent capacitive coupling.

$$\frac{\hat{v}}{\hat{i}} \approx \frac{j\omega L}{1 - \omega^2 LC} \approx j\omega L[1 + \omega^2 LC] \quad (2)$$

This is consistent with the behavior observed in experiments with the Inter-Meander Magnetometer at high temporal excitation frequencies, when the capacitive coupling term becomes significant. This could also be modeled in a continuum sense by adding higher order terms in the electric field representation.

Measurements in air, or on calibration test pieces can also be used to tune the winding dimensions and conductivity inputs to the continuum model to adjust for inaccuracies in winding construct fabrication. It is important to accurately represent the winding properties in the continuum model 20 in order to achieve absolute, uncalibrated MUT property estimation, or to limit the cost of calibration by requiring only a few prespecified calibration tests (e.g., in air).

The introduction of capacitive coupling corrections will permit the extension of the dynamic range for MUT properties of interest in specific applications, by permitting measurements at temporal excitation frequencies at which capacitive coupling is significant, or by intentionally designing winding constructs with significant capacitive coupling between the primary 4 and secondary 6 windings, in order to increase sensitivity to specific MUT properties of interest. Sensors intentionally designed to incorporate both magneto-quasistatic (M.S.), inductive coupling terms and electroquasistatic (EQS), capacitive coupling terms are referred to here as hybrid M.S./EQS sensors. These sensors may have applications for materials such as biological media, or ceramics which have properties that are out of the dynamic range of existing M.S. magnetometers and EQS dielectrometers.

Figure 16:
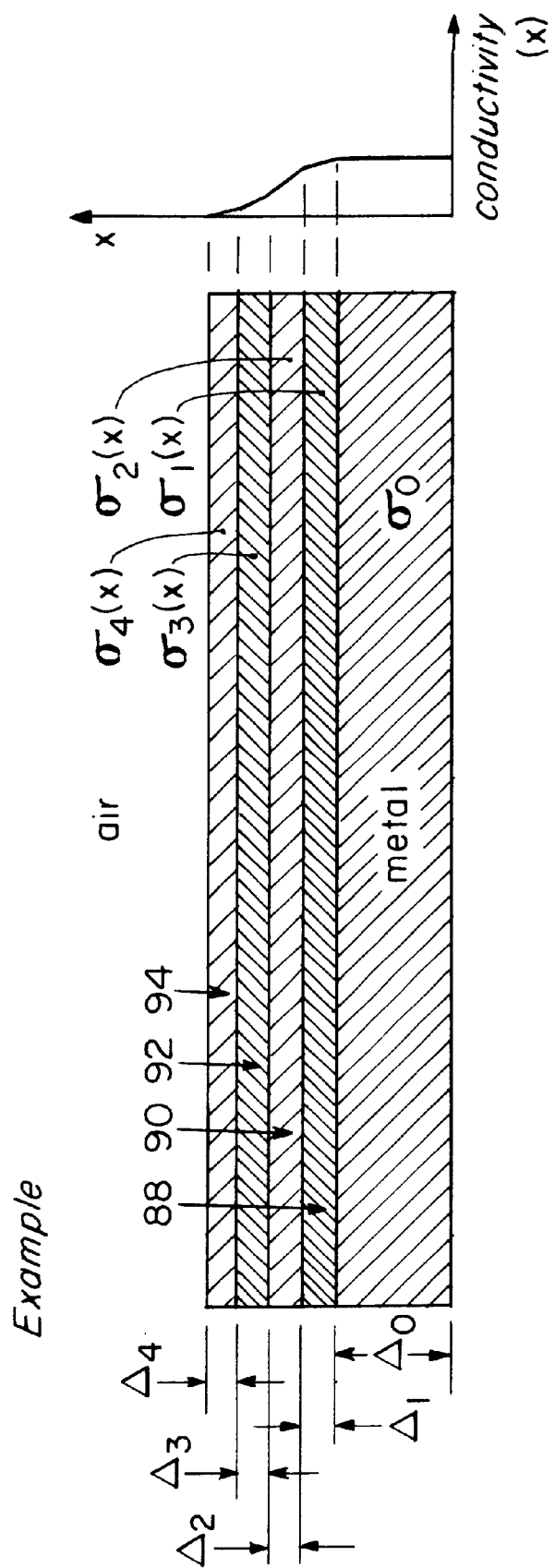
FIG. 16 is a cross-sectional view for a multiple layered material under test with a conductivity which transitions from the conductivity of the metal substrate to the conductivity of air.
Figure 17A:
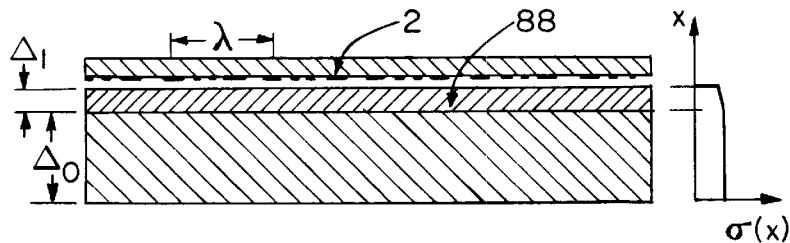
FIGS. 17(a–d) are a series of cross-sectional views of the property estimation steps for monitoring and control of the manufacturing of a multi-layer MUT.
Figure 17B:
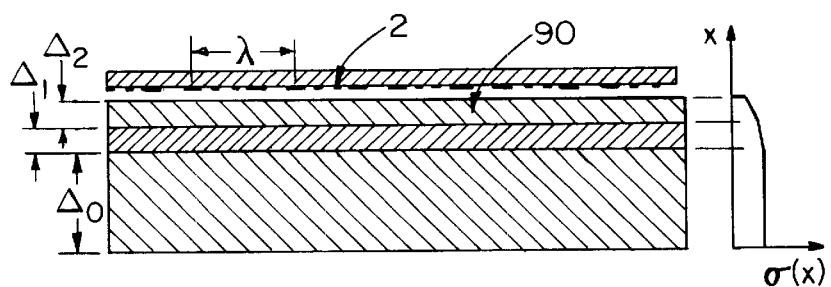
Figure 17C:
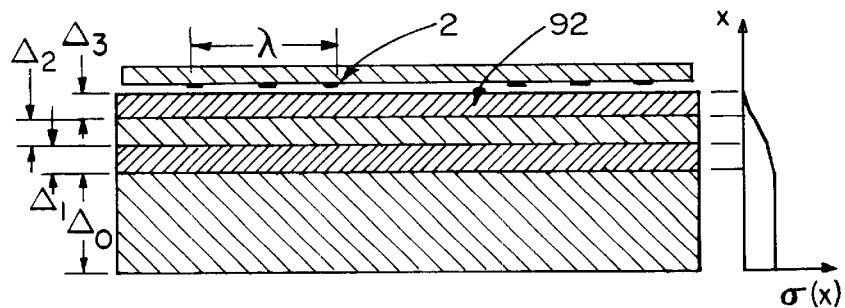
Figure 17D:
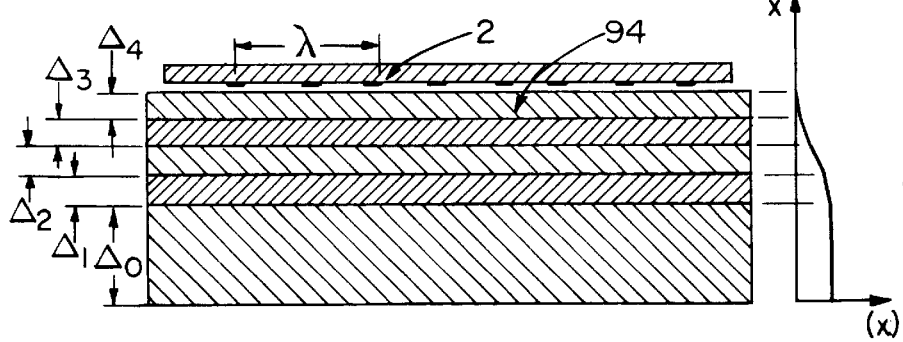

One application of interest which involves the use of the Inter-Meander Magnetometer in several different modes is illustrated in FIGS. 16 and 17. For example, consider a multi-layered media designed not to reflect electromagnetic energy in specific wavelengths. Such a multi-layered media might be conceived with the conductivity varying from the conductivity of a conducting substrate (e.g., metal) at the bottom of the first layer, to that of air at the top of the last layer, along the direction, x, perpendicular to the surface of the metal substrate (as shown in FIG. 16).

For this example, the manufacturing and quality control procedure might follow the following steps (the quality control steps 3, 5, 7 and 9 are shown in FIG. 17):

| Manufacturing Steps | Property Estimation Quality Control |
|---|---|
| Step 1 | Estimate the complex permeability and conductivity of the metal plate (including any heat affected zone properties near the metal surface), using the Inter-Meander Magnetometer in M.S. mode. |
| Step 2 | Apply layer 1 (thickness $\Delta_1$) to metal plate. |
| Step 3 | Estimate the complex permeability and conductivity of layer 1, using the Inter-Meander Magnetometer in M.S. mode. |
| Step 4 | Apply layer 2 (thickness $\Delta_2$) on top of layer 1. |
| step 5 | Estimate the complex permeability and conductivity of layer 2, using the Inter-Meander Magnetometer in M.S. mode, with an EQS capacitance correction (i.e., a hybrid M.S./EQS mode). |
| step 6 | Apply layer 3 (thickness $\Delta_3$) on top of layer 2. |
| step 7 | Estimate the complex permeability, complex permittivity, and conductivity of layer 3, using the Inter-Meander Magnetometer in EQS mode, with an M.S. capacitive correction (i.e., a different hybrid M.S./EQS mode than used in step 5), or with the addition of a "push-pull" capacitive coupling drive as shown in FIGS. 15(a–b) (i.e., a third hybrid M.S./EQS mode). |
| step 8 | Apply Layer 4 (thickness $\Delta_4$) on top of layer 3. |
| step 9 | Estimate the complex permittivity of layer 4, using the Inter-Meander Magnetometer in EQS mode. |

The Inter-Meander Magnetometer is operated in EQS mode by applying a controlled voltage to the two secondaries 6, shown in FIGS. 15(a–b), which are now called the driven electrodes, and using the primary 4 as the sensing electrode. The voltage on the sensing electrode (formerly the primary winding) divided by the voltage applied to the driven electrodes (formerly the secondary windings) is now the gain of the sensor. The gain response is then used to estimate the complex dielectric properties, as in a standard interdigital-electrode-dielectrometer construct (M. C. Zaretsky, et al., Continuum Properties from Interdigital Electrode Dielectrometry, IEEE Transaction on Electrical Insulation, Volume 23, No. 6, December 1985).

TDES-based magnetometers can provide measurement of pairs of primary properties at a single temporal excitation frequency, often without calibration. The MUT 12 shown in FIG. 1 has two homogeneous layers of thickness $\Delta_1$ and $\Delta_2$, conductivity $\sigma_1$ and $\sigma_2$, and permeability $\mu_1$ and $\mu_2$. The height of the material of interest above the sensor windings is h.

In the preferred embodiments, pairs of properties can be estimated with TDES-based sensors from a single transinductance measurement at the terminals of the sensor windings. The measurement apparatus in FIG. 1 is capable of providing near-real time estimation of pairs of properties including: (1) $\sigma_1$ & $\Delta_1$, (2) $\sigma_1$ & h, (3) $\sigma_1$ & $\mu_1$, (4) $\Delta_1$ & $\mu_1$, (5) $\Delta_1$ & $\sigma_2$, (6) $\mu_1$ & h, and (7) $\mu^*_1 \mu_1 + j \mu_1''$=complex permeability. These property estimates could then be used to estimate other properties such as aging/fatigue in aluminum plates (e.g., conductivity measurement with lift-off compensation), or heat affected zone (HAZ) thickness, hardness and electrical properties.

Example measurement grids are provided later for $\sigma_1$ & $\Delta_1$, $\sigma_1$ & h, and $\mu_1$ & $\mu_1''$. Also, an example of a single property measurement of the proximity to a highly permeable media is provided, and an example of conductivity-thickness product measurement on thin conducting layers.

Design for high TDES is demonstrated to provide an order of magnitude sensitivity improvement for measurement of very small air-gap heights between the TDES-based probe and a highly permeable MUT layer. In the conductivity-thickness product measurement example, a least squares fit of the predicted continuum response to the measured response at multiple temporal excitation frequencies is used for property estimation. This least squares fit approach could be applied for single and multiple MUT property estimations in any multiple operating point measurement strategy.

Property Estimation Grid and Operating Point Response Curve Generation

Figure 3:
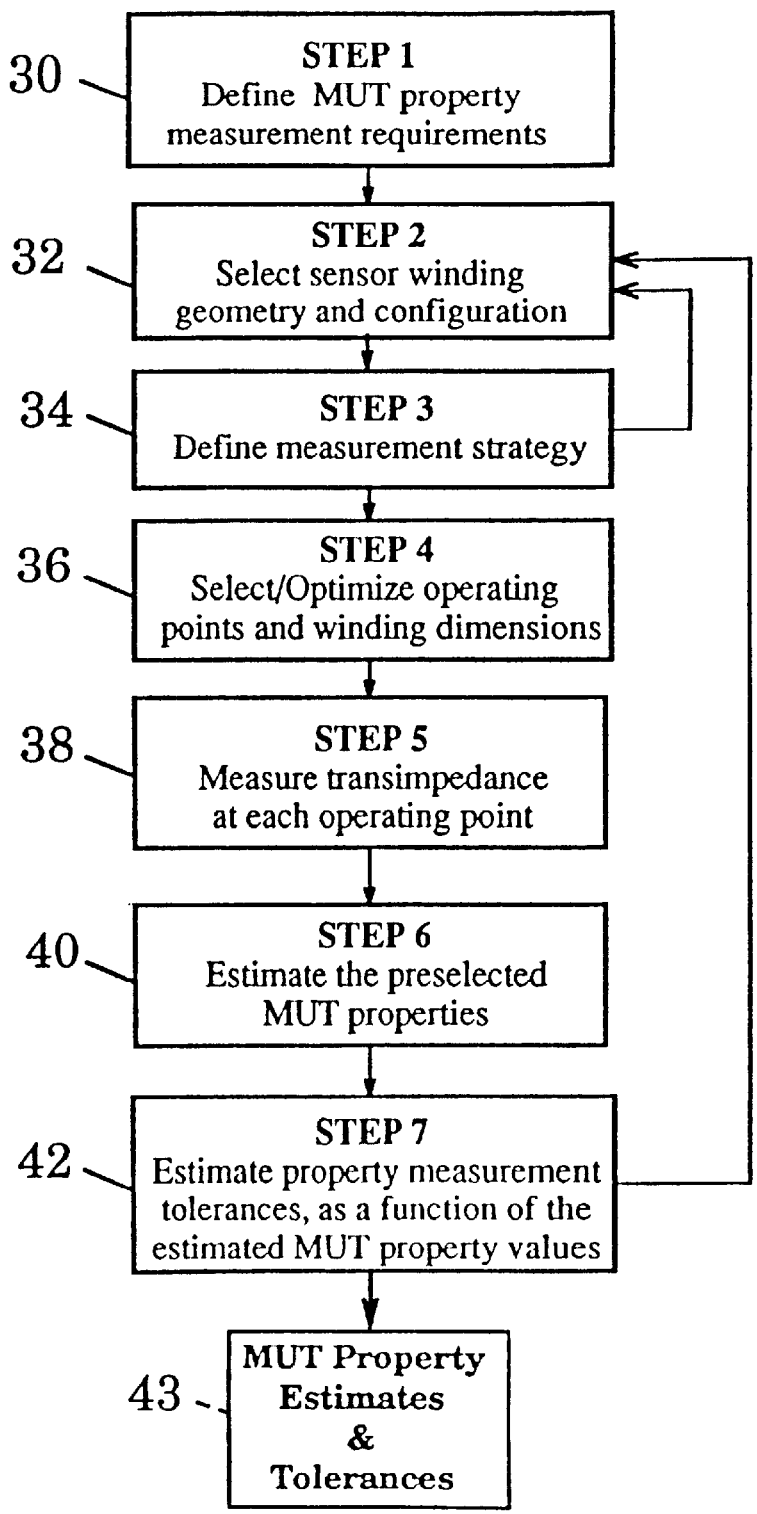
FIG. 3 is a generalized procedure flow diagram for the estimation of MUT properties and measurement tolerances according to the present invention.
Figure 4:
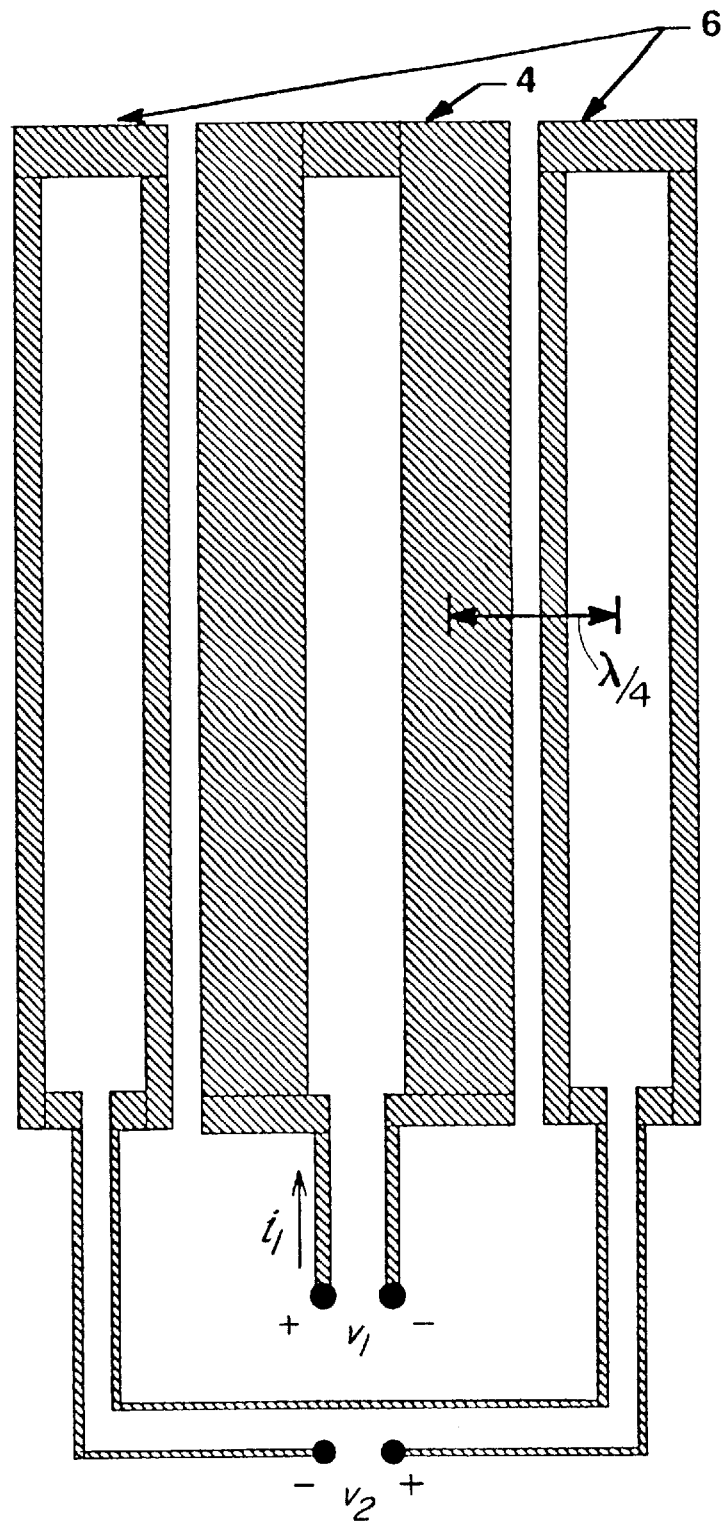
FIG. 4 is a top view of the winding geometry for an example of a single wavelength sensor construct designed to provide increased transverse diffusion effect sensitivity (TDES).

Each parameter estimation application will require a set of property estimation grids 18 and operating point response curves. The number of grids and response curves required will depend on the application. The grids and response curves have several different uses throughout the parameter estimation process. These uses include the following:

1) Develop a measurement strategy and select the measurement operating points by evaluating the MUT property estimation grids and operating point response curves, at a variety of different operating points over the required dynamic range for the MUT properties of interest (step 3: of the generalized MUT property estimation procedure in FIG. 3). Evaluating a property estimation grid includes investigating the sensitivity, selectivity and dynamic range for the MUT properties of interest. This is first accomplished by visually inspecting the grids. For example, a grid which provides a large variation in the magnitude and phase of the transinductance in response to relatively small variation in the MUT properties of interest would provide a good property estimation performance. This is discussed further in the next section, where the use of singular value decomposition is described as an automated method for identifying the "best" operating points, as well as determining the dynamic range over which sensitivity requirements can be met for measurement of specific MUT properties of interest.

2) Graphical estimation of the MUT prooerties of interest (step 6: of the generalized MUT property estimation procedure in FIG. 3). For example, in FIG. 43, the transinductance response for the Inter-Meander Magnetometer is measured for two different metal plates, one brass and one aluminum, at a variety of different unknown heights, h, above the sensor winding plane. The conductivity and height of the conducting plate are then estimated from each measurement and the conductivity of the plate is accurately determined. Alternatively, the grid is used to obtain a first guess for the conductivity and then the conductivity estimate is adjusted until the least squares error between the measured transinductance and the response for the estimated conductivity and height at each point along a line of constant conductivity is minimized. This is similar to the least squares estimation of conductivity-thickness product described in FIGS. 37(*a–b*) and 38(*a–b*) but here multiple heights are used instead of multiple temporal excitation frequencies.

3) Determination of the estimate tolerances, as a function of the estimated values for the MUT properties of interest (step 7: of the generalized MUT property estimation procedure in FIG. 3). The tolerances at a given grid point are estimated by averaging the variation in transinductance magnitude and phase between that grid point and its neighboring grid points and dividing both the average change in magnitude and the average change in phase into the corresponding change in the MUT property of interest. For example, if a change in foil thickness of 1 mm causes a phase change of 10 degrees, the sensitivity is 1 degree per 0.1 mm. If the impedance analyzer 14 can accurately measure phase to 0.1 degrees then a 0.1 degree change in transinductance phase would correspond to a 0.01 mm change in thickness. In other words the limit on the measurement precision for foil thickness for this example would be 0.01 mm (the actual tolerances will vary significantly with operating point specifications, MUT properties, and winding construct, geometry, and dimension). Also, the value of the measurement tolerance will vary with the MUT property estimate value over the dynamic range for the MUT properties of interest. The reported measurement tolerance should also include the effects of other inherent errors due to unmodelled dynamics. These errors could be determined for each sensor and model, using calibration test piece.

Figure 28A:
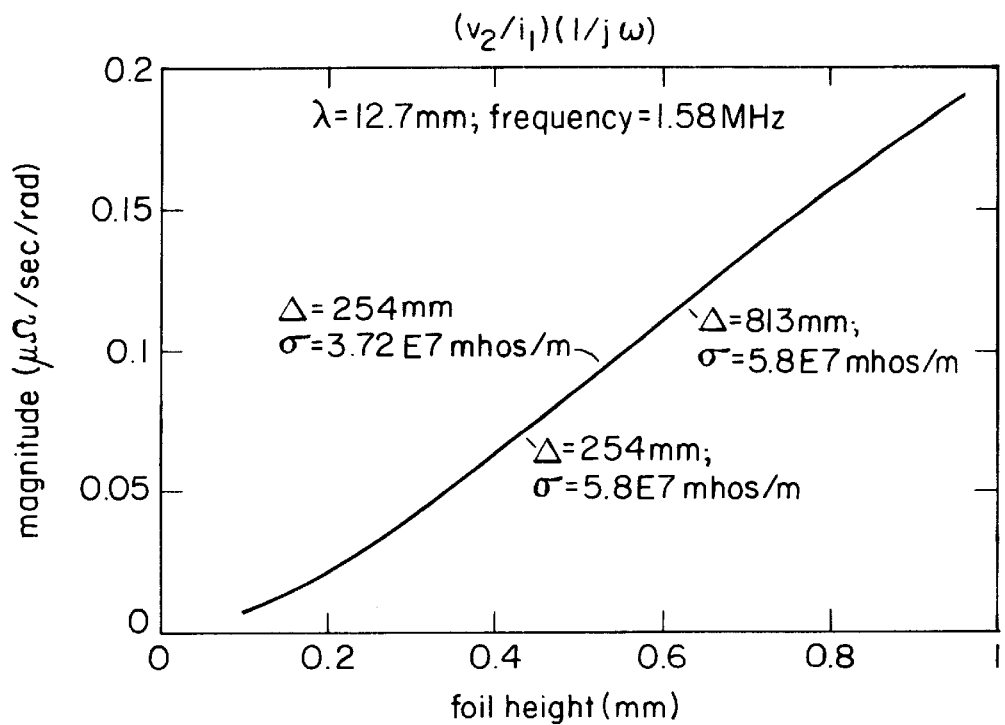
FIGS. 28(a–b) are plots of the transinductance magnitude and phase predicted by the continuum model for several different foil thicknesses and conductivities.
Figure 28B:
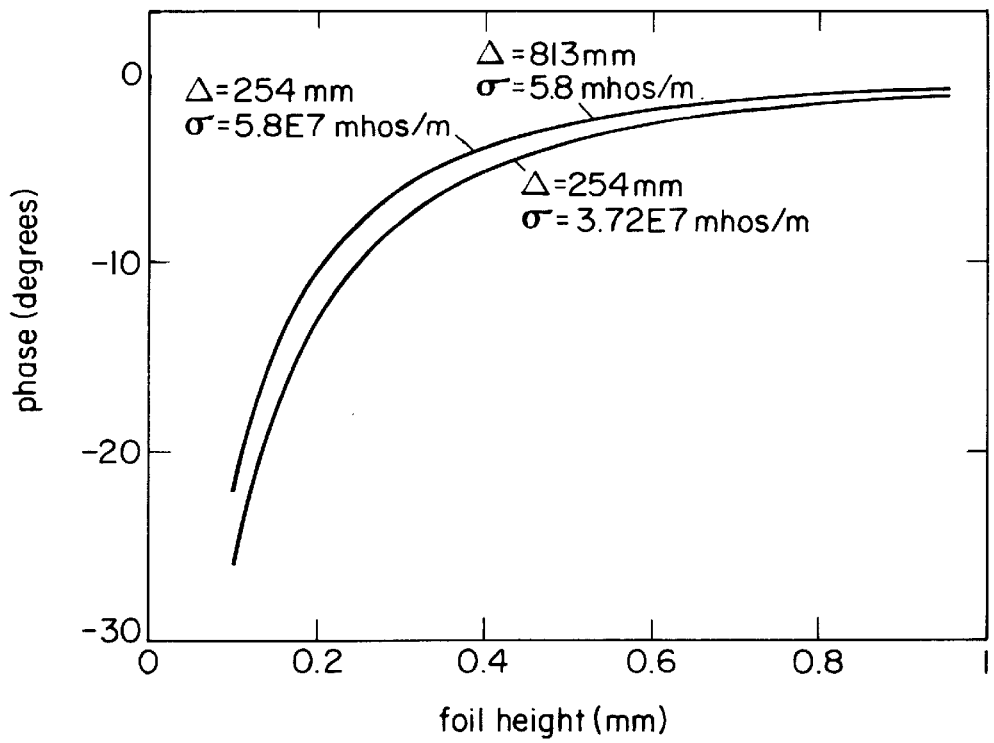

An example of an application which requires one property estimation grid and one transinductance response curve is the independent conductivity, thickness measurement demonstrated later for aluminum and copper foils. First the height of the foil, h, above the winding plane is estimated, using the magnitude and phase vs. height response curves shown in FIGS. 28(*a–b*), at a relatively high temporal excitation frequency. Then the conductivity, thickness parameter estimation grid shown in FIG. 35 for aluminum, or FIG. 36 for copper, is used to estimate the conductivity and thickness of the foils independently; at a single temporal excitation frequency.

The application described above has three unknowns, the air-gap height, h, the layer conductivity, $\sigma$, and the layer thickness, $\Delta$. The use of additional parameter estimation grids at different operating points (e.g., at multiple heights) would improve the measurement tolerances by averaging out the contribution of random errors and providing additional information to build confidence in the MUT property estimates. Property estimation problems requiring three or more MUT property estimates will always require more than one estimation grid or at least one additional operating point response curve, (e.g., in the case of three properties, at least one grid and one additional response curve is required).

Figure 18:
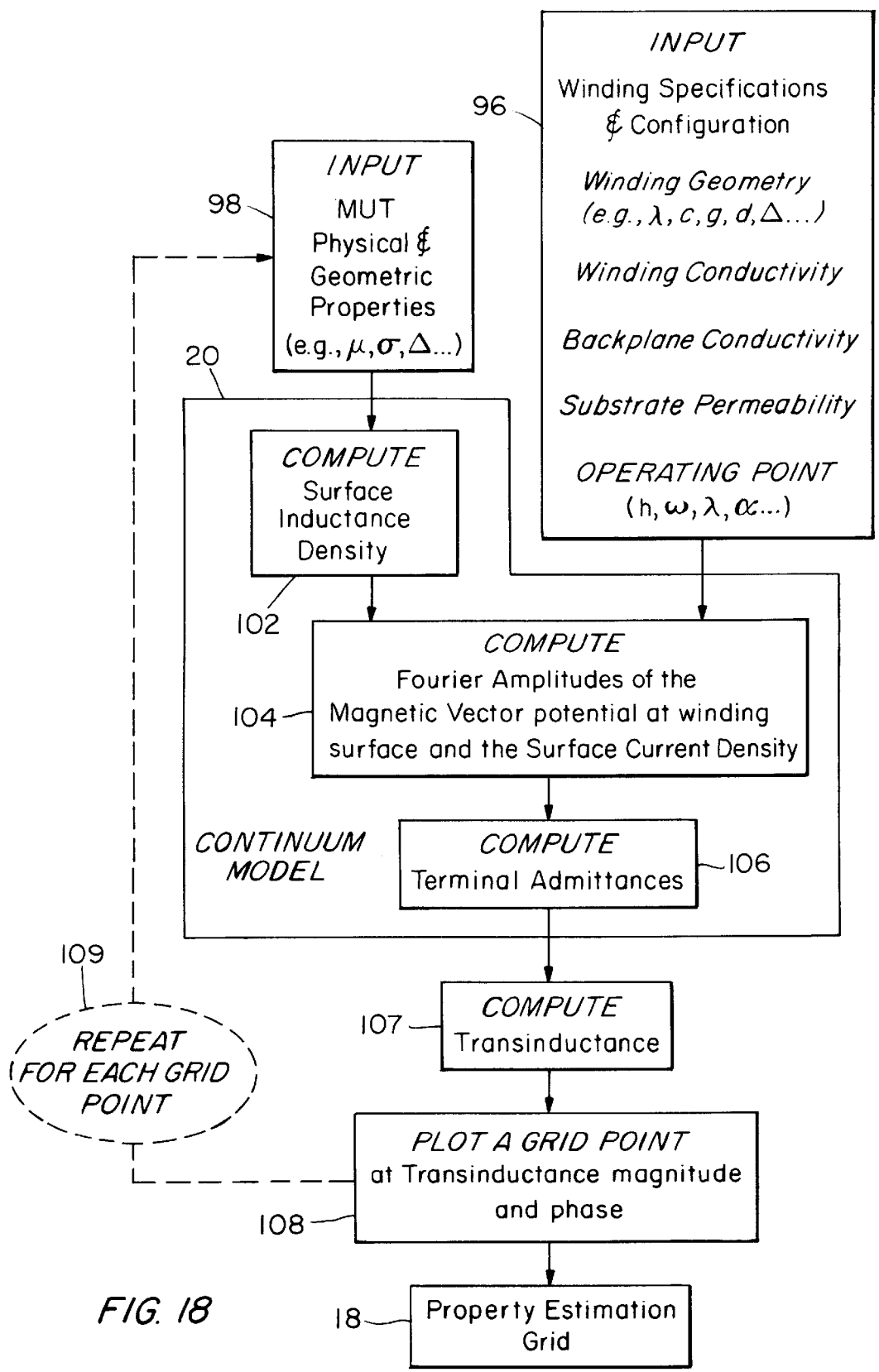
FIG. 18 is a flow diagram of the generation of a property estimation grid using a continuum model according to the invention.

FIG. 18 provides a flow diagram describing the generation of a property estimation grid 18, using a continuum model 20. The same concepts described in this figure apply to the generation of operating point response curves. The only difference is that for property estimation grids the main loop is repeated for different MUT property pairs (e.g., conductivity & thickness, or conductivity & proximity), while for the generation of operating point response curves one operating point parameter is varied over a range of interest (i.e., an operating point response curve is generated by computing the transinductance response for each incremented value of one operating point parameter, with all other operating point parameters held constant). An operating point response curve is a one dimensional grid, where the variable is an adjustable operating point parameter (e.g., height, frequency, wavelength) instead of a preselected MUT property.

The air-gap height, h, is generally considered an operating point parameter. However, in many applications it is more convenient to consider the air-gap height as an MUT property of interest (e.g., the conductivity & height grid in FIG. 43 treats the air-gap height as an MUT property and includes it as one of the two dimensions in the property estimation grid).

To generate a property estimation grid, first input at 96 the winding specifications and configuration, including the winding geometry, conductivity, back-plane conductivity and proximity, and substrate permeability. Also, input at 98 the operating point parameter set (i.e., h, ω, λ, α, $x_s$, $y_s$). A continuum model 20 is then used to compute the terminal relations at 106 for the first MUT property pair. The continuum model for the Inter-Meander Magnetometer is described in detail later. The terminal relations are translated into transinductance at 107. To generate the complete property estimation grid for two MUT properties of interest (e.g. conductivity & thickness of a conducting layer), these properties are varied over the dynamic range of interest at 109. The continuum model is then used to compute the terminal relations for each new MUT property pair, and each new grid point is plotted at 108, until the property estimation grid 18 is complete for the dynamic range of interest.

A similar approach could be used to generate a property estimation grid when an accurate continuum model is not available. This would require the use of calibration test pieces with a variety of different property pairs covering the MUT property range of interest.

Sensor Design and Operating Point Selection/Optimization

Singular value decomposition can be used for many aspects of sensor design and operating point selection/optimization. The distinction between selection and optimization is made here. Applications requiring the estimation of more than two MUT properties of interest would require significantly more work to identify the optimal operating points and optimal sensor construct, geometry, and dimensions than is required to select a sensor design and operating point which achieves the desired measurement performance for a specific application but is not optimal. Thus, identification and selection of operating points and sensor designs which provide the desired performance does not require optimization.

Singular value decomposition is described in detail in later sections for specific examples including (1) the independent measurement of conductivity and thickness for metal foils, (2) the independent measurement of conductivity and air-gap height for metal plates, and (3) the measurement of air-gap height relative to a highly permeable media.

Figure 19:
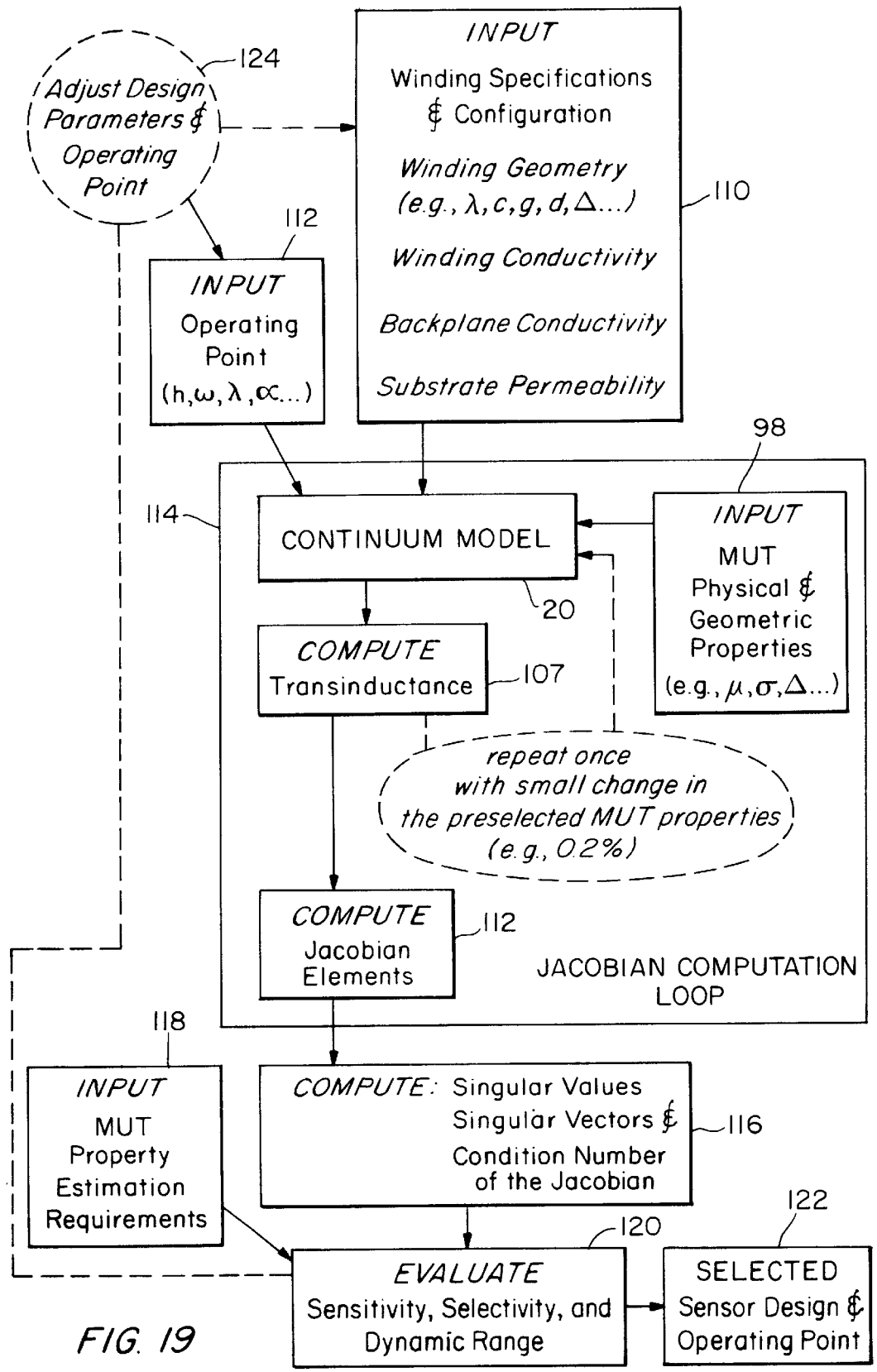
FIG. 19 is a flow diagram of the evaluation and selection of a sensor design and operating point parameter set, using singular value decomposition of a Jacobian relating variations in the design or operating point parameters to variations in the winding terminal measurements according to the invention.

FIG. 19 provides a basic flow diagram for optimization of sensitivity, selectivity and dynamic range using singular value decomposition on the Jacobian relating perturbations in the MUT properties of interest to changes in the value of the terminal relation measurements at the sensor windings. The following represents a subset of the possible uses for the optimization method described in the flow diagram.

Figure 33A:
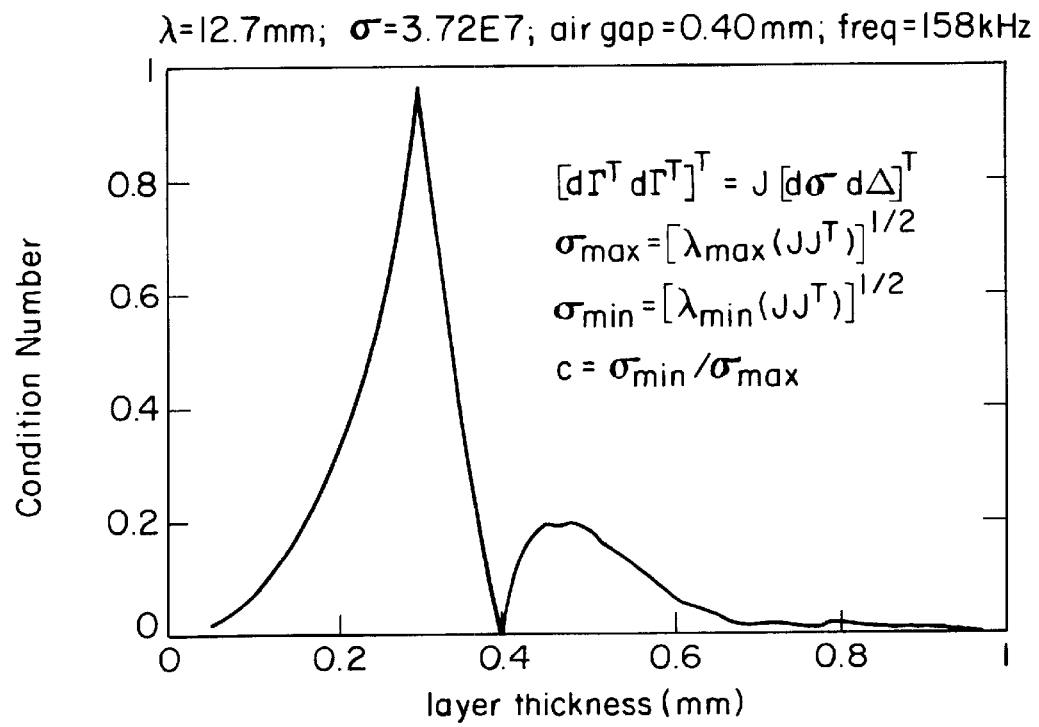
FIGS. 33(a–b) are plots of the condition number, singular values, and singular vectors of the Jacobian for measurement of conductivity and thickness for a material layer with conductivity of 3.72E7 mhos/m (similar to that of aluminum).
Figure 33B:
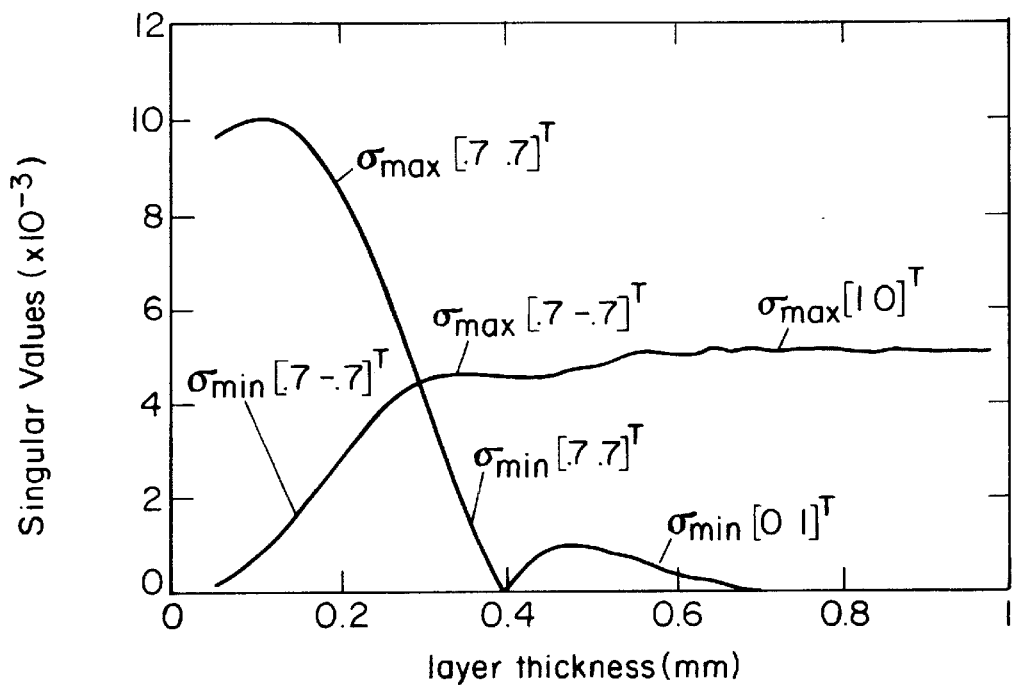
Figure 34A:
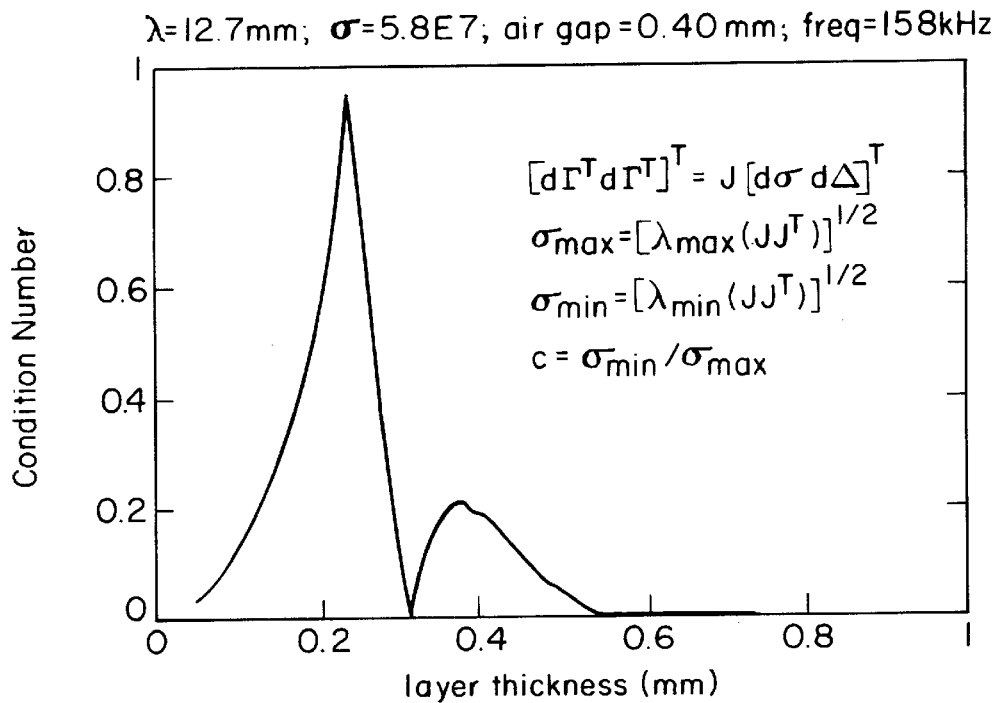
FIGS. 34(a–b) are plots of the condition number, singular values, and singular vectors of the Jacobian for measurement of conductivity and thickness for a material layer with conductivity of 5.8E7 mhos/m (similar to that of copper).
Figure 34B:
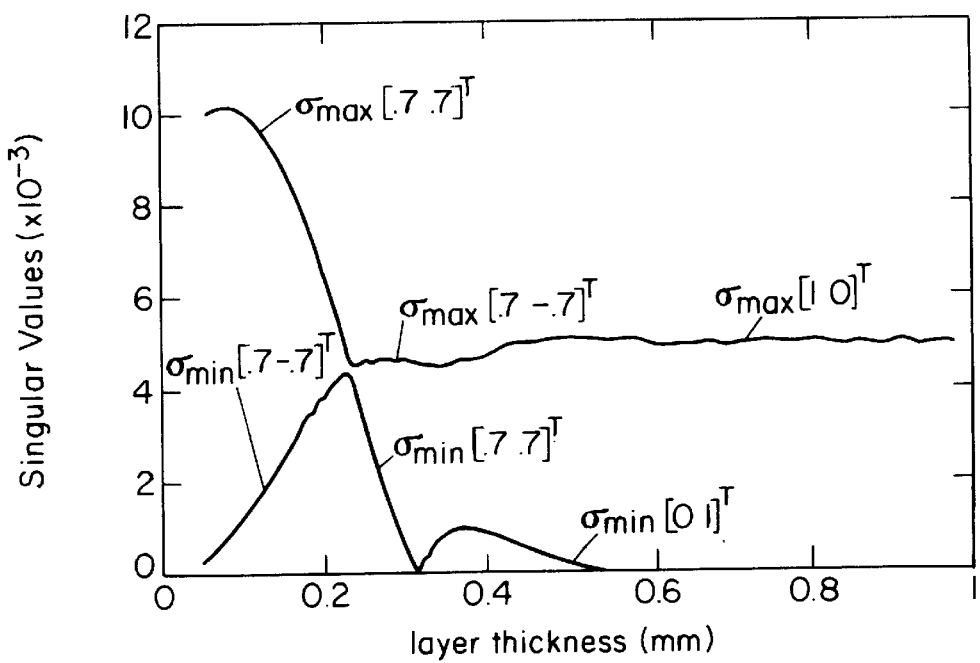

1) Determine the dynamic range over which the required measurement tolerances can be met for a specific MUT property of interest: An example of this usage is demonstrated in FIGS. 33(a–b) and 34(a–b), where the dynamic range for independent estimation of conductivity and thickness is determined for metal foils. This range is limited by the value of the condition number. For an aluminum layer thickness below 0.1 mm for the Inter-Meander Magnetometer geometry and dimension given in the example, only the conductivity-thickness product can be accurately measured. For layer thicknesses between 0.1 mm and 0.375 mm, independent estimation of conductivity and thickness is easily demonstrated for an aluminum foil as shown in FIGS. 33(a–b). For a copper foil the dynamic range for independent estimation of conductivity and thickness is 0.05 mm to 0.275 mm as shown in FIGS. 34(a–b). For aluminum and copper layers thicker than 0.65 mm only the conductivity can be measured, because the transinductance magnitude and phase are not sensitive to changes in the layer thickness for layers much thicker than the characteristic decay length of the magnetic fields into the layer (often called the depth of penetration). For this example, the dynamic range was determined for a specific set of operating point parameters (λ=12.7 mm, h=0.4 mm, f=158 kHz, σ=3.72E7 mhos/m for aluminum, σ=5.8E7 mhos/m for copper). High selectivity for measurement of conductivity and thickness (i.e., a high condition number) exists for an aluminum layer thicknesses of 0.3 mm, this thickness for copper however results in very poor selectivity, as shown in FIGS. 33(a–b) and 34(a–b). Thus, careful selection of operating points and winding geometry is necessary, because in many applications the dynamic range for high sensitivity to one MUT property of interest (e.g. thickness) will depend on the value of a second MUT property of interest (e.g., conductivity) as in the described examples for copper and aluminum foils.)

Figure 40:
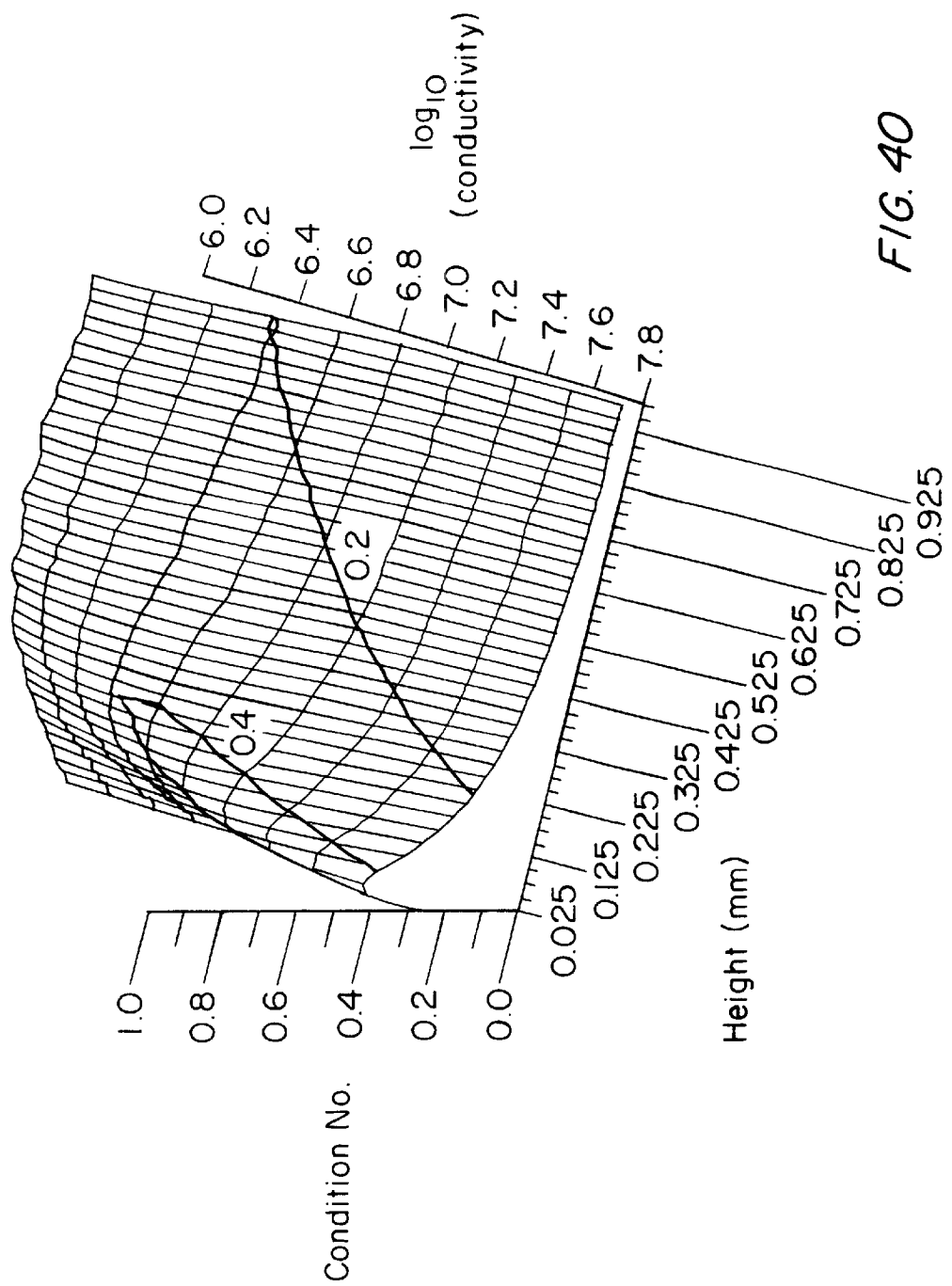
FIG. 40 is a plot of the condition number for the Jacobian for measurement of conductivity and height for a metal plate above the winding plane, as predicted with the continuum model for the Inter-Meander Magnetometer as a function of the height and log(conductivity).
Figure 41A:
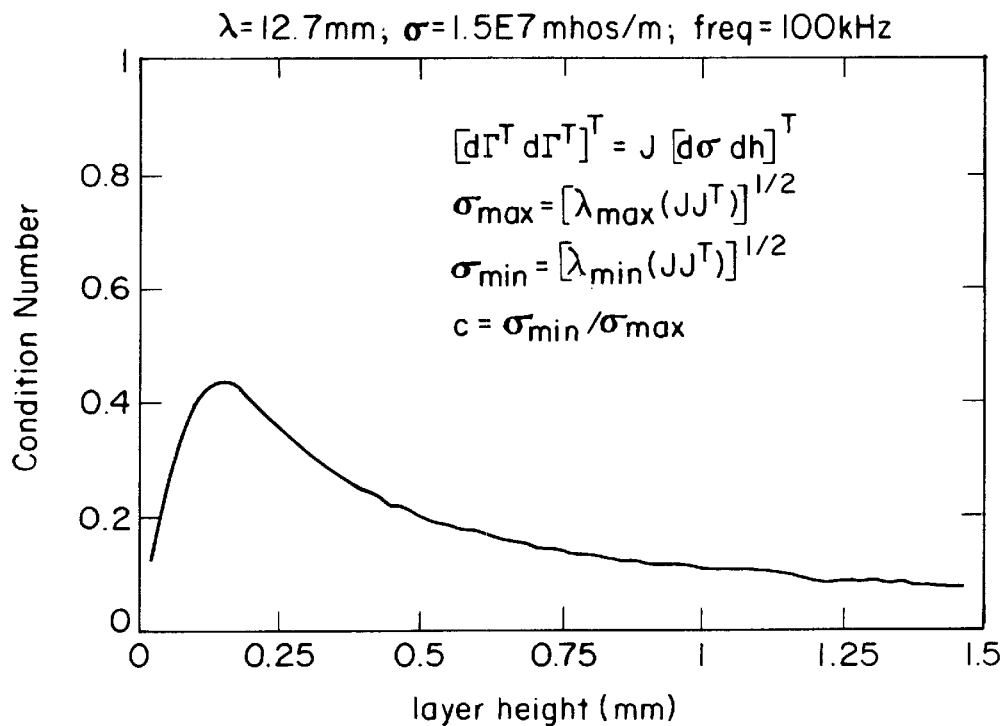
FIGS. 41(a–b) are plots of the condition number, singular values, and singular vectors of the Jacobian for measurement of conductivity and height of a metal plate above the winding plane as a function of the plate height.
Figure 41B:
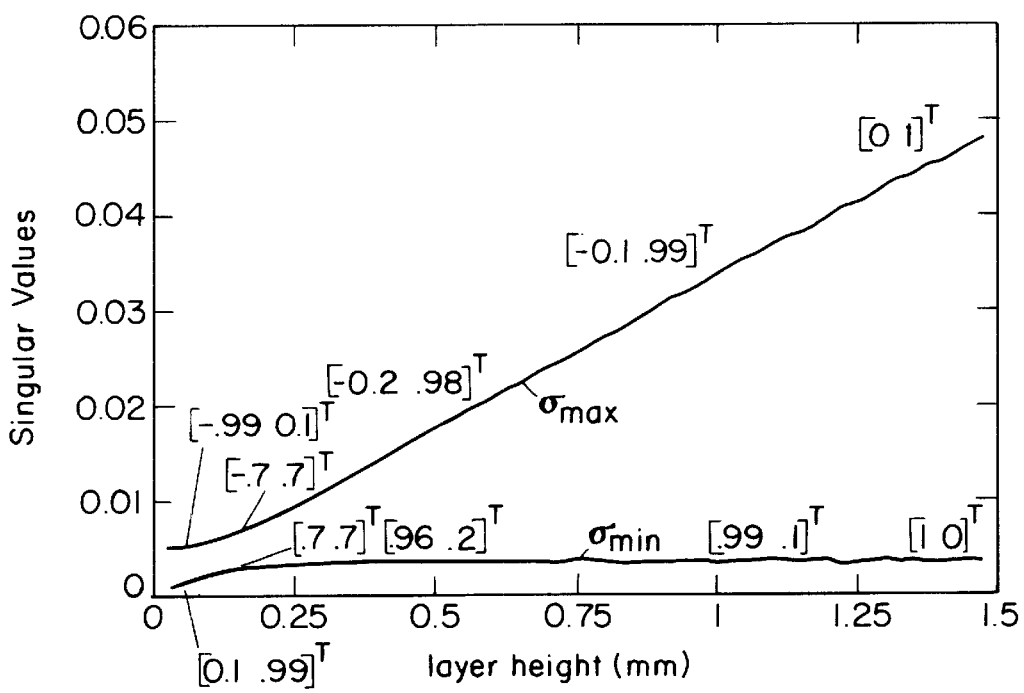
Figure 42A:
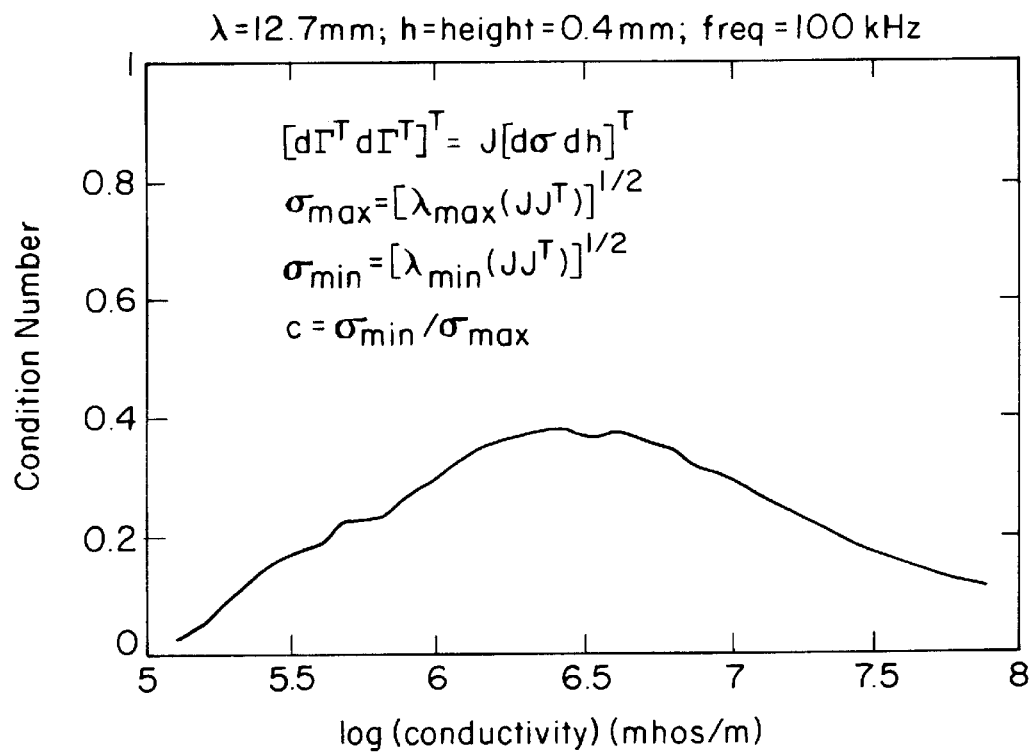
FIGS. 42(a–b) are plots of the condition number, singular values, and singular vectors of the Jacobian for measurement of conductivity and height of a metal plate above the winding plane as a function of log(conductivity) for the plate.
Figure 42B:
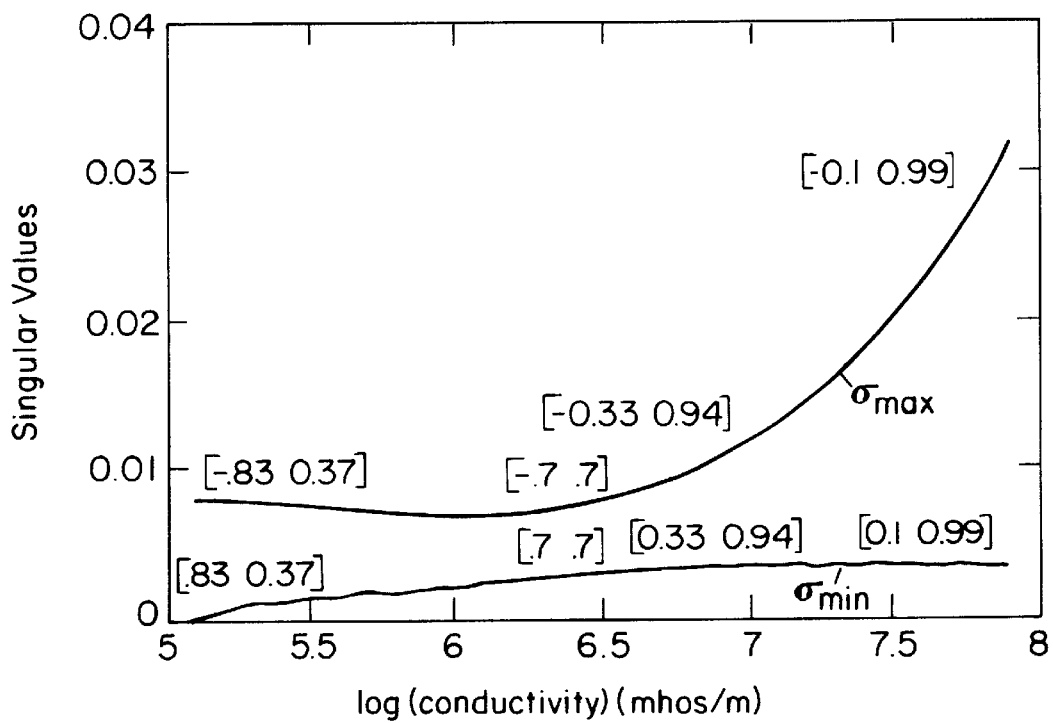

2) Determine the optimal operating point parameter values for a specific measurement application: The operating point parameters include the air-gap height, h=$x_s$, the temporal excitation frequency, f, the defined spatial wavelength of the sensor winding construct, λ, the position and orientation of the sensor relative to the MUT ($x_s$, $y_s$, α) and any other adjustable parameters including the dimensions of the sensor windings. For a given set of operating point parameters there is an associated sensitivity, selectivity and dynamic range for an MUT property of interest. For example, suppose the measurement objective is to estimate the conductivity of a metal plate. Suppose that the air-gap between the sensor winding plane and the metal plate surface can be adjusted but can not be accurately controlled (e.g., suppose in-situ measurements on a complex shaped aircraft engine part were required). Then the measurement requirements include the independent estimation of the conductivity and air-gap height. First, a temporal excitation frequency and defined spatial wavelength are selected to provide significant sensitivity to the properties of interest (this step is not demonstrated; however, singular value decomposition could also be used for this step with all other parameters held constant by choosing f and λ which provide a relatively high condition number). Then the condition number, singular values, and singular vectors are computed for the Jacobian relating changes in conductivity and air-gap height to changes in the trans-inductance magnitude and phase. The results for a specific example are shown in FIGS. 40, 41(*a–b*) and 42(*a–b*). Since control of the conductivity is not possible, the air-gap height is adjusted to provide a high condition number and relatively high singular values. Care must be taken in interpreting the singular values and vectors in this problem, since the maximum singular vector rotates almost 180 degrees over the range of air-gap height variation shown in FIGS. 41(*a–b*). Furthermore, in this example it is desirable, but not necessary, to make multiple measurements at multiple heights to improve the confidence in the conductivity estimates.

Figure 44:
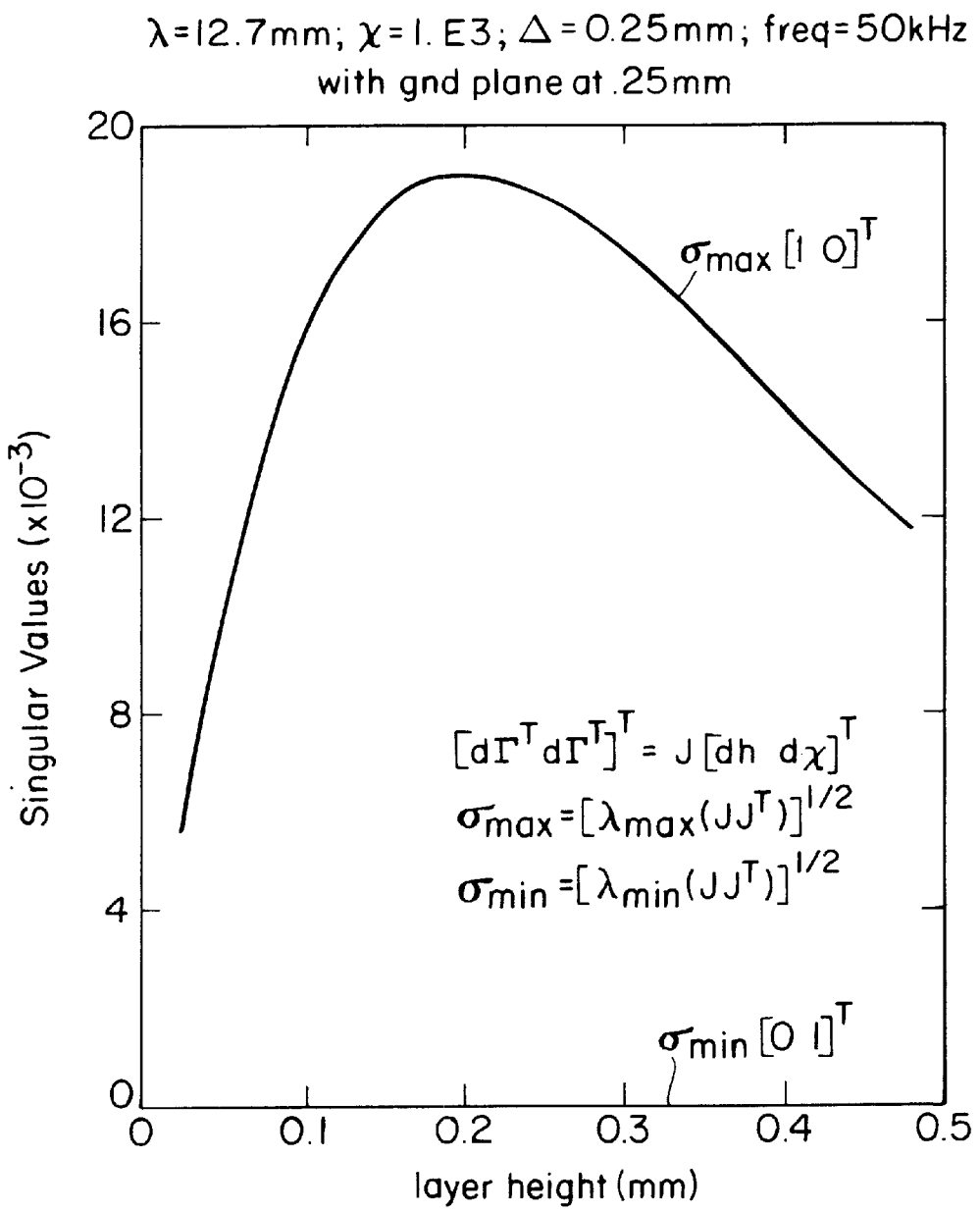
FIG. 44 is a plot of the maximum and minimum singular values and right singular vectors of the Jacobian for measurement of permeability and height of a high permeability layer.

Another example of optimal air-gap height determination is provided in FIG. 44 for proximity measurement relative to a highly magnetic media. The objective might be to measure small variations in proximity. In this example, the dynamic range of high sensitivity proximity measurement, with temporal excitation frequency at 50 kHz, is from 0.05 mm to 0.7 mm. This range would vary with temporal excitation frequency, as well as with other adjustable operating point parameters.

Figure 45A:
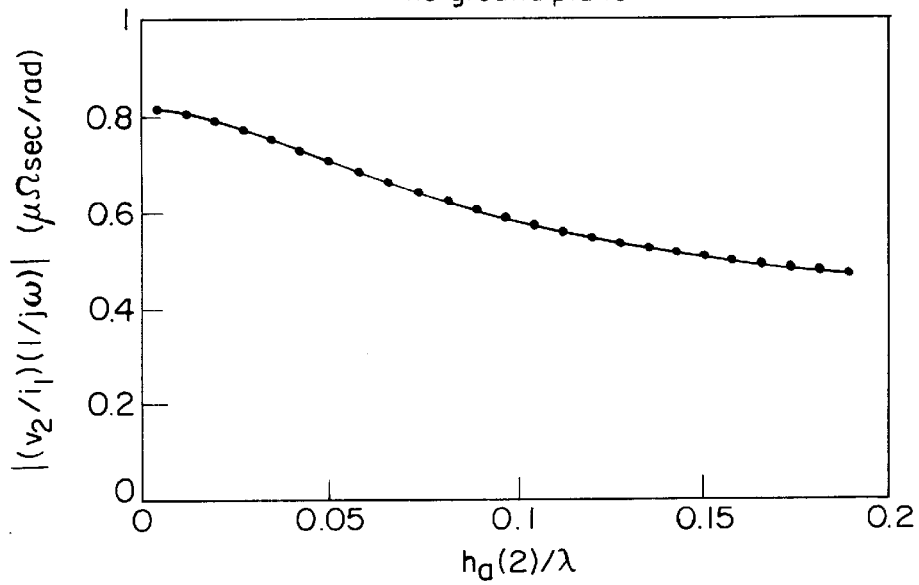
FIGS. 45(a–b) are plots of the transinductance magnitude variation with the height of a high permeability layer above the Inter-Meander Magnetometer simulated with the continuum model, (a) with no back-plane, and (b) with a back-plane at 0.5 mm below the winding plane.
Figure 45B:
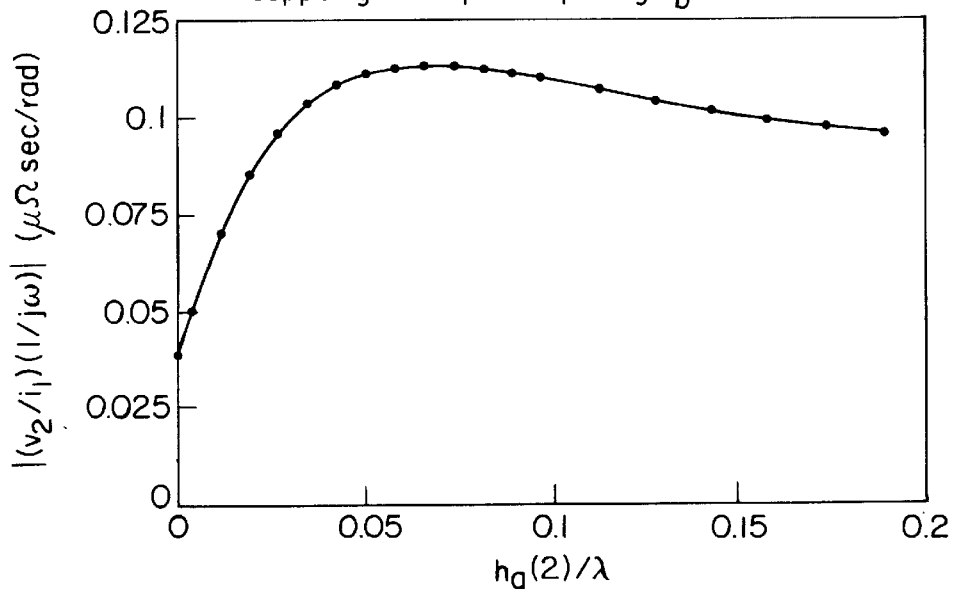

3) Determine the optimal sensor winding geometry and construct: Singular value decomposition and the procedure flow described in FIG. 19 can also be used to determine the optimal sensor winding geometry, configuration, and dimensions. For example, the optimal location of a conducting back-plane might be determined by maximizing the sensitivity to the proximity of the sensor to a magnetic media. FIGS. 45*a* and 45*b* indicate the dramatic effect on sensitivity when a back-plane (also called a ground plane) is included. The optimal position of this back-plane could be determined by plotting the maximum singular value as a function of the back-plane proximity to the winding plane. The optimal back-plane position would occur at the peak in the singular value plot. Similarly, the dimensions of the windings (e.g., the width of the primary c, and secondary d, and the defined spatial wavelength, $\lambda$) might be optimized in this manner.

The flow diagram in FIG. 19 describes the general procedure for computing the singular values, singular vectors, and condition number and for selecting or optimizing the sensor design or operating point parameters. This can be accomplished by plotting the singular values, singular vectors, and condition number over a wide range of sensor and operating point parameter values and selecting the parameter values that provide the best performance, or by continually adjusting these parameters until a set of parameters provides performance which meets or surpasses the measurement requirements.

First, the winding specifications and configuration are input at 110 and then the operating point parameters are input to the continuum model 20. Then the elements of the Jacobian relating the variations in two or more MUT properties (e.g., conductivity & thickness of a conducting layer) of interest to variation in the terminal relations (e.g., transinductance magnitude and phase) are computed in the Jacobian computation loop at 114. Singular value decomposition is then performed at 116 on this Jacobian to obtain the singular values, singular vectors and the condition number. These are then evaluated at 120 to determine the sensitivity, selectivity and dynamic range for the MUT properties of interest and compared to the MUT property estimation requirements input at 118 for the preselected MUT properties of interest. If the property estimation requirements are not met the process is repeated by adjusting at 124 the sensor 110 and/or operating point parameters 112 until the property estimation requirements 118 are achieved.

Inter-Meander Magnetometer Design

The Inter-Meander Magnetometer structure described below is one possible configuration for a magnetoquasistatic imposed $\omega$-k sensor. The design of this sensor is ideal for investigative research purposes. The sensor construct was intentionally configured to provide the symmetry necessary to permit accurate response prediction using modeling techniques that provide substantial advantages for development of physical understanding of underlying phenomenology.

Figures 20, 21:
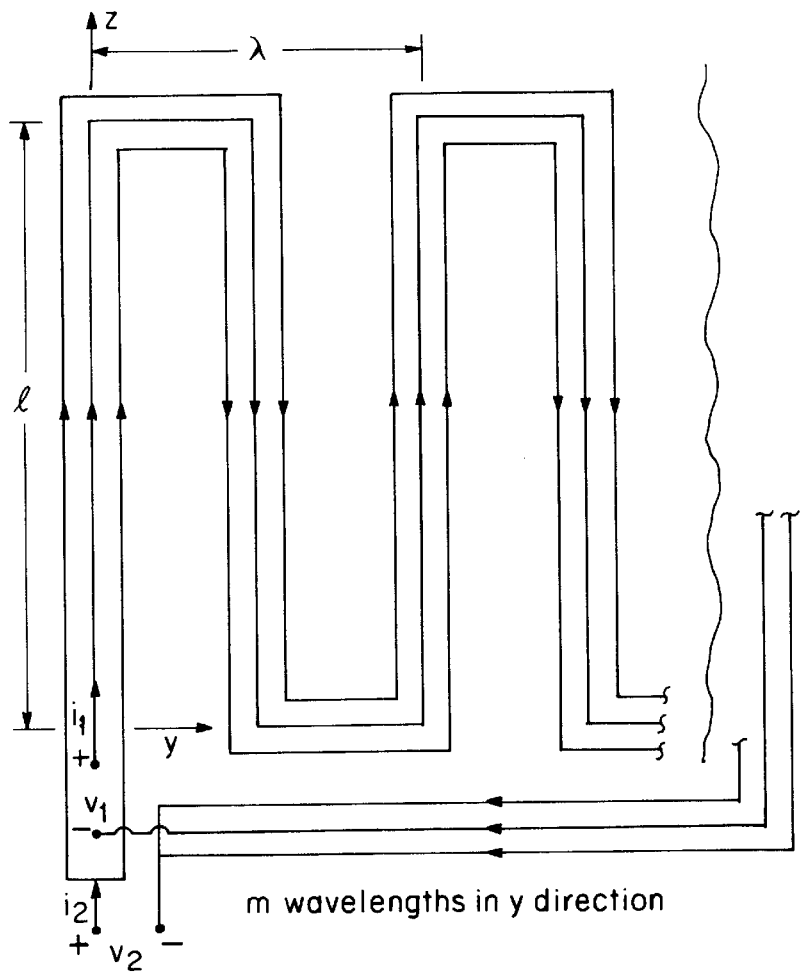
FIG. 20 is a schematic top view of another example of a winding construct for a meandering array that applies a magnetic potential to the MUT with several cycles of the same spatial wavelength.
FIG. 21 is a table of two example winding dimensions and physical properties for the Inter-Meander Magnetometer which produce significant TDES near the TDECF.

The proposed sensor is fabricated with "meandering" conductors confined to a single surface. The resulting periodic structure forms a transformer in the plane x=0, as shown in FIGS. 10 and 20. The actual mask used to fabricate the Inter-Meander magnetometer used in the experiments is shown to scale in FIG. 10. The primary of the sensor has the terminals ($i_1$, $v_1$) and could be driven by an input current or voltage source. The secondary consists of a pair of conductors that meander to either side of the primary. The terminals of this pair of windings are connected in parallel so that their voltage, $v_2$, will reflect the flux produced by the driven winding. The return paths for the pair of secondary conductors are arranged, in FIG. 10, so that each conductor will link flux over areas of the same size. The open circuit voltage or the current through a prescribed load at the secondary terminals could be the sensor output. This structure is represented in cross section in FIG. 24(*a*), where what are shown as "wires" in FIG. 20 are now shown to have widths c and d for the primary and secondary conductors, respectively. There are m wavelengths, $\lambda$, to the structure and the length, l, is large enough compared to $\lambda$ so that the fields can be regarded as two dimensional.

Optimization of Measurement Performance

The approach developed for optimization of property measurement performance for the Inter-meander Magnetometer is based on well understood techniques in linear algebra. A typical application might involve the measurement of a layer of a higher conductivity alloy that has formed on a metallic substrate during processing. The objective might be to monitor the thickness and conductivity of this layer at various stages in processing to maintain desired product quality.

A quantitative technique that permits the identification of regions of optimal measurement performance within the parameter space of interest is required. In the above example, the parameter space will be quite nonlinear and is bounded by the estimated range of possible layer thickness and conductivity. The measurement performance can be characterized by the following performance specifications:

i) Performance bandwidth—range of frequencies over which accurate, uncalibrated, absolute measurement is possible with available instrumentation (ii) Dynamic range—range of properties over which accurate parameter estimates can be obtained.

(iii) Sensitivity—variation in output signal produced by a variation in the measured property (iv) Robustness—a measure of the ability to obtain accurate measurements at the limits of the sensor bandwidth and dynamic range.

(v) Selectivity—a measure of the ability to differentiate between (1) the effects of two or more physical or geometric properties of interest (this definition is used throughout this document) (2) the effects of the estimated parameter and other modeled effects, (3) the desired signal and disturbances of other frequencies or phases, (4) the desired signal and noise (signal-to-noise ratio), (5) the desired signal and the effects of unmodeled dynamics.

(vi) Threshold level-the minimum output signal level required for accurate measurement of output magnitude and phase.

A typical measurement optimization procedure would follow the general procedure described below:

(1) Use the continuum model to numerically compute elements of the Jacobian relating differential variations in the vector of unknown quantities (e.g., conductivity and thickness of a metal foil) to the vector of measured quantities (e.g., the Inter-Meander Magnetometer Transimpedance, $v_2/i_1$, magnitude and phase)

(2) Determine the singular values and associated right singular vectors using Singular Value Decomposition for the Jacobian formulated in (1).

(3) Select the optimal frequency for the primary excitation and determine the performance bandwidth for an operating point at the center of the bounded parameter space for the application under consideration (4) Determine the dynamic range by establishing the minimum acceptable selectivity, which relates to the condition number (=minimum singular value/maximum singular value), and the minimum sensitivity determined by the magnitude of the minimum relevant singular value (5) Evaluate robustness by comparing the dynamic range to the application parameter space of interest, and by evaluating the relative observability for specific modes associated with the right singular vectors (6) Confirm performance potential through proof of concept measurements and tune sensor geometry and geometric construct parameters if required.

Continuum Modeling

In the continuum models, two regimes of behavior are considered. In the first regime, the frequency ranges from low frequencies (currents are uniform with respect to the x and y directions throughout the conductors) to frequencies beyond the TDECF. In this range, span-wise diffusion is accounted for in the conducting windings, along the y direction, up until the currents in the conductors can no longer be assumed uniform with respect to the x direction (i.e., $\Delta<\delta$=skin depth=SQRT($2/\omega\mu\sigma$), where $\Delta$ is the thickness of the conductors in the x direction, $\omega$ is the angular excitation frequency, and $\mu$ and $\sigma$ are the effective permeability and conductivity). In the second regime, the frequency is assumed high enough that the magnetic vector potential can be approximated as constant, with respect to y, along the surface of the conducting windings.

The media above and below the windings are represented by surface inductance densities, $L_n$, which relate the Fourier amplitudes of the magnetic vector potential $A_n$, to the Fourier amplitudes of magnetic field intensity, $H_{yn}$, in the planes just above (a) and below (b) the windings.

The preliminary objective is to predict the response of any particular circuit connected to the secondary for any excitation on the primary, with various neighboring media. This requires a detailed description of the windings that can be used with subroutines describing any particular neighboring media. A schematic representation of the response prediction algorithms is provided in FIG. 22.

Figure 23:
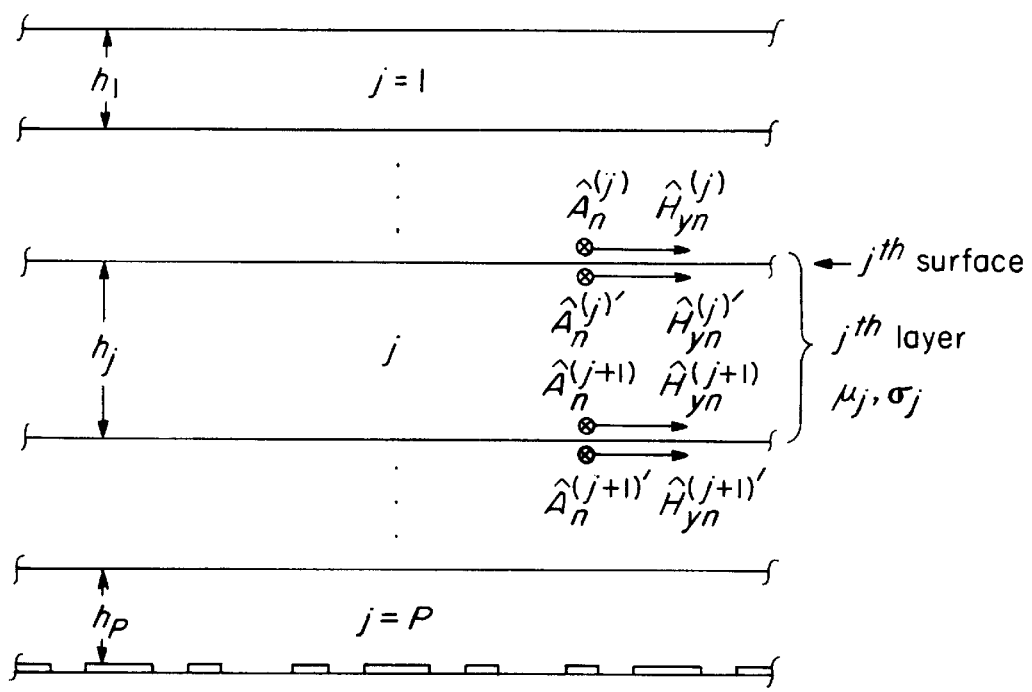
FIG. 23 is a side-view of a material under test with P layers above the sensor winding plane.
Figure 25A:
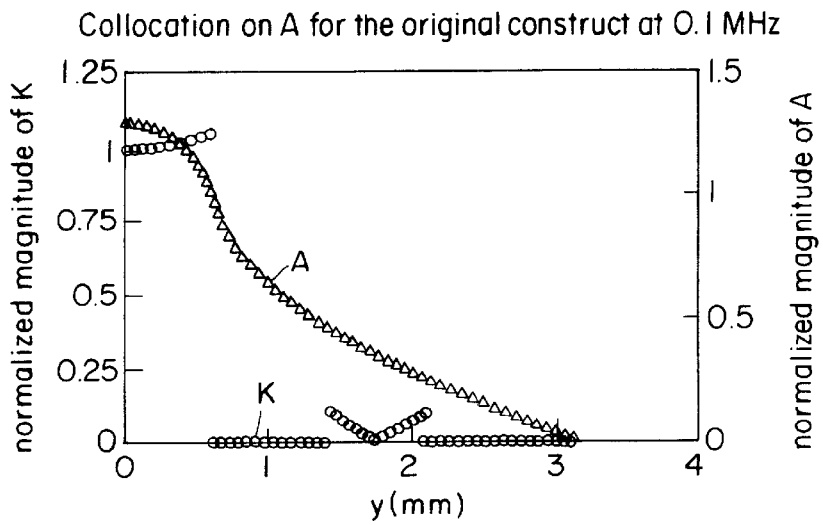
FIGS. 25(a–f) are a set of plots of the surface current density distribution, o, and the magnetic vector potential distribution, $\Delta$, over the first quarter wavelength of an Inter-Meander Magnetometer with the original construct, as predicted by the continuum model, at three different temporal excitation frequencies for the collocation on K approach in FIGS. 25(d–f) and for the collocation on A approach in FIGS. 25(a–c).
Figure 25B:
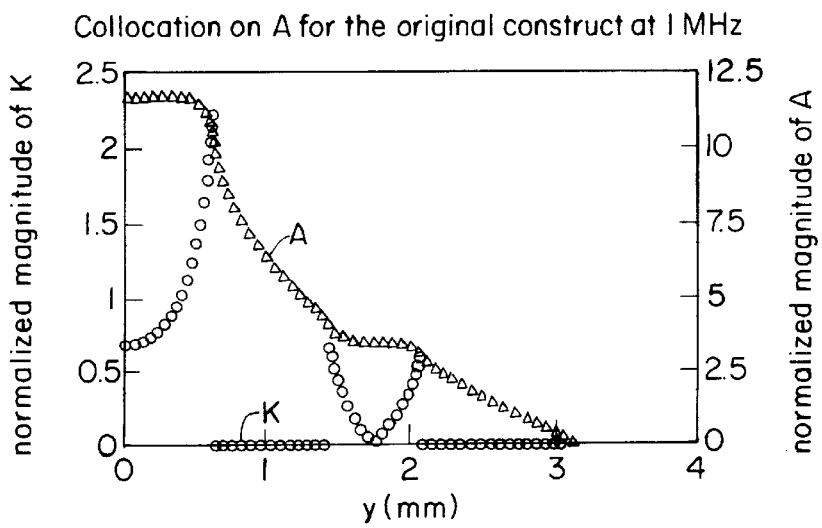
Figure 25C:
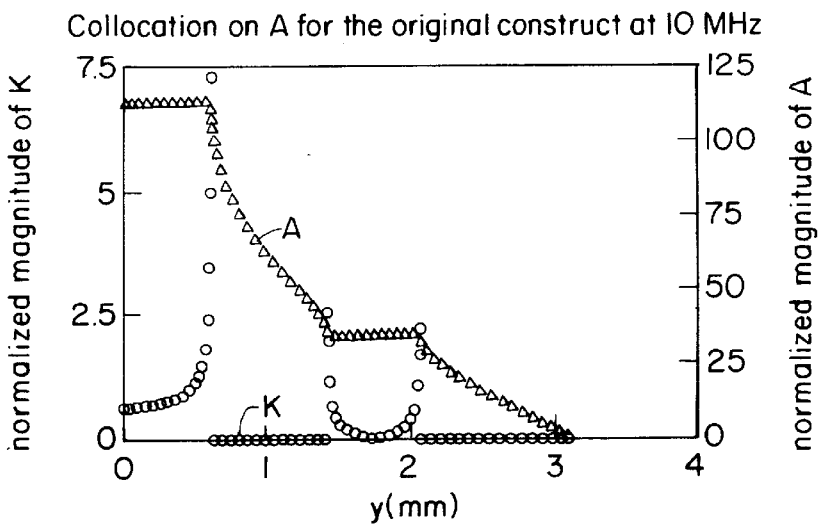
Figure 25D:
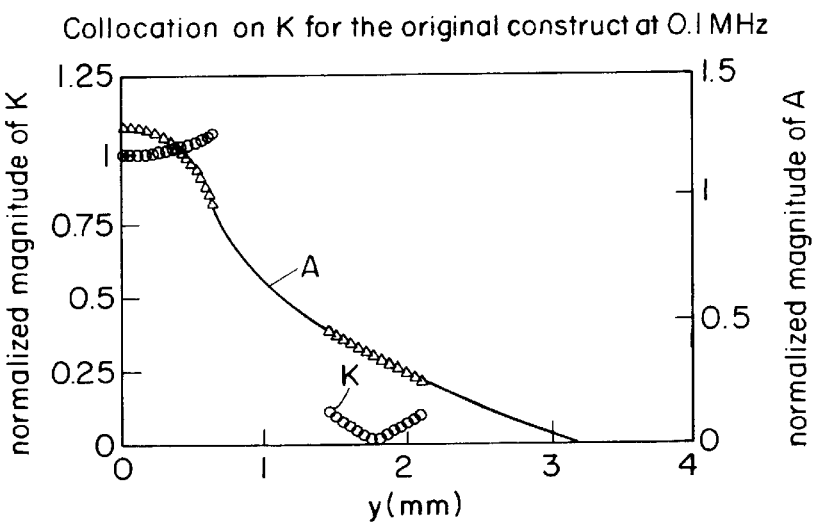
Figure 25E:
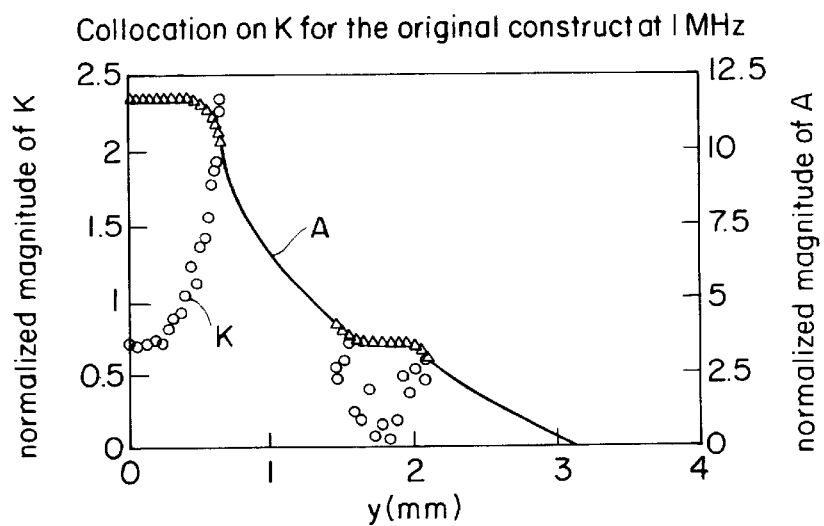
Figure 25F:
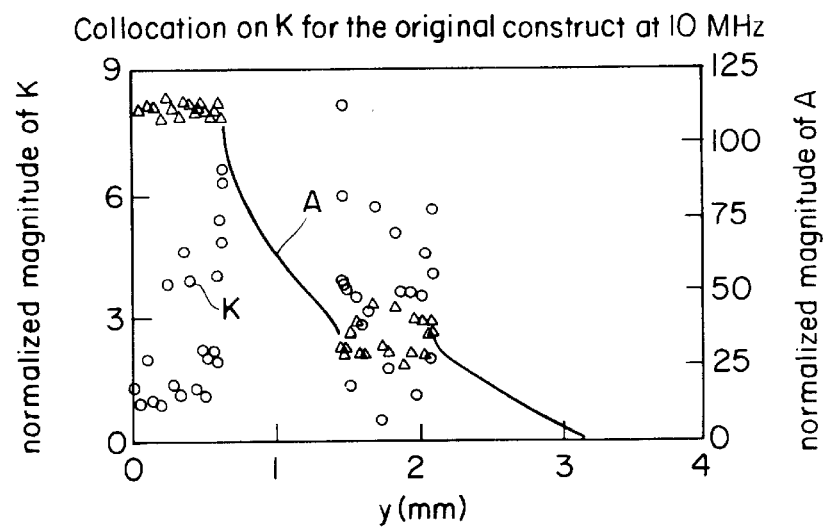

The neighboring media is represented as a multi-layered structure of P homogeneous layers above and/or below the winding plane, as shown in FIG. 23. Representation of distributed properties can be achieved by introducing a large number of thin layers.

This approach permits a complete analytical solution for the field distributions in the direction perpendicular to the winding plane. A numerical solution using the subdomain method of weighted residuals (B. A. Finlayson, "The Method of Weighted Residuals and Variational Principles", Academic Press, N.Y., (1972)) is then introduced to incorporate the winding geometry, other relevant dynamics, and boundary conditions in the winding plane.

First, the specification of the meandering array 126 and the specifications of the MUT 128 are input to the continuum model 20. Then the collocation current densities, $\hat{K}_n$, and vector potentials, $\hat{A}_n$, are computed 130. The modeling effort is carried out in the following steps: (1) Fourier amplitudes are determined in terms of collocation current densities or vector potentials, (2) flux continuity and Ampere's continuity condition are introduced, (3) Faraday's law is evaluated to obtain the collocation conditions and subdomain integrals, and (4) equivalent circuit admittances are derived.

Figure 22:
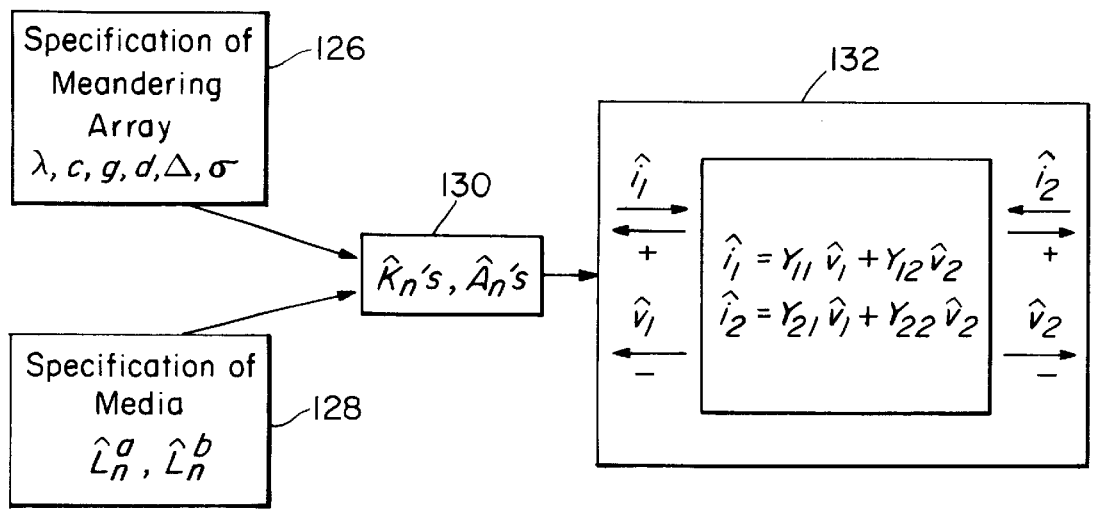
FIG. 22 is a flow diagram of the continuum model for the Inter-Meander Magnetometer.

The result is a complete set of admittances 132 ($Y_{11}$, $Y_{12}$, $Y_{21}$, $Y_{22}$), as shown in FIG. 22. These admittances are functions of the magnetometer geometry 126, the neighboring media properties 128, the primary excitation, and the secondary load. Predictions of the magnetometer responses are then obtained directly from the admittances using the standard two-port transfer relations 132.

Surface Inductance Density

The media above and below the windings are described by surface inductance densities, $L_n$, defined as the Fourier amplitudes of the normal flux density responses to single Fourier amplitudes of magnetic potential in the planes just above (a) and below (b) the windings. The materials above and below the windings will in general support current densities, so the magnetic potential, $\psi_n$ cannot be used to represent the magnetic field intensity in the bulk of these regions. In the following, the magnetic field is assumed to be independent of z and is represented by the z component of the vector potential.

$$\vec{A} = A_z(x, y)\vec{i}_z \tag{3}$$

$$\vec{B} = \frac{\partial A_z}{\partial y}\vec{i}_x - \frac{\partial A_z}{\partial x}\vec{i}_y \tag{4}$$

Hence, with the Fourier series written in the form:

$$A_z(x, y) = \text{Re}\sum_{n=-\infty}^{+\infty} \hat{A}_n(x)e^{-jk_ny}e^{j\omega t}; k_n = \frac{2n\pi}{\lambda} \tag{5}$$

the surface inductance densities are given by $$\hat{L}_n^a \equiv \frac{k_n^2 \hat{A}_n^a}{\hat{H}_{yn}^a}; \hat{L}_n^b \equiv -\frac{k_n^2 \hat{A}_n^b}{\hat{H}_{yn}^b} \tag{6}$$

The first objective is to predict the response of any particular circuit connected to the secondary to any excitation on the primary for various neighboring media. This requires a detailed description of the windings that can be used with subroutines describing any particular linear neighboring media.

The neighboring media is accounted for by introducing the concept of a surface inductance density. Derivation of the appropriate surface inductance densities is required for each application considered. A generic representation suitable for many of these applications is developed in this section. This representation is then incorporated as a subroutine in the response prediction and parameter estimation algorithms.

Many applications can be represented using a media with multiple homogeneous layers. The required surface inductance densities can be conveniently obtained using transfer relations (J. R. Melcher, Continuum Electromechanics, Cambridge, Mass., MIT Press (1981)). A medium with P layers (each of uniform conductivity, $\sigma$, and permeability, $\mu$) is represented in FIG. 23

Layer j has the properties $\mu_j$, $\sigma_j$ and the thickness $h_j$. The upper surface of the $j^{th}$ layer is designated by j. The transfer relation representing the solution of Laplace's equation for the magnetic vector potential in region j is given by $$\begin{bmatrix} \hat{A}_n^{(j)'} \\ \hat{A}_n^{(j+1)} \end{bmatrix} = \begin{bmatrix} \hat{a}_{11}^{(j)} & \hat{a}_{12}^{(j)} \\ \hat{a}_{21}^{(j)} & \hat{a}_{22}^{(j)} \end{bmatrix} \begin{bmatrix} \hat{H}_{yn}^{(j)'} \\ \hat{H}_{yn}^{(j+1)} \end{bmatrix} \quad (7)$$

where $$\hat{a}_{22}^{(j)} = -\hat{a}_{11}^{(j)} = \frac{\mu_j}{\gamma_j} \coth\gamma_j h_j \quad (8)$$

$$\hat{a}_{12}^{(j)} = -\hat{a}_{21}^{(j)} = \frac{\mu_j}{\gamma_j} \frac{1}{\sinh\gamma_j h_j}$$

$$\gamma_j = \sqrt{k_n^2 + j\mu\sigma\omega}$$

and $\hat{F}_n^{(j+1)}$ and $\hat{F}_n^{(j)'}$ represent the complex amplitude of the $n^{th}$ Fourier component of a field quantity just above the lower and just below the upper interfaces of the $j^{th}$ layer, respectively.

At the jth surface, the boundary conditions are $$\hat{A}_n^{(j)} = \hat{A}_n^{(j)'}; \hat{H}_{yn}^{(j)} - \hat{H}_{yn}^{(j)'} = 0 \quad (9)$$

Surface current densities could also be considered at the interfaces but are not included in this example.

The surface inductance density above the jth interface is given by $$\hat{L}_n^{a(j)} = \frac{k_n^2 \hat{A}_n^{(j)}}{\hat{H}_{yn}^{(j)}} \quad (10)$$

The surface inductance density at x=0 is given by $$\hat{L}_n^a = \hat{L}_n^{a(P+1)}$$

$L_n^a$ is obtained by progressing from the j=1 surface to the j=P+1 surface using the relation $$\hat{L}_n^{a(j+1)} = k_n^2 \hat{a}_{22}^{(j)} + \frac{\hat{a}_{12}^{(j)} \hat{a}_{21}^{(j)} k_n^4}{\hat{L}_n^{a(j)} + k_n^2 \hat{a}_{22}^{(j)}} \quad (11)$$

The j=1 surface is generally at infinity so that $\hat{L}_n^{a(2)} = k_n^2 \hat{a}_{22}^{(1)}$.

An identical relation is obtained for the surface inductance density below the magnetometer interface, with $\hat{L}_n^b$ defined as in Eq. 6.

Fourier Amplitudes in Terms of Collocation Current Densities or Vector Potentials This and the following four sections present a model that accounts for span-wise diffusion of currents within the conducting windings in the y direction for frequency ranges over which these currents are essentially uniform with respect to the x direction. A constant vector potential model is also possible for higher frequencies. The constant vector potential model is similar to the model presented here except the vector potential, A, is assumed to be constant across the conducting windings.

Lengths associated with the windings have the following relative scales $$\Delta << c \sim d < \lambda \quad (12)$$

At low frequencies, conduction in the windings is quasi-steady and current distributions over the cross-section of the windings are uniform with respect to the x and y directions. As the frequency is raised, the conductors will tend to exclude the normal flux density with a resultant redistribution of current over the widths of the conductors in the y direction. With the thickness, $\Delta$, of the conductors much less than the widths c and d, this redistribution of current will occur well below the frequency giving a skin depth on the order of $\Delta$. Thus, the conductor current density remains uniform in the x direction but nonuniform in the y direction. For frequencies at which the skin depth is larger than $\Delta$, the input-output transfer relations are derived by relating the relevant admittances to the surface current densities and hence the winding geometry, excitation frequency, and the properties of the neighboring media.

The surface current density, $\hat{K}(y)$, is represented as a piece-wise linear function. The $N_p$ "collocation" surface current densities in half of the primary and $N_s$ in one of the secondaries are the current densities, $K_\beta$, at the positions, $y_\beta$, where the linear functions are "pieced together."

$$\hat{K}_z(y) = \frac{[(\hat{k}_\beta - \hat{k}_{\beta-1})y + (\hat{k}_{\beta-1}y_\beta - \hat{k}_\beta y_{\beta-1})]}{y_\beta - y_{\beta-1}} \quad (13)$$

$$y_{\beta-1} < y < y_\beta$$

As will be shown in this section, the collocation surface current densities can be determined directly or through collocation on vector potential. Collocation on vector potential requires an equivalent piece-wise linear distribution for the collocation vector potential $\hat{A}_\beta$.

The span-wise diffusion resulting from the tendency of the conductors to exclude the magnetic field at higher frequencies also results in an increasingly uniform vector potential distribution along the y axis in the conducting intervals. Thus, collocation on vector potential becomes numerically convenient at higher frequencies. Ultimately, in the very high frequency range, the vector potential distribution across the windings can be assumed uniform and collocation on vector potential between the windings is used to obtain the response.

The two approaches, collocation on vector potential and collocation on surface current density provide a check for theory and simulations as well as providing additional physical insight and understanding of the underlying physical behavior. In addition, numerical performance may warrant the use of one approach versus the other at different frequencies.

For either collocation on surface current density or on vector potential, the current density is assumed to be negligible between the windings, in the plane of the sensor. No current density collocation points are required in these intervals for the collocation on surface current density approach. The sketch of these currents in FIG. 24 suggests the symmetry implicit to the following developments. For this analysis, the current distribution is assumed to be even about the origin y=0 (i.e., $K_z(y)=K_z(-y) \rightarrow \hat{K}_n=\hat{K}_{-n}$). Furthermore, the current density in the return conductors is assumed to take on the same distribution and the opposite direction so that the current density $K_z(y)=-K_z(y+\lambda/2)$. It follows that the even Fourier amplitudes are zero ($\hat{K}_n=0$, for n even). These assumptions limit this example to circumstances involving stationary media. The current density is given by $$K_z = (y) = \text{Re} \sum_{n=0}^{\infty} 2\hat{K}_{(2n+1)} \cos k_{(2n+1)} y e^{j\omega t} \tag{14}$$

Similarly, the vector potential can be represented as a piecewise linear function. However, additional collocation points are required between the windings since the vector potential is not zero in these intervals. Accordingly, $N_g$ vector potential collocation points are added in the gap between the primary and secondary windings, and $N_{sp}$ collocation points are added in half of the space between the secondaries. The same assumptions on the distribution of current density apply to the distribution of vector potential (e.g., $A_z(y)=A_z(-y) \rightarrow \hat{A}_n=\hat{A}_{-n}$ and $A_z(y)=-A_z(y+\lambda/2) \rightarrow \hat{K}_n=0$, for n even). Also, $A_z(\lambda/4)=0$ for the assumed distribution. The vector potential is given by $$A_Z(y) = \text{Re} \sum_{n=0}^{\infty} 2\hat{A}_{(2n+1)} \cos k_{(2n+1)} y e^{j\omega t} \tag{15}$$

In the following development, the collocation point locations can be given any distribution, as long as the distribution of collocation points on the conductors is symmetric about the center line of each conductor—this restriction is the result of simplifying assumptions necessary for the application of Faraday's law. It is convenient to use a cosinusoidal distribution which provides an increasing density of collocation points near the conductor edges along the y axis.

COLLOCATION ON K $$y_j = \begin{cases} \frac{c}{2} \cos \frac{\pi(N_p - j)}{2N_p} & 0 \le j \le N_p \\ \frac{c}{2} + g + \frac{d}{2}\left[1 - \cos \frac{\pi(j - N_p)}{N_S - 1}\right] & N_p < j \le N_p + N_S \end{cases} \tag{16}$$

COLLOCATION ON A $$y_j = \begin{cases} \frac{c}{2} \cos \frac{\pi(N_p - j)}{2N_p} & 0 \le j \le N_p \\ \frac{c}{2} + \frac{g}{2}\left[1 - \cos \frac{\pi(j - N_p)}{N_g - 1}\right] & N_p < j < N_p + N_g \\ \frac{c}{2} + g + \frac{d}{2}\left[1 - \cos \frac{\pi(j - N_p - N_g)}{N_s}\right] & N_p + N_g \le j < N_p + N_g + N_s \\ \frac{c}{2} + g + d + \frac{sp}{2}\left[1 - \cos \frac{\pi(j - N_p - N_g - N_s)}{N_{sp} + 1}\right] & N_p + N_g + N_s \le j \le N_t \end{cases} \tag{17}$$

Using the orthogonality of the modes, the Fourier amplitudes are written in terms of the collocation surface current densities, $K_\beta$, and the collocation vector potential, $\hat{A}_\beta$.

$$\hat{K}_n = \sum_{\beta=0}^{N_p+N_s} D_{n\beta} \hat{k}_\beta; \quad \hat{A}_n = \sum_{\beta=0}^{N_t-1} F_{n\beta} \hat{A}_\beta \tag{18}$$

where $$\begin{vmatrix} D_{n0} = \Theta_1(n,0) \\ D_{n\beta} = \Theta_1(n,\beta) - \Theta_1(n,\beta-1) \\ \text{for } \beta = 1, \ldots, (N_p - 1) \\ \text{or } (N_p + 2), \ldots, (N_p + N_s - 1) \\ D_{n\beta} = \Theta_3(n,\beta) - \Theta_1(n,\beta-1) \\ \text{for } \beta = N_p \text{ or } (N_p + N_s) \\ D_{n,N_{p+1}} = \Theta_1(n,\beta) - \Theta_3(n,\beta) \end{vmatrix} \begin{vmatrix} F_{n0} = \Theta_1(n,0) \\ F_{n\beta} = \Theta_1(n,\beta) - \Theta_1(n,\beta-1) \\ \text{for } \beta = 1, \ldots, (N_t - 1) \\ \text{where } N_t = N_p + N_g + N_s + N_{sp} \end{vmatrix} \quad (19)$$

with $$\Theta_1(n,\beta) = \frac{\lambda}{(n\pi)^2} \frac{(\cos k_n y_\beta - \cos k_n y_{\beta+1})}{y_{\beta+1} - y_\beta} \quad (20)$$

$$\Theta_3(n,\beta) = \frac{2}{n\pi} \sin k_n y_\beta$$

Flux Continuity and Ampere's Continuity Condition

In this and the following sections, a methodology is presented for solution of the continuum equations resulting from a self-consistent application of flux continuity, Ampere's continuity condition and Faraday's law.

With the vector potential represented in the standard form, Eq. 5, flux continuity across the winding surface (x=0) requires that $$\vec{n} \cdot ||\vec{B}|| = 0 \rightarrow \hat{A}_n^a = \hat{A}_n^b \quad (21)$$

Ampere's law requires that the jump in tangential magnetic field intensity be equal to the surface current density.

$$\vec{n} \times ||\vec{H}|| = \vec{K} \rightarrow \hat{H}_{yn}^a - \hat{H}_{yn}^b = \hat{K}_n \quad (22)$$

It follows from these expressions and the specific surface inductance densities defined by Eq. 6 that $$\hat{A}_n = \frac{\hat{K}_n}{k_n^2} \frac{1}{\left[\frac{1}{\hat{L}_n^a} + \frac{1}{\hat{L}_n^b}\right]} = \frac{\hat{K}_n}{k_n^2} \hat{L}_n^{eq} \quad (23)$$

where $\hat{L}_n^{eq}$ represents the parallel combination of the inductances above and below the windings.

Faraday's Law and the Collocation Conditions

For any contour, Faraday's integral law requires that $$\oint_c \vec{E} \cdot \vec{dl} = -\frac{d}{dt} \int_s \vec{B} \cdot \vec{n} da = -\frac{d}{dt} \oint_c \vec{A} \cdot \vec{dl} \quad (24)$$

Specifically, for a contour passing through a point, y, in the primary or the secondary and continuing along the winding through its m meanders $$\frac{1}{\Delta\sigma} \int \frac{\vec{K} \cdot \vec{dl}}{K} + j\omega lm[\hat{A}(y_\alpha^*) - \hat{A}(y_\alpha^* + \lambda/2)] = \begin{cases} \hat{v}_1 & \text{primary} \\ \hat{v}_2 & \text{secondary} \end{cases} \quad (25)$$

Exploitation of the half-wave symmetry makes it possible to take the contributions from the return legs of the line integrals as being equal to those from the integration through the segment in the first quarter wavelength (i.e., the currents in these "return legs" is -z directed for $i_1 > 0$).

Thus, Eq. 25 reduces to $$\frac{2lm}{\Delta\sigma} \hat{K}(y_\alpha^*) + j\omega lm 2\hat{A}(y_\alpha^*) = \begin{cases} \hat{v}_1 & \text{primary} \\ \hat{v}_2 & \text{secondary} \end{cases} \quad (26)$$

A solution approach similar to the "subdomain method" of weighted residuals is used at this point to obtain the response (B. A. Finlayson, "The Method of Weighted Residuals and Variational Principles," Academic Press, N.Y. (1972)). This method involves the integral of the residual over a finite number of intervals, as opposed to the collocation method which involves evaluation of residuals at a finite number of collocation points. The resulting algorithms are numerically robust and provide a consistent representation of the crowding-out of currents at the edges of the primary and secondary conductors.

Accordingly, Eq. 26 is averaged over $N_p$ and $N_s$ intervals on the primary and secondary conductors, respectively.

$$\frac{1}{y_{\alpha+1}^* - y_\alpha^*} \int_{y_\alpha^*}^{y_{\alpha+1}^*} \left[\frac{2lm}{\Delta\sigma} \hat{K}(y_\alpha^*) + j\omega lm 2\hat{A}(y_\alpha^*)\right] dy = \begin{cases} \hat{v}_1 & \text{primary} \\ \hat{v}_2 & \text{secondary} \end{cases} \quad (27)$$

In the collocation on A approach, additional collocation points are required between the conductors. An additional $N_g$ and $N_{sp}$ intervals are introduced in the gap between conductors and the space between the secondary and the quarter wavelength collocation point along the y axis. The integral of the surface current density over each of these intervals is required to be zero.

$$\int_{y_\alpha^*}^{y_{\alpha+1}^*} \hat{K}(y) dy = \sum_{n=1}^{\infty} 2\hat{A}_n \frac{k_n}{\hat{L}_n^{eq}} (\sin k_n y_{\alpha+1}^* - \sin k_n y_\alpha^*) = 0 \quad (28)$$

Determination of the relevant admittances requires relationships between $(i_1, v_1)$ and $(i_2, v_2)$ which can be found directly by elimination of $A(y_\alpha^*)$ from Eq. 27 using Eq. 13, Eq. 15, Eq. 18, and Eq. 23. This results in the direct solution for the collocation current densities needed to compute the relevant admittances. Alternatively, for collocation on A, $\hat{K}(y_\alpha^*)$ is eliminated from Eq. 27 using the vector potential equivalent of Eq. 13 and Eq. 14, Eq. 18, and Eq. 23. The collocation vector potentials, $\hat{A}_\alpha$, can then be determined and used to find the required collocation current densities, $\hat{\kappa}_\alpha$. A summary of the required steps for each of these approaches is provided below.

COLLOCATION ON K            COLLOCATION ON A         (29)

$$\hat{A}_\alpha = \sum_{n=0}^{\infty} 2\frac{\hat{L}^{eq}_{(2n+1)}}{k^2_{(2n+1)}}\hat{K}_{(2n+1)}\cos k_{(2n+1)}y_\alpha \bigg| \hat{\kappa}_\alpha = \sum_{n=0}^{\infty} 2\frac{k^2_{(2n+1)}}{\hat{L}^{eq}_{(2n+1)}}\hat{A}_{(2n+1)}\cos k_{(2n+1)}y_\alpha$$

Substitution of these expressions into Eq. 27 results in equations that are linear in the collocation surface current densities or vector potentials, respectively. Note that this evaluation depends on the symmetry of the surface current density and vector potential assumed at the outset. Eq. 27 now takes the form $$B\hat{K}=\hat{V} | G\hat{A}=\hat{V} \quad (30)$$

where B is $(N_p+N_s)\times(N_p+N_s)$, G is $(N_t-1)\times(N_t-1)$ and $$\hat{K} = \begin{bmatrix} \hat{\kappa}_1 \\ \vdots \\ \hat{\kappa}_{N_p} \\ \hat{\kappa}_{N_p+1} \\ \vdots \\ \hat{\kappa}_{N_p+N_3} \end{bmatrix}; \hat{V} = \begin{bmatrix} \hat{v}_1 \\ \vdots \\ \hat{v}_1 \\ \hat{v}_2 \\ \vdots \\ \hat{v}_2 \end{bmatrix} \hat{A} = \begin{bmatrix} \hat{A}_1 \\ \vdots \\ \hat{A}_{N_p} \\ \hat{A}_{N_p+1} \\ \vdots \\ \hat{A}_{N_p+N_g-1} \\ \hat{A}_{N_p+N_g} \\ \vdots \\ \hat{A}_{N_p+N_g+N_s} \\ \hat{A}_{N_p+N_g+N_s+1} \\ \vdots \\ \hat{A}_{N_t-1} \end{bmatrix}; \quad (31)$$

$$\hat{V} = \begin{bmatrix} \hat{v}_1 \\ \vdots \\ \hat{v}_1 \\ 0 \\ \vdots \\ 0 \\ \hat{v}_2 \\ \vdots \\ \hat{v}_2 \\ 0 \\ \vdots \\ 0 \end{bmatrix};$$

The rows of B and G correspond to equations for specific intervals designated by $\alpha$. The columns of B and G correspond to the collocation currents and vector potentials designated by $\beta$. Intervals within the conductors along the y axis include all collocation points in the collocation on K approach; however, for collocation on A, the additional intervals between conductors must be included. The elements of B corresponding to intervals within the conductors are given by For $\alpha \neq 0, N_p, N_{p+1}$ or $N_p + N_3$      (32)

$$B_{\alpha,\alpha-1} = \frac{1}{y^*_{\alpha+1} - y^*_\alpha}\left[\frac{2lm}{\Delta\sigma} S_K(\alpha, \alpha-1) - j\omega lm2\Theta_4(\alpha, \alpha)\right]$$

$$B_{\alpha,\alpha} = \frac{1}{y^*_{\alpha+1} - y^*_\alpha}\left\{\frac{2lm}{\Delta\sigma} S_K(\alpha, \alpha) + j\omega lm2[\Theta_5(\alpha, \alpha+1) - \Theta_4(\alpha, \alpha-1)]\right\}$$

$$B_{\alpha,\alpha+1} = \frac{1}{y^*_{\alpha+1} - y^*_\alpha}\left[\frac{2lm}{\Delta\sigma} S_K(\alpha, \alpha+1) - j\omega lm2\Theta_5(\alpha, \alpha)\right]$$

for $\beta \neq \alpha - 1, \alpha$ or $\alpha + 1$ $$B_{\alpha\beta} = \frac{1}{y^*_{\alpha+1} - y^*_\alpha}\left[\frac{2lm}{\Delta\sigma} S_K(\alpha, \beta)\right]$$

For $\alpha = 0$ or $N_p + 1$ (33)

$$B_{\alpha,\alpha} = \frac{1}{y^*_{\alpha+1} - y^*_\alpha}\left[\frac{2lm}{\Delta\sigma}S_K(\alpha,\alpha) + j\omega lm 2\Theta_5(\alpha,\alpha+1)\right]$$

$$B_{\alpha,\alpha+1} = \frac{1}{y^*_{\alpha+1} - y^*_\alpha}\left[\frac{2lm}{\Delta\sigma}S_K(\alpha,\alpha+1) - j\omega lm 2\Theta_5(\alpha,\alpha)\right]$$

for $\beta \neq \alpha$ or $\alpha + 1$ $$B_{\alpha\beta} = \frac{1}{y^*_{\alpha+1} - y^*_\alpha}\left[\frac{2lm}{\Delta\sigma}S_K(\alpha,\beta)\right]$$

For $\alpha = N_p$ or $N_p + N_3$ (34)

$$B_{\alpha,\alpha-1} = \frac{1}{y^*_{\alpha+1} - y^*_\alpha}\left[\frac{2lm}{\Delta\sigma}S_K(\alpha,\alpha-1) + j\omega lm 2\Theta_4(\alpha,\alpha)\right]$$

$$B_{\alpha,\alpha} = \frac{1}{y^*_{\alpha+1} - y^*_\alpha}\left[\frac{2lm}{\Delta\sigma}S_K(\alpha,\alpha) - j\omega lm 2\Theta_4(\alpha,\alpha-1)\right]$$

for $\beta \neq \alpha - 1$ or $\alpha$ $$B_{\alpha\beta} = \frac{1}{y^*_{\alpha+1} - y^*_\alpha}\left[\frac{2lm}{\Delta\sigma}S_K(\alpha,\beta)\right]$$

where $$S_K(\alpha,\beta) = 2\sum_{\substack{n=1 \\ odd}}^{\infty} D_{n\beta}\frac{\hat{L}_n^{eq}}{k_n^3}(\sin k_n y^*_{\alpha+1} - \sin k_n y^*_\alpha)$$

and $$\Theta_4(j,k) = \frac{-(y_j^2 - y_j^{*2})/2 + y_k(y_j - y_j^*)}{y_j - y_{j-1}} \quad (35)$$

$$\Theta_5(j,k) = \frac{-(y_{j+1}^{*2} - y_j^2)/2 + y_k(y^*_{j+1} - y_j)}{y_{j+1} - y_j} \quad (36)$$

The elements of G are given by Eq.s 30–32 with $S_k$ replaced by $S_A$, $N_p+1$ replaced by $N_p+N_g$ and $N_p+N_s$ replaced by $N_p+N_g+N_s$. $S_A$ is given by $$S_A(\alpha,\beta) = 2\sum_{\substack{n=1 \\ odd}}^{\infty} F_{n\beta}\frac{k_n}{\hat{L}_n^{eq}}(\sin k_n y^*_{\alpha+1} - \sin k_n y^*_\alpha) \quad (37)$$

The additional elements of G are derived from Eq. 28 and are given by $$G_{\alpha\beta} = \frac{1}{y^*_{\alpha+1} - y^*_\alpha}S_A(\alpha,\beta) \quad (38)$$

for $\alpha \leq N_p$ or $N_p + N_g \leq \alpha \leq N_p + N_g + N_s$

Inversion of these expressions gives the desired distribution of collocation surface current densities and vector potentials.

$$\hat{K} = C\hat{V};\ C = B^{-1}|\hat{A} = M\hat{V};\ M = G^{-1} \quad (39)$$

The total currents on the primary and secondary are given by $$\hat{i}_1 = \sum_{\beta=0}^{N_p-1}(\hat{k}_\beta + \hat{k}_{\beta+1})(y_{\beta+1} - y_\beta) \quad \bigg| \quad \hat{i}_1 = \sum_{\beta=0}^{N_p-1}(\hat{k}_\beta + \hat{k}_{\beta+1})(y_{\beta+1} - y_\beta) \quad (40)$$

$$\hat{i}_2 = \sum_{\beta=N_p+1}^{N_p+N_s-1}(\hat{k}_\beta + \hat{k}_{\beta+1})(y_{\beta+1} - y_\beta) \quad \bigg| \quad \hat{i}_2 = \sum_{\beta=N_p+N_g}^{N_p+N_g+N_s-1}(\hat{k}_\beta + \hat{k}_{\beta+1})(y_{\beta+1} - y_\beta)$$

The collocation surface current densities have not yet been determined in the collocation on A approach. However, these current densities can be determined easily from Eq. 26 (evaluated at $y_\alpha$ instead of $y^*_\alpha$) using the following expression for $\hat{A}_\alpha$.

$$\hat{A}_\beta = \sum_{\alpha=0}^{N_p} M_{\beta\alpha}\hat{v}_1 + \sum_{\alpha=N_p+N_g}^{N_p+N_g+N_s} M_{\beta\alpha}\hat{v}_2 \quad (41)$$

Equivalent Circuit Admittances

In accordance with the relations for a general two port, the relevant admittances are defined by $$\hat{i}_1 = Y_{11}\hat{v}_1 + Y_{12}\hat{v}_2,\ \hat{i}_2 = Y_{21}\hat{v}_1 + Y_{22}\hat{v}_2 \quad (42)$$

The relevant system transfer functions, with an infinite load impedance on the secondary are given by $$\frac{\hat{v}_2}{j\omega \hat{i}_1} = \frac{-jY_{21}/\omega}{Y_{12}Y_{21} - Y_{11}Y_{22}} \quad (43)$$

$$\frac{\hat{v}_2}{\hat{v}_1} = -\frac{Y_{21}}{Y_{22}}$$

$$\frac{\hat{v}_1}{\hat{i}_1} = \frac{jY_{22}}{Y_{12}Y_{21} - Y_{11}Y_{22}}$$

In the first transfer function, the transimpedance, $v_2/i_1$, is divided by $j\omega$ to obtain the transinductance, $v_2/j\omega i_1$. The transinductance provides a useful representation of the effects of neighboring material properties on the magnetometer response, and has several advantages over alternative functions.

It follows from Equations 40 and 42, with $v_2=0$, that $$Y_{11} = \sum_{\beta=0}^{N_p-1} \sum_{\alpha=0}^{N_p} (C_{\beta\alpha} + C_{\beta+1,\alpha}) \cdot (y_{\beta+1} - y_\beta) \quad (44)$$

$$\left| = \sum_{\beta=0}^{N_p-1} \left\{ -j\omega\Delta\sigma \left[ \sum_{\alpha=1}^{N_p} (M_{\beta\alpha} + M_{\beta+1,\alpha}) \right] \cdot (y_{\beta+1} - y_\beta) \right\} + G_p \right.$$

$$Y_{21} = \sum_{\beta=N_p+1}^{N_p+N_s-1} \sum_{\alpha=0}^{N_p} (C_{\beta\alpha} + C_{\beta+1,\alpha}) \cdot (y_{\beta+1} - y_\beta)$$

$$\left| = \sum_{\beta=N_p+N_g}^{N_p+N_g+N_s+1} \left\{ -j\omega\Delta\sigma \left[ \sum_{\alpha=1}^{N_p} (M_{\beta\alpha} + M_{\beta+1,\alpha}) \right] (y_{\beta+1} - y_\beta) \right\} \right.$$

and with $v_1=0$, $$Y_{12} = \sum_{\beta=0}^{N_p-1} \sum_{\alpha=N_p+1}^{N_p+N_s} (C_{\beta\alpha} + C_{\beta+1,\alpha}) \cdot (y_{\beta+1} - y_\beta) \quad (45)$$

$$\left| = \sum_{\beta=0}^{N_p-1} \left\{ -j\omega\Delta\sigma \left[ \sum_{\alpha=N_p+N_g}^{N_p+N_g+N_s} (M_{\beta\alpha} + M_{\beta+1,\alpha}) \right] (y_{\beta+1} - y_\beta) \right\} \right.$$

$$Y_{22} = \sum_{\beta=N_p+1}^{N_p+N_s-1} \sum_{\alpha=N_p+1}^{N_p+N_s} (C_{\beta\alpha} + C_{\beta+1,\alpha})(y_{\beta+1} - y_\beta)$$

$$\left| = \sum_{\beta=N_p+N_g}^{N_p+N_g+N_s-1} \left\{ -j\omega\Delta\sigma \left[ \sum_{\alpha=N_p+N_g}^{N_p+N_g+N_s} (M_{\beta\alpha} + M_{\beta+1,\alpha}) \right] (y_{\beta+1} - y_\beta) \right\} + G_s \right.$$

where $G_p$ and $G_s$ represent the DC conductance of the primary and secondary, respectively, and are given by $$G_p = \frac{c\Delta\sigma}{2lm} \Big| G_s = \frac{d\Delta\sigma}{lm} \quad (46)$$

Current and Vector Potential Distributions

Conduction in the windings at low frequencies is quasi-steady and the distribution of surface current density is uniform in both the x and y directions. The vector potential at low frequencies should exhibit a relatively smooth distribution since the presence of the conducting windings will not deflect the lines of magnetic flux at low frequencies. The symmetry of the Inter-Meander Magnetometer construct permits a qualitative prediction of the vector potential distribution. A sample distribution is shown in FIGS. 25(a–f), where the surface current density and vector potential at a particular collocation point are designated by a circle or triangle, respectively. At the quarter wavelength point, the vector potential is zero due to symmetry assumptions. Consider the flux linked through a surface bounded by a line in the z direction at position y', between y=0 and y=$\lambda$/4, and a line at y=$\lambda$/4. Assuming the current in the primary is in the +z direction, as y' moves away from $\lambda$/4 toward the primary in the −y direction, more and more flux is linked until a maximum vector potential is reached at the center of the primary. This is consistent with the symmetry assumed in the continuum model and is represented mathematically by Eq. 25.

As the frequency is raised, the conductors tend to exclude the normal flux density, and the current redistributes over the widths of the conducting windings in the x and y directions. However, with the thickness of the conductors in the x direction, D, much less than the widths c and d of the primary and secondary in the y direction, there will be a range of frequencies over which the current distribution remains essentially uniform in the x direction, but not in the y direction. The current begins to crowd out until it reaches a distribution with a 1/SQRT(r) dependence. The current density at the edge of the conducting windings goes to infinity and the vector potential distribution becomes uniform across the conducting intervals.

The simulated responses of the collocation on A and collocation on K approaches are shown side by side in FIGS. 25(a–f) for the parameters in the original construct of FIG. 21. The (a) construct in FIG. 21 provides increased TDES for some specific applications. The collocation on A responses are for simulations using 20 collocation points within each of the following: primary, secondary, gap between primary and secondary, and the space between the secondary and the quarter wavelength point. This will be denoted by (20p, 20g, 20s, 20sp). In the collocation on K responses, 20 collocation points are used in the primary and secondary, no collocation points are required in the nonconducting intervals, this will be denoted by (20p, 20s). The current and vector potential in the nonconducting regions are designated by smooth curves in the collocation on K approach, since no collocation points are required in these regions.

These distributions are normalized in accordance with the following normalized version of Eq. 26.

$$\hat{K}(y_\alpha^*) + j\hat{A}(y_\alpha^*) = \begin{cases} \hat{v}_1 & \text{primary} \\ \hat{v}_2 & \text{secondary} \end{cases} \quad (47)$$

$$\hat{K} = \frac{\hat{l}_i}{c}\hat{K}$$

$$\hat{A} = \frac{\hat{l}_i}{\omega\sigma\Delta c}\hat{A} \quad (48)$$

$$\hat{v}_i = \frac{2lm\hat{l}_1}{\Delta\sigma c}\hat{v}_i$$

Eq. 47 is combined with Eq. 39 and the transfer relations in Eq. 43 to obtain the following normalized equations for the current and vector potential.

For collocation $$\hat{K}_\beta = \frac{cY_{21}}{Y_{12}Y_{21} - Y_{11}Y_{22}}\left\{-\frac{Y_{22}}{Y_{21}}\sum_{\alpha=1}^{N_p} C_{\beta\alpha} + \sum_{\alpha=N_p}^{N_p+N_s} C_{\beta\alpha}\right\} \text{ on } K \quad (49)$$

and the vector potential distribution can be obtained from Eq. 29. For collocation on A, $$\hat{A}_\beta = \frac{\omega\sigma\Delta cY_{21}}{Y_{12}Y_{21} - Y_{11}Y_{22}}\left\{-\frac{Y_{22}}{Y_{21}}\sum_{\alpha=1}^{N_p} M_{\beta\alpha} + \sum_{\alpha=N_p+N_g}^{N_p+N_g+N_s} M_{\beta\alpha}\right\} \quad (50)$$

and the current distribution can be obtained from Eq. 29 or Eq. 47.

The collocation on A approach remains numerically well behaved until about 100 MHz for the original geometry in FIG. 21. The collocation on K approach runs into numerical trouble at about 1 MHz, even with large numbers of collocation points. This is a result of the crowding-out of the current toward the edges of the primary and secondary conductors. As a result, it is convenient to use collocation on K in the low frequency range (<0.1 MHz) and collocation on A beyond this frequency. Collocation on K runs faster with the same density of collocation points, since no collocation points are required by this approach in the nonconducting intervals.

The resulting distributions in FIGS. 25(a–f) demonstrate that the two approaches agree well at frequencies below 0.5 MHz. The magnitude of the vector potential increases proportionally with the drive frequency; this is consistent with physical intuition derived from Faraday's law. This provides another check for the simulation algorithms and related theory.

Figure 26:
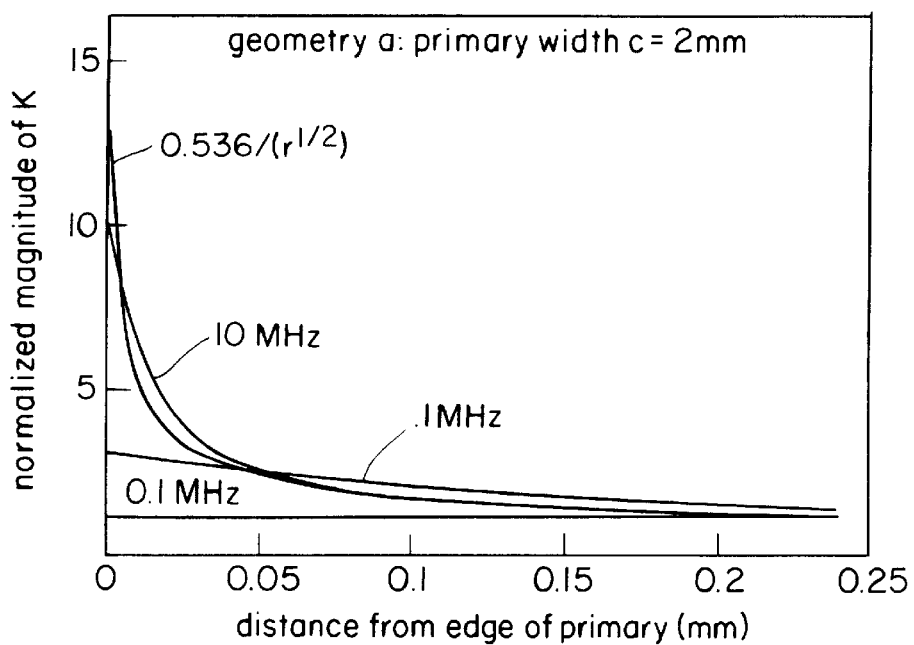
FIG. 26 is a plot of the current distribution in the primary winding for an Inter-Meander Magnetometer with the (a) construct as predicted by the continuum model, compared with the $1/(r^{1/2})$ distribution predicted with an analytical model for a perfectly conducting fin.

The current distribution in the primary for the (a) construct of FIG. 21 at 10 MHz using collocation on A is compared with the predicted 1/SQRT(r) distribution in FIG. 26. As the frequency is raised from 0.1 MHz to 10 MHz, the current distribution approaches the predicted 1/SQRT(r) distribution. The proportionality constant for the predicted distribution has been selected for visual convenience, by setting the 0.2 mm value for the 1/SQRT(r) distribution equal to that of the 10 MHz current distribution. At 10 MHz with the conductivity of $5.8 \times 10^7$ mhos/m, the distribution is close enough to that of a perfect conductor to warrant the use of a constant vector potential model.

At about 10 MHz, the magnetic skin depth is on the order of $\Delta$ for construct (a). Thus, beyond this frequency, the assumptions of the span-wise diffusion model are not met.

Measurement Optimization, Using Singular Value Decomposition (SVD)

The wide range of applications and the complex nonlinear parameter space common in nondestructive electromagnetic measurement applications necessitates the introduction of a generic tool for evaluating measurement performance. Properties such as sensitivity, selectivity, robustness, dynamic range and bandwidth must be quantified in order to provide a useful tool for optimization and comparison of sensor design and measurement performance.

First, a general method for measurement performance quantification is developed using SVD on the Jacobian, which relates differential variations in measured properties to differential changes in the transinductance magnitude and phase. Several applications of SVD optimization are discussed in detail including: (1) the measurement of the thickness and conductivity for thin metal foils and films, (2) the measurement of conductivity-thickness product and air-gap height for thin foils, (3) the measurement of air-gap height and conductivity for thick metal plates, and (4) the measurement of proximity relative to a highly permeable media. Application of the developed methods is also appropriate for more advanced applications such as case depth measurement in heat treated metals, coating thickness measurements for metal on metal, complex permeability and conductivity measurement for ferrous alloys, and many other applications requiring one or more MUT property estimates on multilayered media.

SVD provides the means to both quantify and visualize the relationship between variations in the physical and geometric unknown properties and measured quantities such as the transinductance.

First, the formulation of the Jacobian relating the unknown properties to the measured quantities is required. Care must be taken in this formulation to facilitate the appropriate weighting of compared quantities. The measurement of conductivity, $\sigma$, and thickness, $\Delta$, for a metal foil at a known height above the Inter-Meander Magnetometer is used to demonstrate the formulation. The measurement vector might be composed of the transinductance, $v_2/j\omega i_1$, magnitude and phase. Scaling in accordance with the logarithm of the complex transinductance provides the required consistency.

$$\hat{\Gamma} = \log\left(\frac{v_2}{j\omega i_1}\right) = \log\left|\frac{v_2}{j\omega i_1}\right| + j(\log e)\angle\left(\frac{v_2}{j\omega i_1}\right) \quad (51)$$
$$= \hat{\Gamma}_r + j\hat{\Gamma}_i$$

The unknowns in the example are the conductivity, $\sigma$, and the thickness, $\Delta$, of the metal foil. A differential change in the transinductance magnitude and phase is related to variations in the unknown properties by $$\hat{\Gamma} = \log\left(\frac{v_2}{j\omega i_1}\right) = \log\left|\frac{v_2}{j\omega i_1}\right| + j(\log e)\angle\left(\frac{v_2}{j\omega i_1}\right) \quad (51)$$
$$= \hat{\Gamma}_r + j\hat{\Gamma}_i$$

Thus, the relevant Jacobian is defined by the relation $$d\hat{\Gamma} = J d\underline{\theta} \quad (53)$$

$$d\hat{\Gamma} = \begin{bmatrix} d\hat{\Gamma}_r \\ d\hat{\Gamma}_i \end{bmatrix}; d\underline{\theta} = \begin{bmatrix} d\sigma \\ d\Delta \end{bmatrix}$$

The elements of the Jacobian are computed numerically at an operating point, $(\sigma_o, \Delta_o)$. These derivatives are carefully scaled by both the unknown property, $\theta_o$, and the operating point measured quantity, $\Gamma^o$ (e.g., transinductance magnitude or phase at the operating point), according to the relation $$\frac{\partial \Gamma}{\partial \theta} \approx \frac{\theta_o}{\Gamma^o} \frac{\delta \Gamma}{\delta \theta} \quad (54)$$

Note that in more complex applications the Jacobian may not be a square matrix. For example, a two-frequency transinductance measurement might be used to measure two physical quantities, resulting in a 4×2 Jacobian. Only the 2×2 case is addressed here in detail.

The m by n matrix J can be factored into (G. Strang, Linear Algebra and Its Applications, Third Edition, Harcourt Brace Jovanovich, Inc., San Diego, Calif. 1988)

$$J = U\Sigma V^T = \text{(orthogonal) (diagonal) (orthogonal)} \quad (55)$$

The columns of U are the left singular vectors of J, the columns of V are the right singular vectors of J and the r singular values on the diagonal of $\Sigma$ are the nonzero eigenvalues of both $JJ^T$ and $J^TJ$, where r is the rank of J.

The singular values and singular vectors can be displayed in a manner that provides visual insight into the underlying phenomenology of a particular two property measurement. As foundation, consider a perturbation of the unknown vector, $d\underline{\theta}$, of unit magnitude in the direction of a right singular vector of J—(let this vector be denoted by $\underline{v}_1$). The resulting variation in the measured quantities, $d\Gamma$, in response to the perturbation in the unknown vector, $\underline{v}_1$, will be $$d\Gamma = \sigma_i \underline{u}_i \quad (56)$$

where $\sigma_i$ and $\underline{u}_1$ are the singular value and left singular vector associated with the right singular vector, $\underline{v}_i$.

Figure 27A:
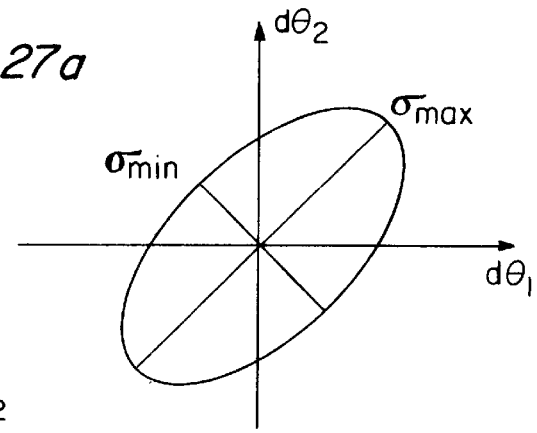
FIGS. 27(a–c) are representations of a "Generalized Sensitivity Ellipse" for a singular value decomposition representation of a 2×2 Jacobian that relates variations in the MUT properties, $\theta_1$ and $\theta_2$ to variations in the measurements, $\Gamma$ at the sensor terminals.
Figure 27B:
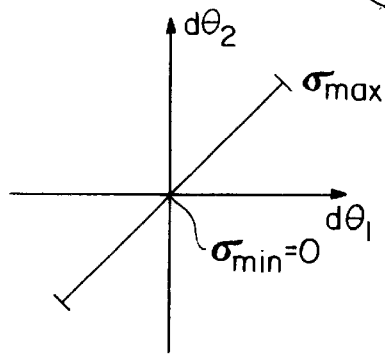
Figure 27C:
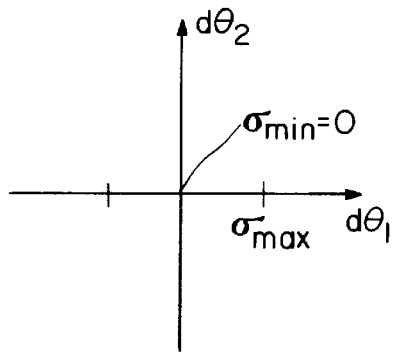

A useful visualization which relates to the sensitivity of the measurement vector to perturbations in the unknown properties is provided by the "Generalized Sensitivity Ellipse" representation in FIGS. 27(a–c). Such ellipsoids have been used to provide visual tools for design of mechanical linkages (H. Asada and K. Youcef-Toumi, Direct Drive Robots: Theory and Practice, MIT Press, 1987). The major axis of the ellipse is assigned the magnitude of the maximum singular value, $\sigma_{max}$, and the direction of its associated right singular vector, as shown. Similarly, the minor axis of the ellipse is assigned the magnitude of the minimum singular value and associated right singular vector. The left singular vectors can also be used to map perturbations of the unknown vector into the measured quantity space.

Common parameter estimation techniques, such as Newton's method, generally use a form of the Jacobian to obtain updates of the estimated parameters. The following sections show that the evaluation of the singular values and singular vectors permits the identification of regions of improved measurement performance in the nonlinear parameter space, for specific applications.

The ability to estimate two properties independently is called the selectivity. In the following sections, it is shown that the condition number, $\sigma_{min}/\sigma_{max}$, provides an excellent measure of selectivity for a two-property measurement application. For this definition of the condition number, a value of 1.0 provides the highest degree of selectivity, while a condition number of 0.0, a singularity point, implies that it is possible to perturb the unknown property vector in a manner that would be unobservable from the measured quantities. Each of these cases is demonstrated for actual measurement applications in the following sections.

Conductivity and Thickness Measurement for Thin Foils

Conventional methods for interpreting eddy current measurements using phaser diagrams often draw on first order approximations or lumped parameter representations. For example, it is common to introduce similarity conditions such as $\sigma f$ (the conductivity-frequency product) or $\sigma\Delta$ (the conductivity-thickness product). For many conventional eddy current sensor measurements, maintaining either of these products constant implies similitude (Nondestructive Testing Handbook, 2d Edition, Vol. 4, Electromagnetic Testing, ASNT, 1986).

A limit frequency, $f_g$, can be defined. Below $f_g$ assumptions such as uniform current in the driven and sensing coils are accurate. It is quite reasonable under this condition to expect a degree of similitude associated with the $\sigma f$ product. This condition is derived from the skin depth or depth of penetration, which is defined by $\delta = \text{SQRT}(2/\omega\mu\sigma)$. Unfortunately, for the applications considered here it is of particular interest to go beyond this limit frequency.

Beyond this limit frequency, a single characteristic conductivity cannot provide a sufficient similarity criterion. In fact, there must be at least two such similarity groups to account for the two different conductivities (e.g., the conductivity of the windings and that of the MUT). It would be impossible to maintain similitude at different frequencies without adjusting both the conductivity of the MUT and the conductivity of the windings themselves. Actually, an exact representation would require an infinite number of such similarity groups. Similitude would only exist if each of these groups is held constant.

One might also be tempted to normalize the frequency axis by the limit frequency. This is commonly called the frequency ratio (Nondestructive Testing Handbook, 2d Edition, Vol. 4, Electromagnetic Testing, ASNT, 1986). This may be a useful scaling but should not generally be used as a similarity criterion. The limitation of such a similitude assumption is apparent from a closer look at the parameter γ in the magnetic diffusion transfer relations presented in the surface inductance density section.

$$\gamma_j = \sqrt{k_n^2 + j\mu\sigma\omega} \; ; k_n = \frac{2\pi n}{\lambda}; \omega = 2\pi f \qquad (57)$$

The excitation of higher order Fourier components (n>1) would effect the relevant magnetic diffusion time, $\tau_m = \mu\sigma l^2$. Of course in a continuum representation there are an infinite number of relevant magnetic diffusion times—one associated with each Fourier component in the infinite series of Eq. 14. The Inter-Meander Magnetometer was originally designed to impose a prescribed magnetic potential at a fixed wavelength. However, the excitation of shorter wavelength Fourier components is increased when span-wise diffusion in the conducting windings is significant, which often occurs when the neighboring material is located a small fraction of the imposed wavelength above the sensor.

Fortunately, this additional complexity provides additional leverage and, consequently, improved selectivity, sensitivity, and dynamic range for many applications. In this section it is used to enable measurement of conductivity and thickness at a single temporal frequency.

In general, eddy current sensors provide only a measure of surface conductivity, $\sigma_s = \sigma\Delta$, when the skin depth $\delta \gg \Delta$. The excitation of a wide range of Fourier components including short wavelengths enables the independent measurement of conductivity and thickness at a single temporal frequency when $\delta \gg \Delta$.

First, a plot of the nonlinear parameter space for a wide range of conductivity and thickness is displayed. This plot is evaluated at an excitation frequency near the TDECF, which is in the range where currents are redistributing themselves in accordance with span-wise diffusion. Second, the frequency responses over a range of foil conductivity and foil thickness are discussed and experimental validation of the span-wise diffusion continuum model is provided. Then SVD is performed to determine the optimal measurement range for two different metal foils. Finally, the actual measurement of conductivity and thickness is demonstrated for the two metal foils.

It is assumed in the remainder of this section that the height of the conducting foil is measurable by some other means as discussed in the next paragraph. It may be possible to measure the conductivity, height and thickness of a conducting layer at a single temporal frequency, but this is not attempted here.

One method for independent measurement of the foil height above the sensor is to use a temporal frequency at which the skin depth is smaller than the thickness of the metal foil but remains larger than the thickness of the conducting windings. The thickness of the conducting windings for the Inter-Meander Magnetometer used in the experiments is 25 μm. At 1.58 MHz the skin depth in copper (σ=5.8E7 mhos/m) is about 50 μm. The foils selected for the two examples must therefore be thicker than about 100 μm to permit independent measurement of the foil height at 1.58 MHz without knowledge of the foil thickness or conductivity. To demonstrate that this measurement can also be performed without knowledge of the foil conductivity, a plot of transinductance magnitude and phase is provided in FIG. 28.

From this figure it is clear that a gross estimate of the foil conductivity provides sufficient knowledge for independent measurement of the foil height. It is also clear that the foil thickness D, has only a small effect on the transinductance magnitude. As a result, the transinductance magnitude at 1.58 MHz will be used to adjust the height in the experimental setup.

Note also that a good measure of the foil conductivity could be obtained from the phase measurement. Thus, the independent measurement of conductivity and height is possible at frequencies meeting the prescribed limitations with regard to skin depth.

Figure 29:
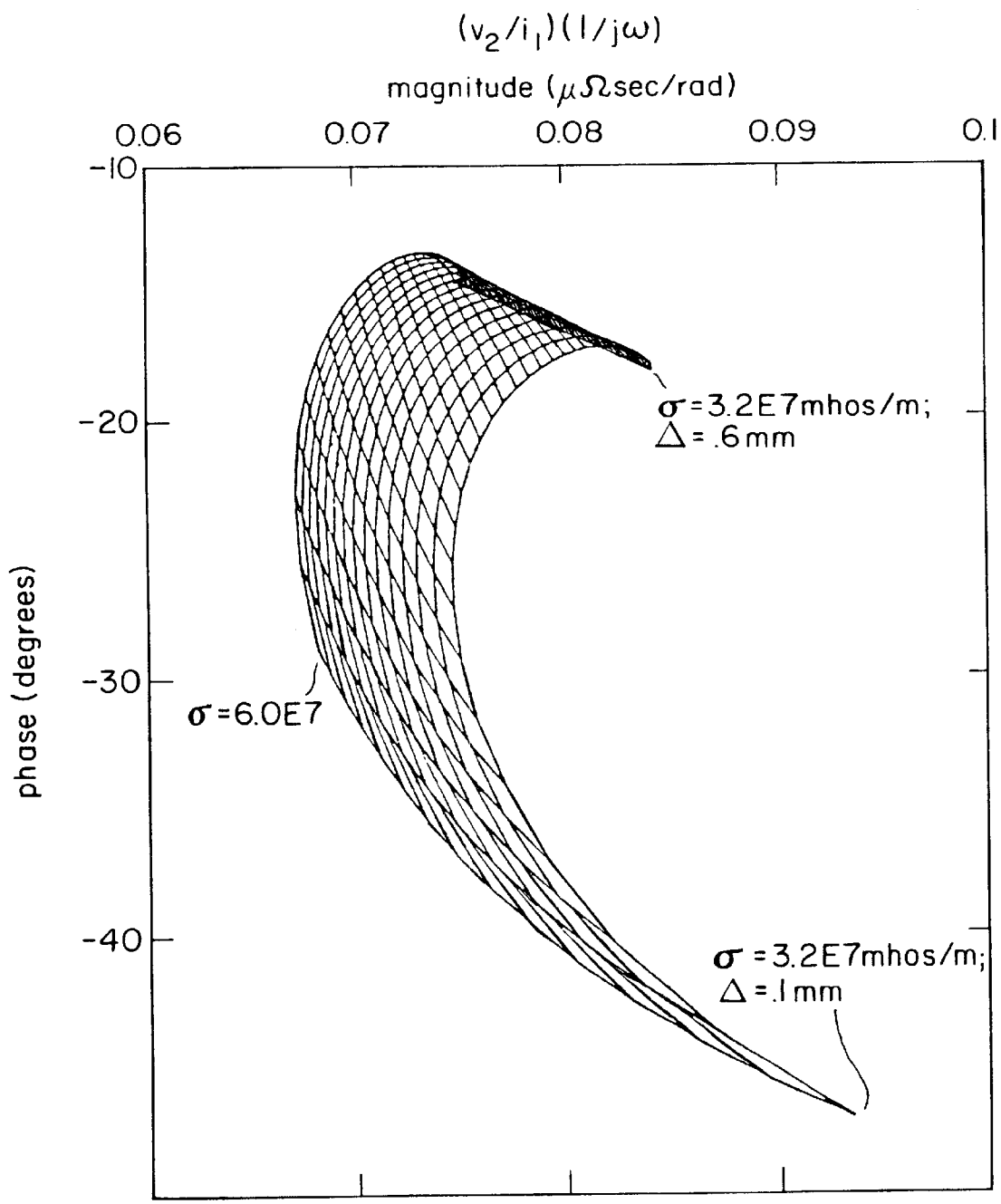
FIG. 29 is a transinductance magnitude versus phase plot with a two-dimensional property estimation grid constructed from lines of constant foil conductivity and lines of constant foil thickness.

The nonlinear parameter space for the transinductance magnitude and phase is plotted in FIG. 29. Lines of constant conductivity are plotted for foil conductivity, σ, ranging from 3.2×10⁷ mhos/m to 6.0×10⁷ mhos/m in increments of 2.0×10⁶ mhos/m. Lines of constant foil thickness are plotted for foil thickness, Δ, ranging from 0.1 mm to 0.6 mm in increments of 0.0125 mm.

Several observations can be made from this plot. First, and most interesting, there is a wide range of thickness and conductivity values for which a small increase in thickness at a constant conductivity actually results in a larger transinductance magnitude. This is counterintuitive and inconsistent with results expected from models that don't account for the effects of span-wise diffusion in the windings.

Figure 30A:
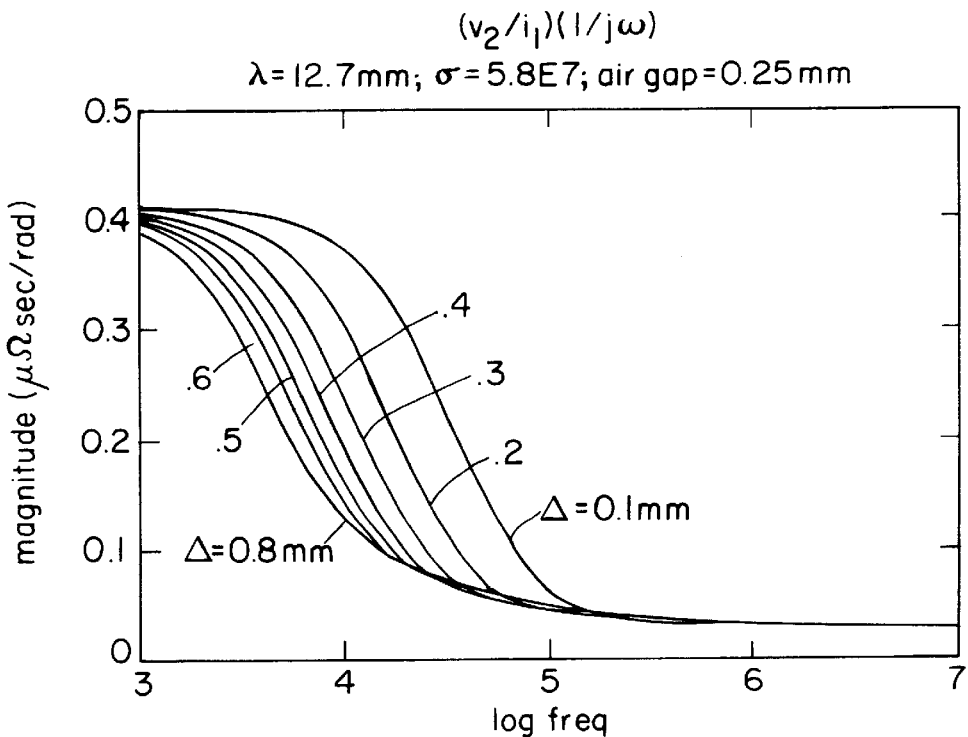
FIGS. 30(a–b) are plots illustrating the effect of foil thickness on the transinductance magnitude and phase.
Figure 30B:
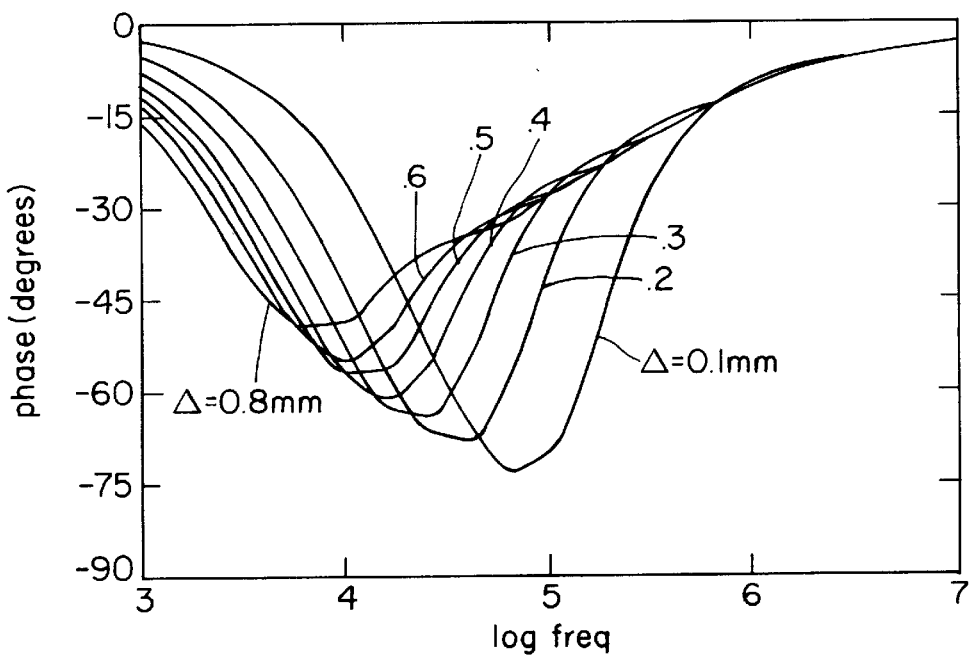

A physical explanation is made apparent by looking at the frequency response variation with thickness at a given conductivity. This is demonstrated in FIGS. 30(a–b). The symmetric phase variation typical of a metal, that exhibits ohmic conduction, is approached in this figure when Δ is smaller than 0.1 mm. For thicker foils, a second transition frequency is apparent. The expected frequency for this transition can be estimated using a characteristic conductivity and characteristic dimensions. The magnetic diffusion time $\tau m \equiv \mu\sigma l_1 l_2$, where $\mu = \mu_o$, σ is a characteristic conductivity derived from both the conductivity of the windings and that of the neighboring media, and $l_1$, $l_2$ are two characteristic lengths, derived from some combination of the width and thickness of the driven winding, the spacing between primary and secondary windings, the imposed wavelength, and any other relevant dimension.

Figure 31A:
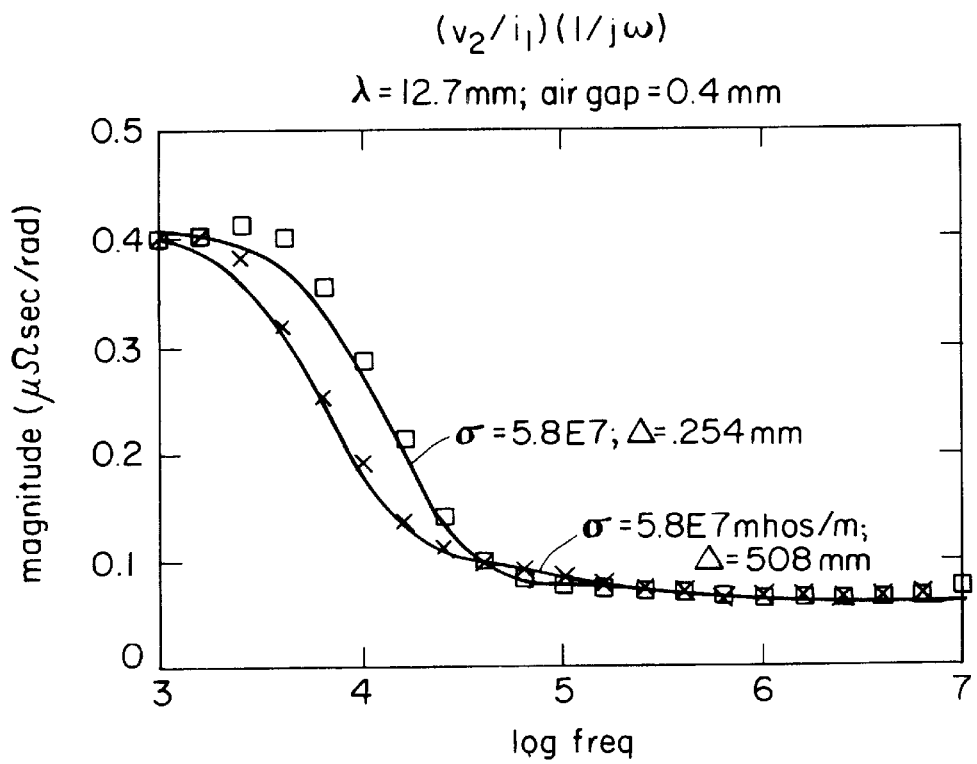
FIGS. 31(a–b) are plots showing experimental data measured with the Inter-Meander Magnetometer prototype sensor for two different foil thicknesses indicated with squares and crosses, and the predicted response simulated with the continuum model indicated with the curved lines.
Figure 31B:
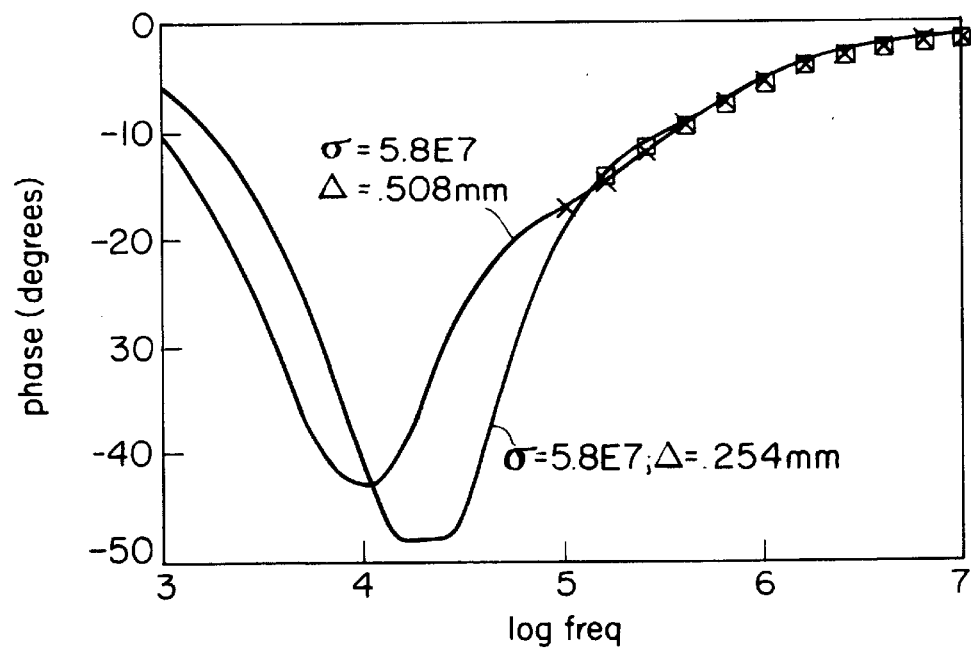
Figure 32A:
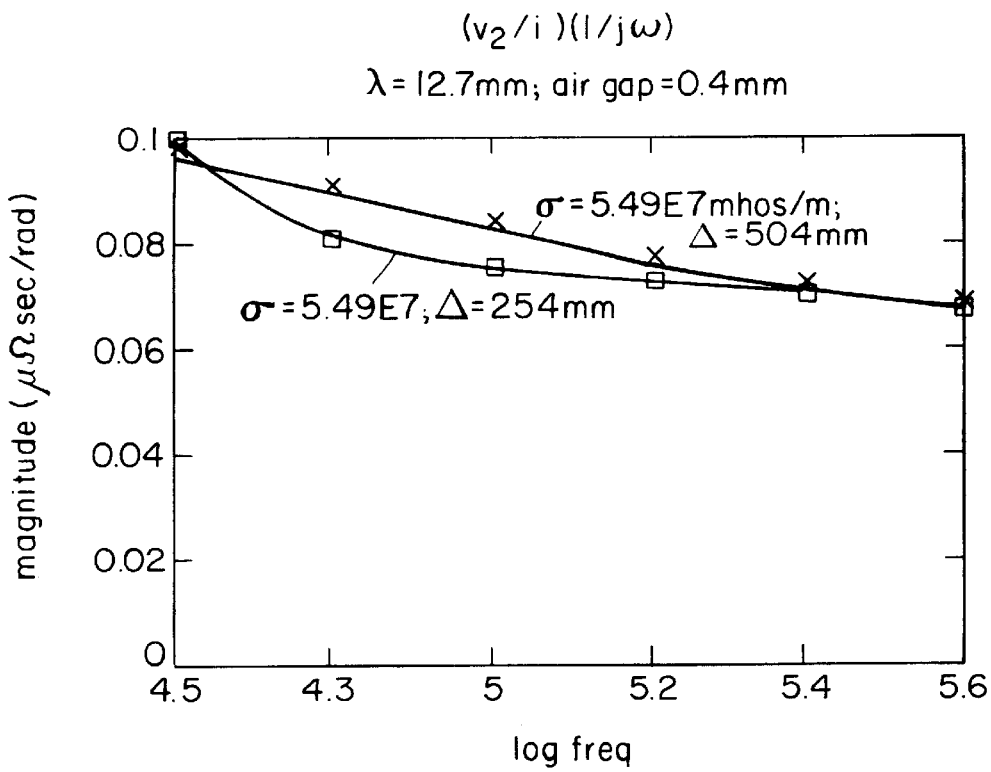
FIGS. 32(a–b) are an expanded views of the region near the TDECF of FIGS. 31(a–b) to demonstrate the behavior produced by the transverse diffusion effect.
Figure 32B:
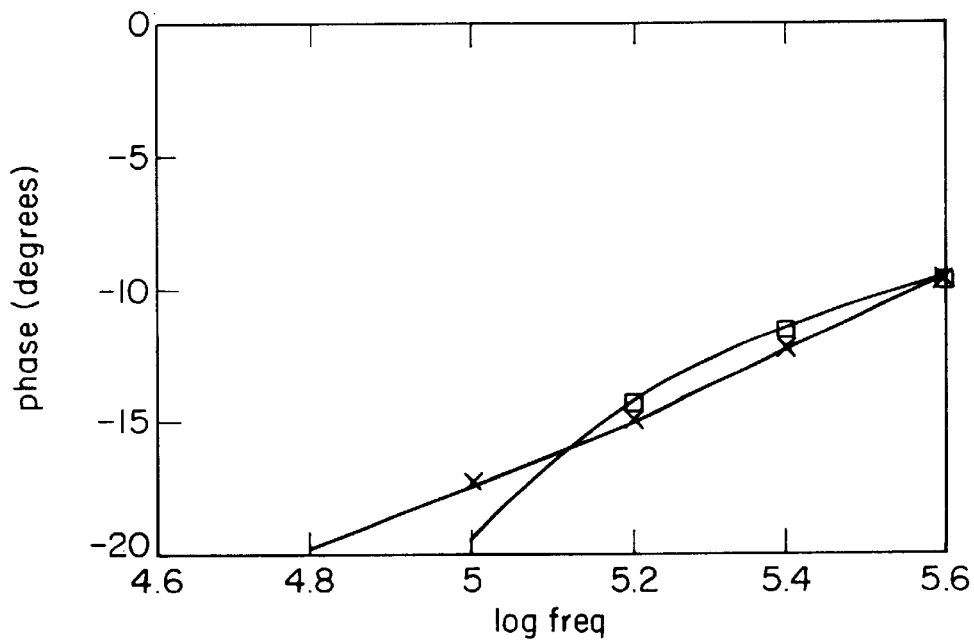

An experimental demonstration of this effect is provided in FIGS. 31(a–b) and FIGS. 32(a–b). The experimental measurements are indicated by crosses and squares for the two different copper foils. The micrometer measured thickness, Δ, is indicated for each foil; and a conductivity of 5.49E7 mhos/m was used in the simulations that are indicated by solid lines. This value of conductivity is the actual value measured for the thinner foil—a demonstration of this measurement will follow. Excellent agreement is demonstrated for frequencies above the impedance analyzer 14 threshold frequency at about 100 KHz. Magnitude measurements are possible below this frequency, but accuracy is limited for transinductance magnitudes below 0.05 Ω. Better agreement for the thicker foil would be possible if its conductivity were also estimated and used in the simulations.

Now, SVD is performed on the Jacobian for foils at a prescribed height of 0.4 mm, a drive frequency of 1.58 kHz, and for an Inter-Meander Magnetometer wavelength, $\lambda$=12.7 mm. The results are summarized in FIGS. 37(*a–b*) and FIGS. 38(*a–b*)for aluminum and copper foils, respectively.

As stated earlier, the condition number, c, provides a measure of the selectivity for a two-parameter estimation application. It also indicates the relative sensitivity of the two orthogonal modes associated with the singular vectors. For very thin layers (below 0.1 mm), the conditional number approaches Zero for both copper and aluminum foils. This implies that an unobservable mode exists. This mode is associated with the minimum singular value, $\sigma_{min}$, and has the associated right singular vector $[0.7—0.7]^T$. This is exactly what physical intuition would have predicted. For foils that are very thin compared to the imposed wavelength a perturbation in the unknown vector along the indicated right singular vector would produce no change in the surface conductivity, $\sigma_s = \sigma\Delta$ of the foil. The next section provides a demonstration of surface conductivity estimation using a multiple frequency nonlinear least squares algorithm.

It is important to note, however, that the largest sensitivity to measurement of either foil conductivity or thickness, when the other property is given, occurs at $\Delta$=0.12 mm, where $\sigma_{max}$ reaches a maximum—for aluminum foils with conductivity near 3.72E7 mhos/m, and at $\Delta$=0.07 mm—for copper foils with conductivity near 5.8E7 mhos/m.

For thick layers, $\Delta$ above 0.6 mm, the singular vectors indicate that the thickness of the foil is essentially unobservable. However, excellent sensitivity to foil conductivity is sustained indefinitely, as the thickness increases. This is consistent with the observation that when the upper surface of the foil is farther and farther away from the sensor, the measured transinductance should become insensitive to thickness variations.

For thickness between 0.2 and 0.6 mm for $\sigma$=3.72E7 mhos/m, and between 0.15 and 0.5 mm for $\sigma$=5.8E7 mhos/m, the transition between singular modes indicated by the right singular vectors is gradual between $[0.7—0.7]^T$ and $[1\ 0]^T$, and between $[0.7\ 0.7]^T$ and $[0\ 1]^T$. The crossing of the two singular modes associated with constant conductivity-thickness product, $[0.7—0.7]^T$, and maximum sensitivity of the conductivity-thickness product $[0.7\ 0.7]^T$ is also associated with a shifting in dominant behavior from the imposed wavelength to the shorter wavelength excitations.

The singularity points at 0.39 mm for aluminum and 0.32 mm for copper are coincident with the reversal in the variation of the Transinductance phase indicated in FIG. 29.

Two actual measurements are now demonstrated for copper and aluminum foils with thicknesses near the peak in the condition number. An expansion of the parameter space about a preliminary estimate of the operating point is provided for the two measurements in FIG. 35 and FIG. 36. The estimated foil conductivity and thickness are indicated. As a rough check of the foil thickness measurement, a micrometer measurement is provided for comparison. The error in the micrometer measurement is about 15 μm. The estimated values for foil thickness are in excellent agreement with the micrometer measured values in both cases. The conductivity estimates are also reasonable for copper and aluminum.

Multiple Frequency Measurement of Conductivity-Thickness Product

A demonstration of the measurement of the surface conductivity and height of a thin metal foil above the sensor is provided for several foils using a multiple frequency nonlinear least squares parameter estimation algorithm. This demonstration addresses applications for which δ>>Δ and the selectivity (condition number) for conductivity and thickness is much less than one 1. No attempt is made to optimize this multiple frequency measurement.

A modified Newton's method is automated for parameter estimation. This method incorporates calculation of transinductance magnitude and phase as a function of frequency, obtained from the response prediction algorithms. Estimates of physical and geometric properties can be obtained through iterative minimization of the least square error in the magnitude and phase summed over all frequencies. Updates of parameters are obtained using values of the function, its gradient (Jacobian), and its Hessian (second derivative matrix). The correction is chosen in the "Newton Direction" according to $$\overline{\theta}^{(i+1)} = \overline{\theta}^{(i)} + \alpha f^{(i)} \qquad (59)$$

$$f^{(i)} = -[V''(\overline{\theta}^{(i)})]^{-1} V'(\overline{\theta}^{(i)}) \qquad (60)$$

Where $\theta^{(i)}$ is the $i^{th}$ set of predicted parameter values, $f^{(i)}$ is a search direction derived from values of the function V(θ) (in our case, the vector of errors in magnitude and phase at each frequency) at previous iterations, α is a positive constant set to obtain an appropriate decrease in the value of V(θ). The parameter estimation programs incorporate a package developed by Argonne National Laboratory, Minpack Project in 1980. This package uses a modified Levenberg-Marquardt method (also called Marquardt method) in which the steepest descent method is used far from the minimum and then smooth transition to the inverse Hessian method occurs as the minimum is approached (L. Ljung, System Identification: Theory for the User, Prentice-Hall NH (1987); W. H. Press et al., Numerical Recipes, The Art of Scientific Computing, Cambridge U. Press (1986)). In the modified method used here, both the Hessian and the Jacobian are estimated from the function values, V(θ), since no analytical form is available. In the inverse Hessian method, the Hessian of the error vector is used to adjust α in Eq. 59.

Figure 37A:
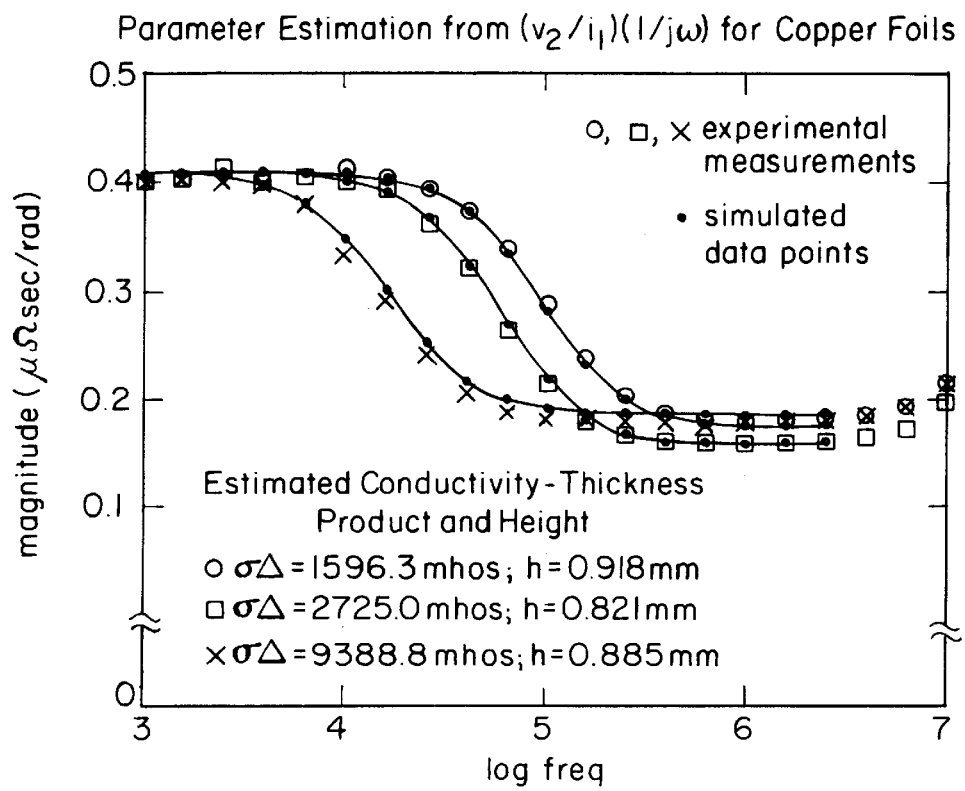
FIGS. 37(a–b) are plots of the trans-inductance magnitude and phase measured with the Inter-Meander Magnetometer prototype and predicted by the continuum model for three different copper foil thicknesses.
Figure 37B:
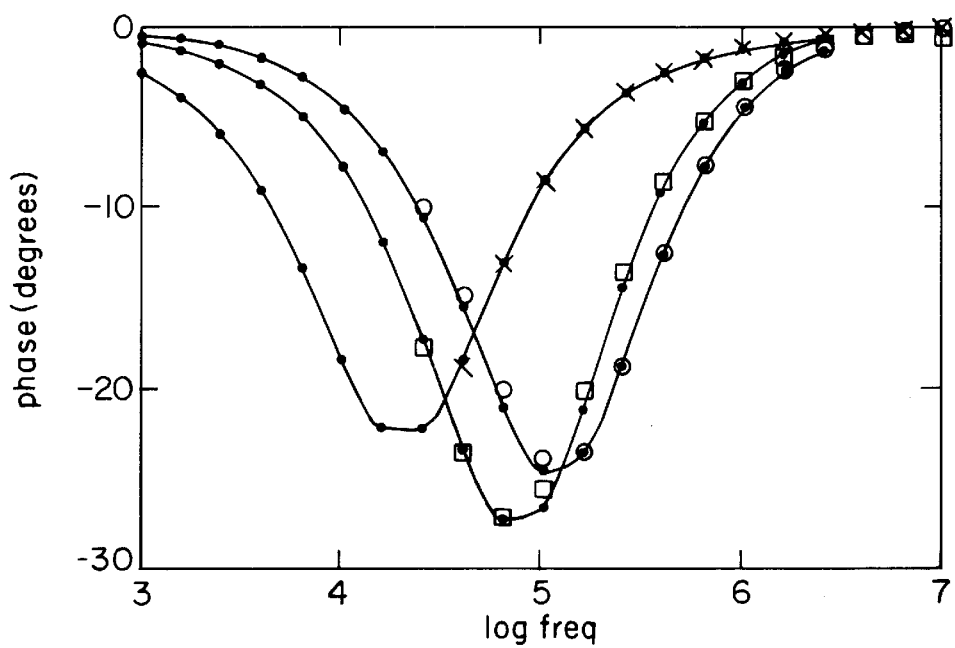
Figure 38A:
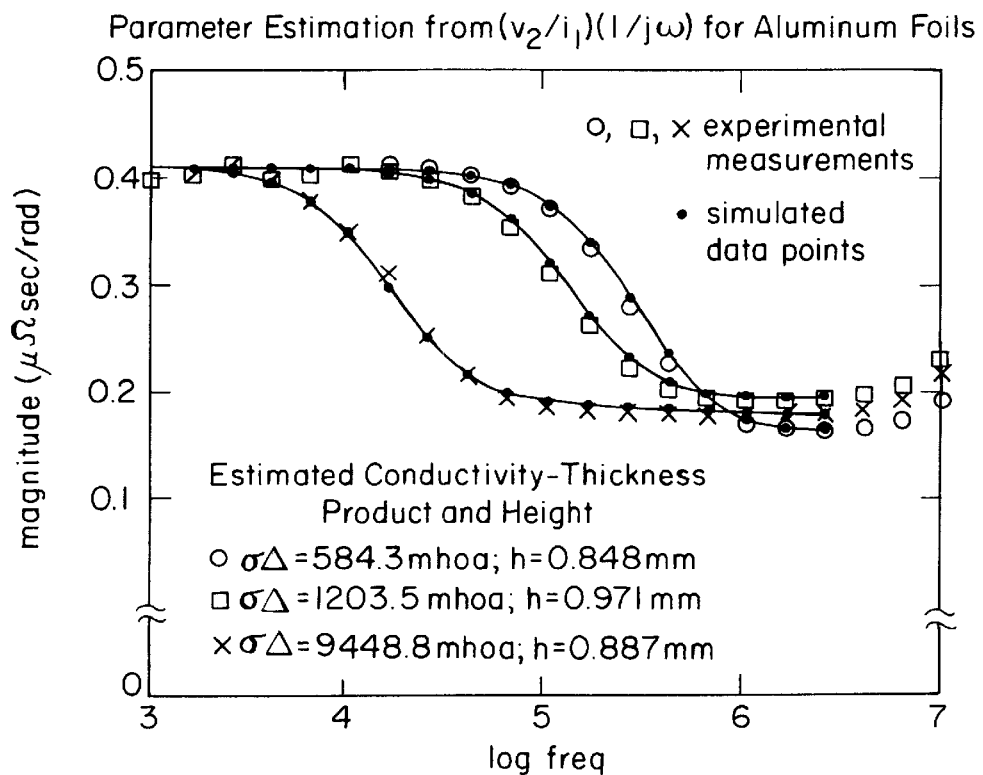
FIGS. 38(a–b) are plots of the trans-inductance magnitude and phase measured with the Inter-Meander Magnetometer prototype and predicted by the continuum model for three different aluminum foil thicknesses.
Figure 38B:
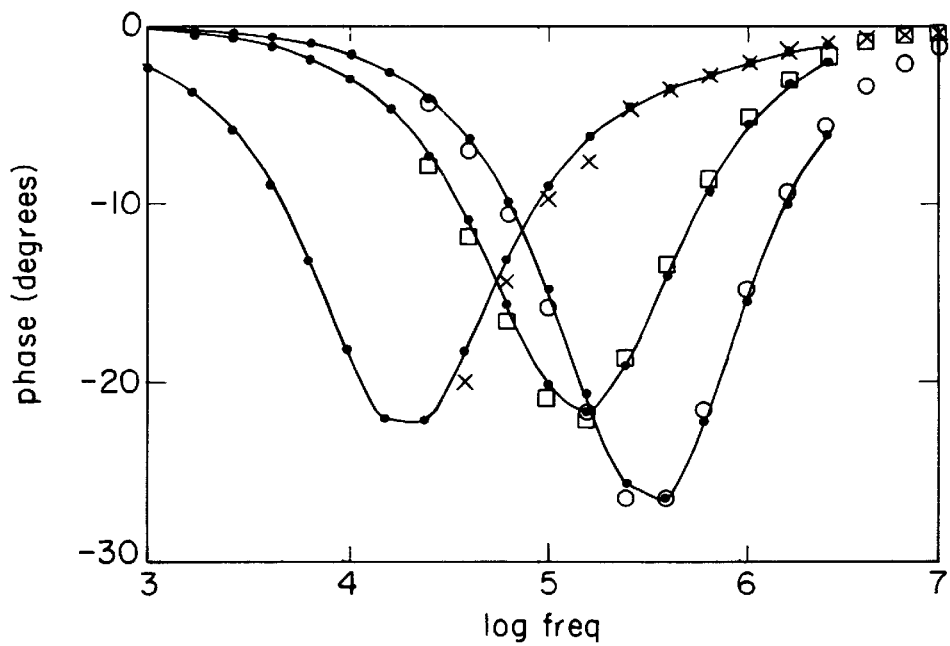

The results for six different foils are presented in FIGS. 37(*a–b*) and FIGS. 38(*a–b*). For the thicker foils, the condition number has increased sufficiently to require a more robust estimation approach. In other words, for the thicker foils, it is necessary to adjust σ and Δ independently to achieve better agreement between the simulated and experimental response.

At this point it is important to emphasize that all measurements described here are both uncalibrated and absolute.

The consistent agreement between simulated and experimental data provides further support for this claim. The capability to measure absolute physical and geometric properties without calibrations will provide significant cost and performance benefits to many applications.

Conductivity and Height Measurement for Thick Conducting Plates

The independent measurement of conductivity and height is a common requirement in eddy current sensors applications. However, the extremely high sensitivity of measurements to the height of a MUT often prevents accurate conductivity measurements. This is especially the case when calibration must be used and accurate location of the sensor is difficult.

In this section, the SVD-based measurement optimization techniques presented earlier are used to provide accurate independent measurement of the conductivity and height (lift-off) for relatively thick metal plates.

Figure 39A:
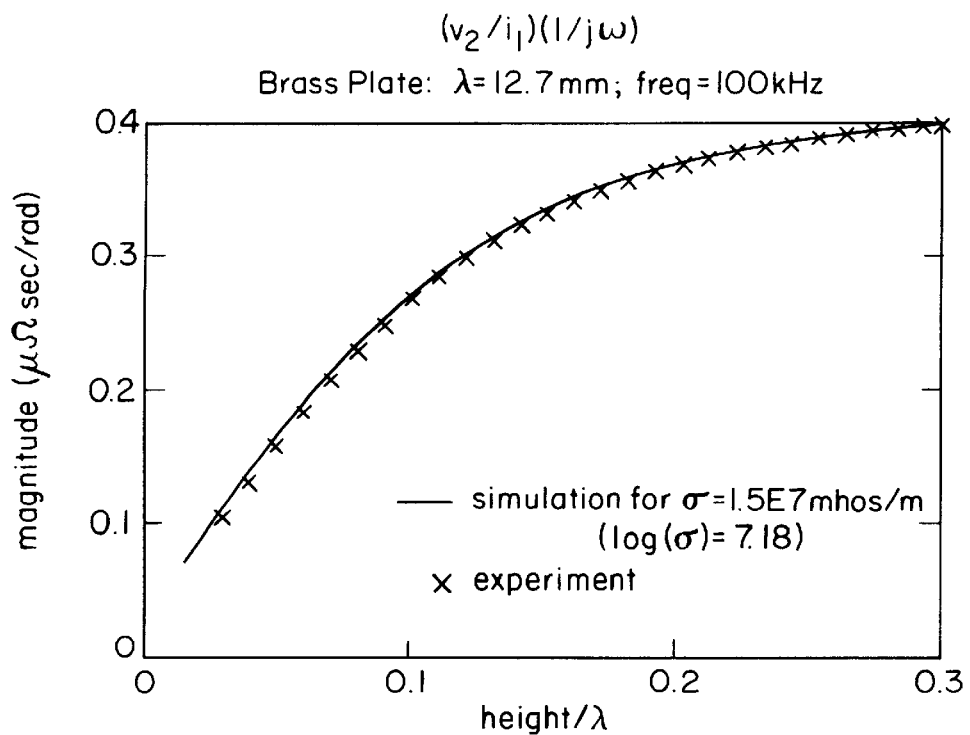
FIGS. 39(a–b) are plots of the trans-inductance magnitude and phase measured with the Inter-Meander Magnetometer prototype and predicted by the continuum model for a brass plate at several different heights above the winding plane.
Figure 39B:
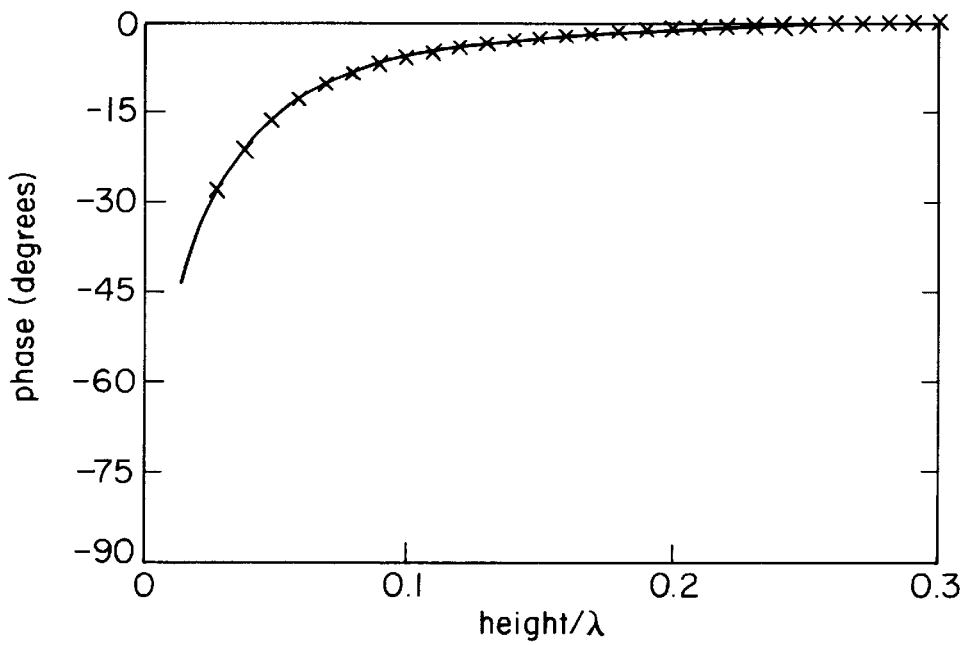

First, a comparison of simulated and experimental data is provided in FIGS. 39(a–b) for a brass plate at various heights above the sensor. In this case, the conductivity was adjusted in the simulations to obtain visual agreement with the experimentally measured phase.

SVD is now performed on the new Jacobian. Plots of the condition number and associated singular values and singular vectors as a function of height and conductivity are provided in FIGS. 40, 41(a–b) and 42(a–b). For good conductors, such as brass, aluminum and copper, the measurement shows excellent dynamic range and would permit sorting of a wide range of conducting materials located for this example at an unknown height between 0.03 mm and 0.5 mm.

Figure 43:
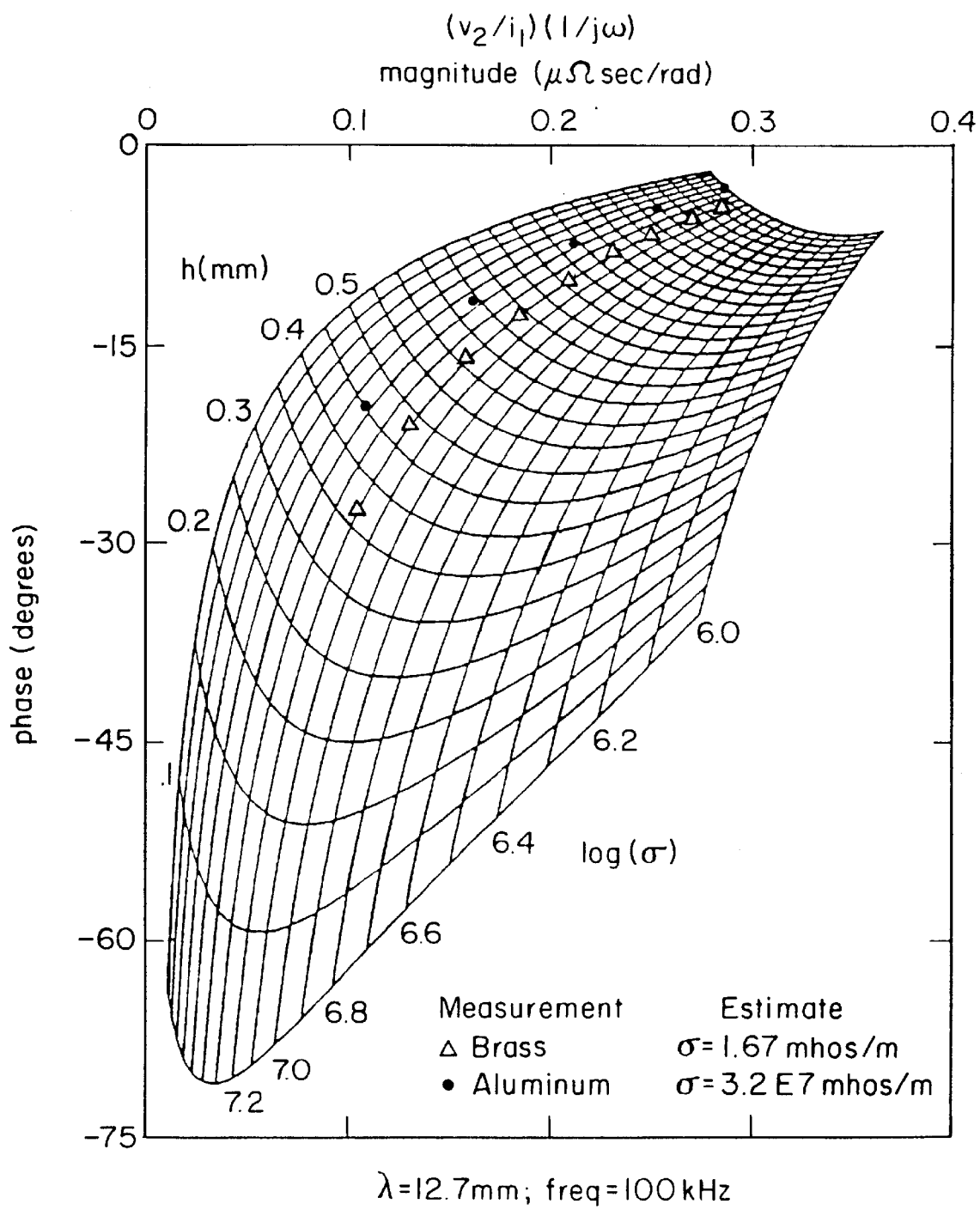
FIG. 43 is a two-dimensional parameter estimation grid for measurement of conductivity and air-gap height for very thick conducting layers.

Finally, the independent measurement of height and conductivity is demonstrated in FIG. 43 for an aluminum and brass plate with no calibration. The experimental data points for each plate trace out a line of constant conductivity. This provides strong support for the claims of absolute uncalibrated measurement of conductivity.

It is important to note that the multiple height measurement provides a single frequency multiple measurement approach. This will enable accurate measurement of conductivity in applications for which the conductivity is dispersive (i.e., $\sigma$ varies with frequency). This should have direct application in crack detection and aging/fatigue monitoring in metal plates, foils and pipes. This provides a simple alternative to the multiple wavelength approach (J. R. Melcher, application Ser. No. 325,695 (1989), allowed, for a continuation of patent) to property estimation and can also be applied to magnetic media.

Height Measurement for High Permeability Layer

In this section, a brief evaluation of measurement performance and design issues is provided for the measurement of height for a high permeability layer.

SVD results are provided in FIG. 44 for a highly permeable layer at various heights above the sensor. In this example, the condition number is always zero. This is consistent with the fact that the phase is zero with no ground plane and zero bulk conductivity, so that only the magnitude provides useful measurement information. With a back-plane it may be possible to estimate both the height and the permeability.

The optimal sensor position for measurement of small variations in layer height is approximately 0.2 mm for this example.

A wide range of potential sensor design variations is possible to enhance the sensitivity to height measurement. For demonstration purposes, a conducting back-plane (ground-plane) is introduced at 0.5 mm below the sensor. The proximity of this back-plane to the winding plane could be optimized using the SVD-based methods described earlier. This optimization is not provided here. The variation in the magnitude of the Transinductance with and without this ground plane for different heights of the highly permeable layer is demonstrated in FIGS. 45a and 45b.

The measurement of transimpedance, $v_2/j\omega i_1$, is demonstrated at 1 MHz for an infinite half space of a highly permeable material ($\chi_m$=1E3, $\sigma$=0.1 mhos/m—for example, a sintered powder) at the height $h_a$ (2) above the magnetometer surface. A significant increase in sensitivity for close proximity height measurement is apparent when the ground plane is present. Measurements are possible with the HP LF 4192 Impedance Analyzer at 1 MHz; however, with the back-plane, these measurements could not easily be made below 100 KHz. Without the back-plane, measurements can typically be made as low as 20 KHz with the available instrumentation for the original winding construct from FIG. 21.

Figure 46A:
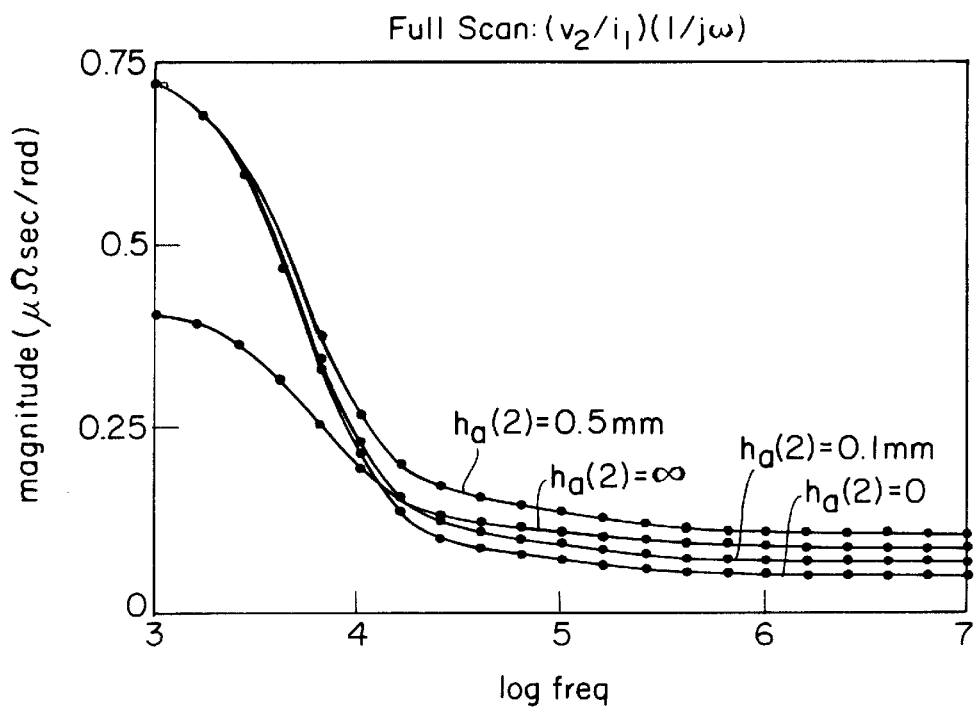
FIGS. 46(a–b) are plots of the trans-inductance variation with temporal excitation frequency with a high permeability layer at various heights above the winding plane, with a back-plane at 0.5 mm below the winding plane.
Figure 46B:
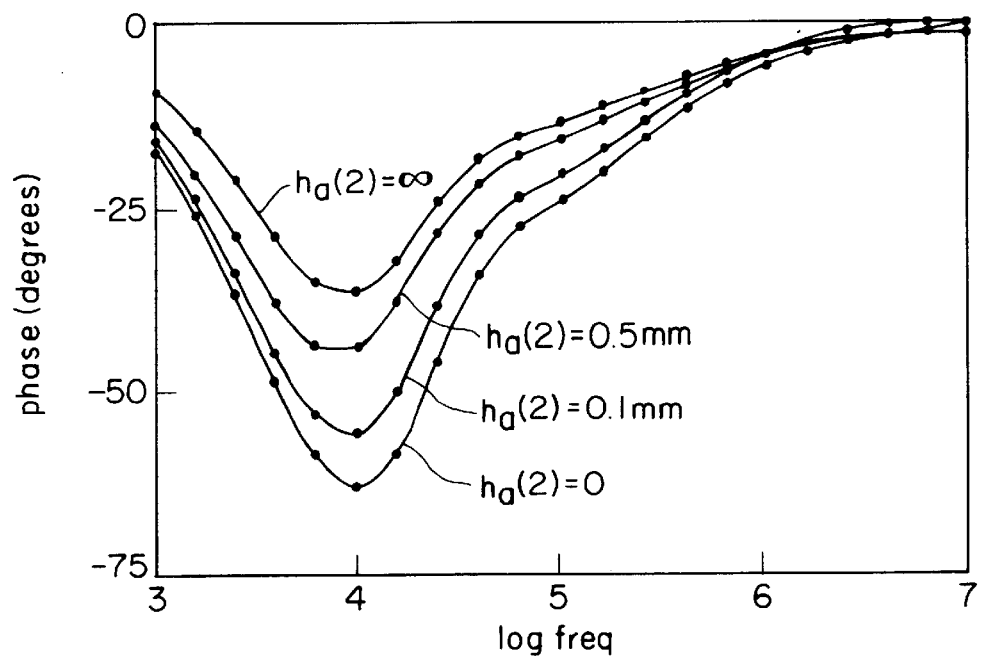
Figure 47A:
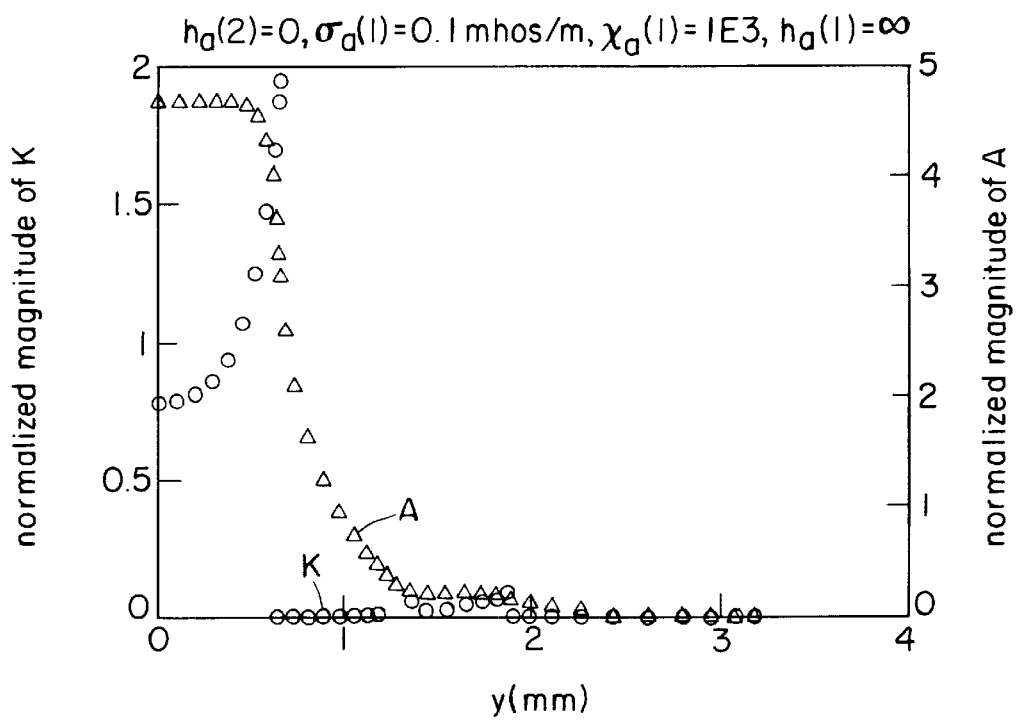
FIGS. 47(a–b) are plots of the surface current density distribution, o, and the magnetic vector potential distribution, Δ, over the first quarter wavelength of an Inter-Meander Magnetometer with the original construct, as predicted by the continuum model, with a high permeability layer immediately above the winding plane.
Figure 47B:
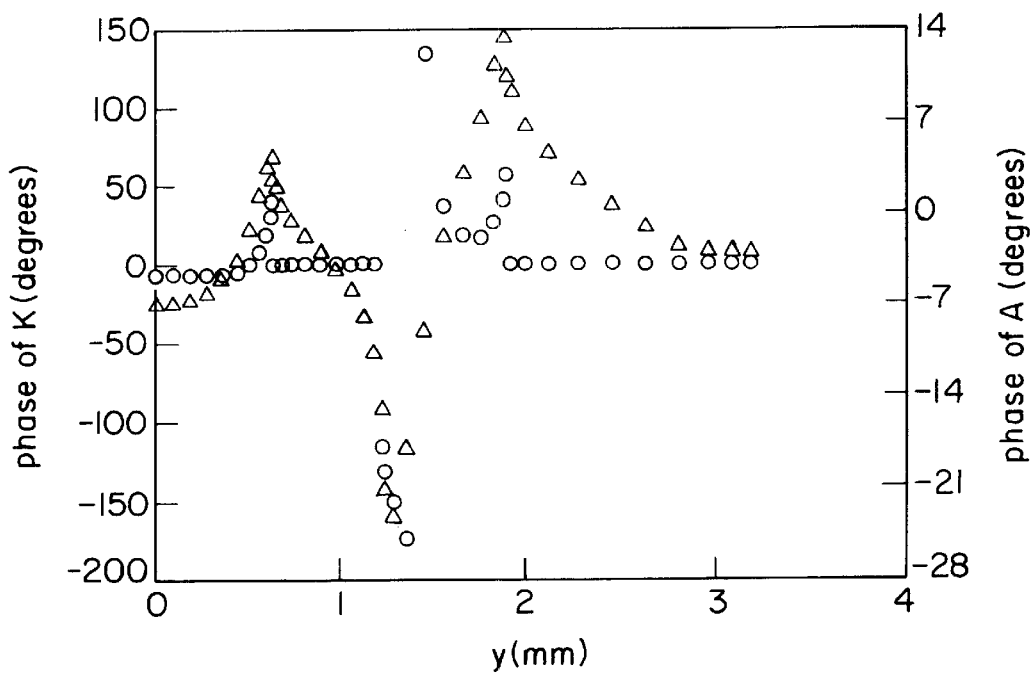
Figure 48A:
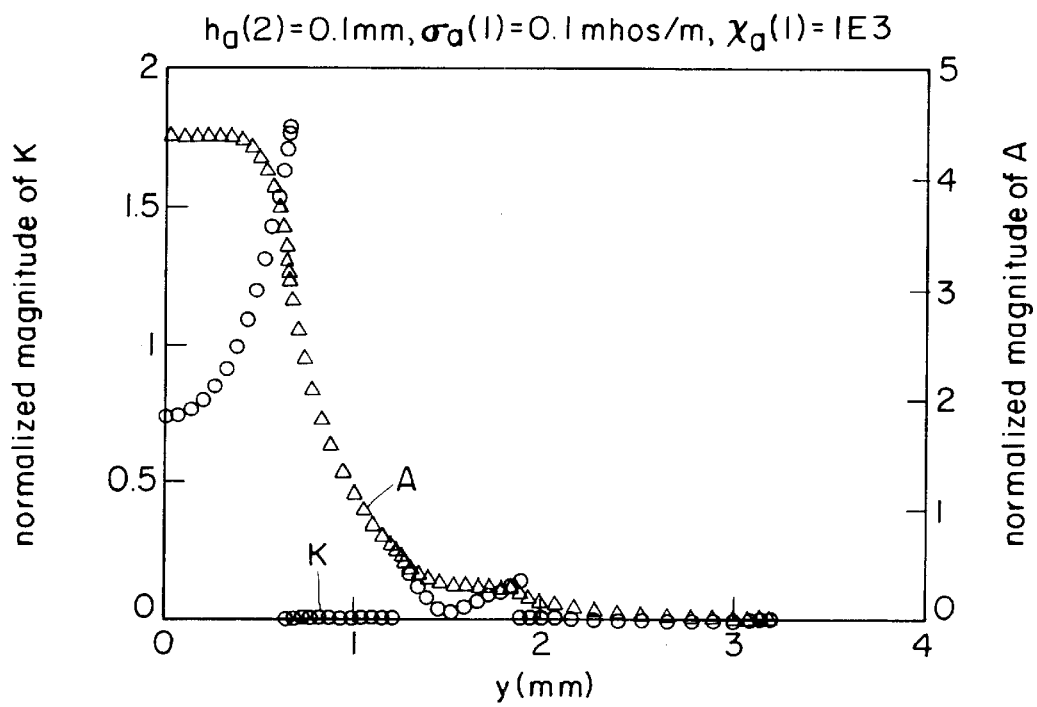
FIGS. 48(a–b) are plots of the surface current density distribution, o, and the magnetic vector potential distribution. Δ, over the first quarter wavelength of an Inter-Meander Magnetometer with the original construct, as predicted by the continuum model, with a high permeability layer 0.1 mm above the winding plane.
Figure 48B:
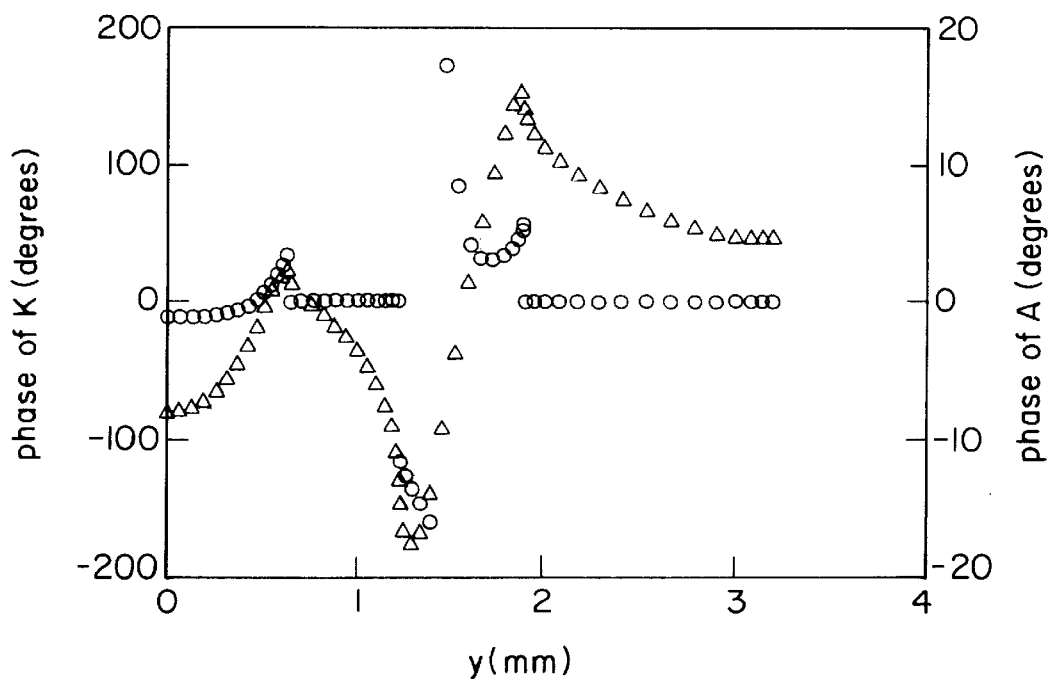
Figure 49A:
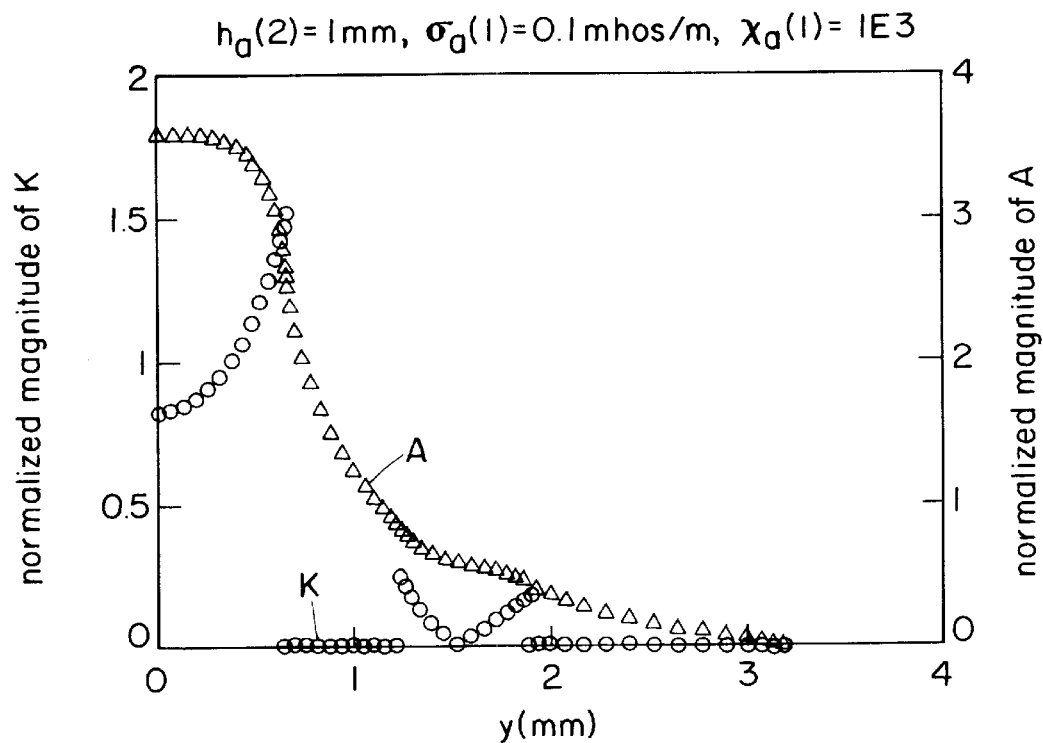
FIGS. 49(a–b) are plots of the surface current density distribution, o, and the magnetic vector potential distribution, Δ, over the first quarter wavelength of an Inter-Meander Magnetometer with the original construct, as predicted by the continuum model, with a high permeability layer 1 mm above the winding plane.
Figure 49B:
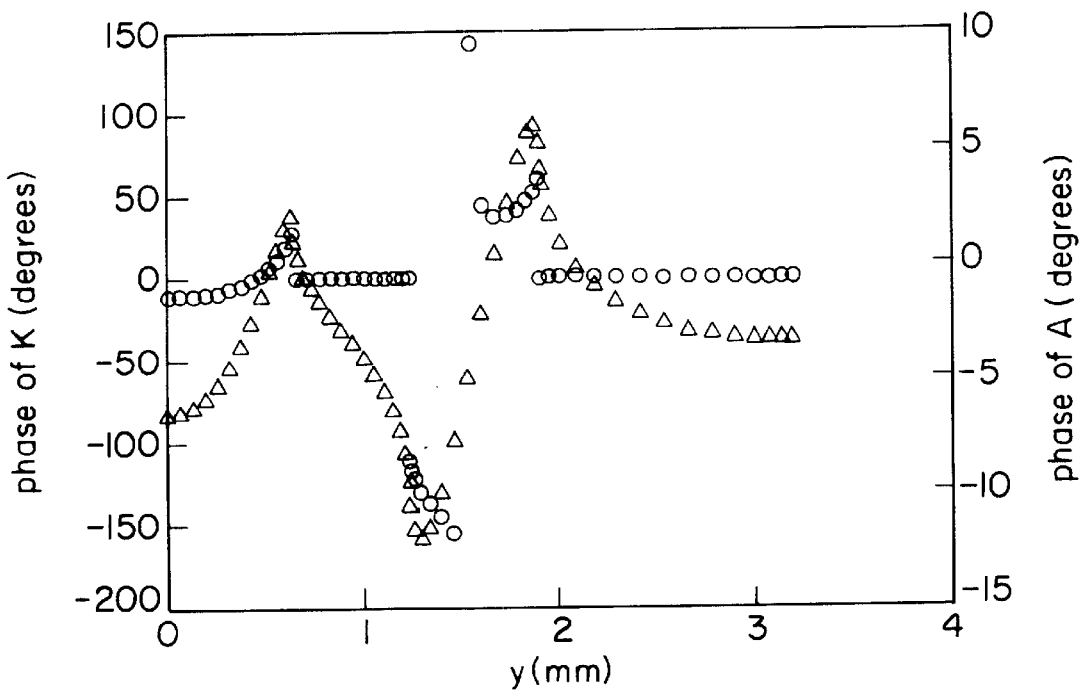

A look at the frequency response corresponding to different heights of the highly permeable media, FIG. 46, demonstrates the relevance of span-wise diffusion. The bucking out of the phase at about 1 MHz and the reversal of the magnitude dependence on $h_a$ (2) are directly related to the span-wise diffusion. It is always a good idea to check the performance of the computer simulations by plotting the spatial variations of current and vector potential. These plots are provided in FIGS. 47(a–b), FIGS. 48(a–b) and FIGS. 49(a–b). Variations in the distribution of the currents in the secondary, and more subtly in the primary, are shown in these three figures. The current at each collocation point is denoted in these figures by o, and the vector potential by Δ.

Single Frequency Estimation of Complex Permeability

Figure 50:
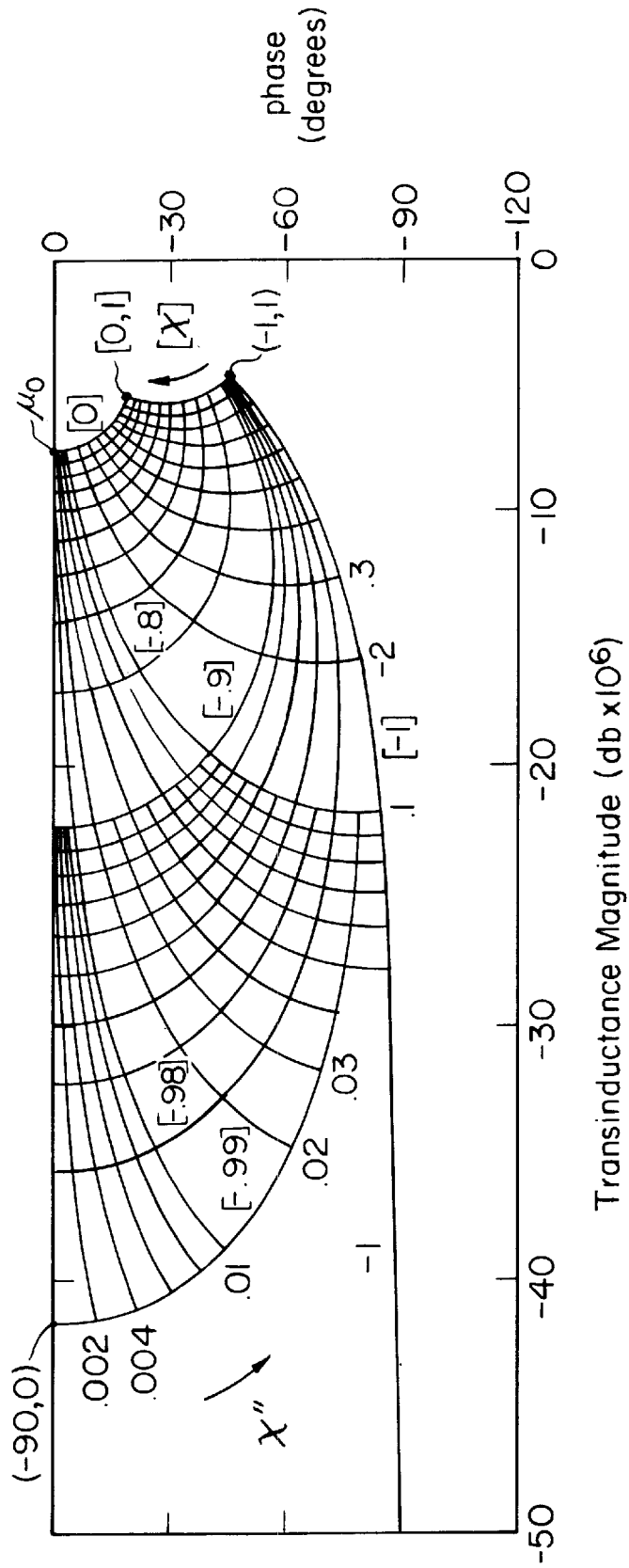
FIG. 50 is a universal transinductance plot for a diamagnetic infinite half space used as a two-dimensional property estimation grid for the complex magnetic susceptibility.

The estimation of complex magnetic susceptibility is demonstrated in this section for dispersive media with no significant bulk conductivity. The span-wise diffusion continuum model provides predictions of the response for any layered media with completely specified properties. The media selected for this demonstration is a thick layer of granular aluminum (≅1 mm particle radius) placed at two different heights above the sensor windings. This measurement is ideal for parameter estimation, since with no ground plane and no significant bulk conductivity, the universal transinductance plot in FIG. 50 can be used to graphically estimate the complex magnetic susceptibility for the granular aluminum layer. The universal plot and the fact that the transimpedance is an analytic function of the complex magnetic susceptibility permit graphical estimation at any frequency from a single "universal" plot.

In this plot, the magnetometer response, $v_2/j\omega i_1$, is plotted for a grid of complex permeability values ($\chi_m=\chi'-j\chi''$). The lines of constant $\chi'$ and $\chi''$ are always orthogonal because $V_2/j\omega i_1$, is an analytic function of $\chi_m$. This orthogonality is exhibited in the figure by consistently scaling the magnitude and phase axis in accordance with the logarithm of the complex transimpedance (M. C. Zaretsky, et al. Continuum properties from Interdigital Electrode Dielectrometry, IEEE Transactions on Electrical Insulation, Vol. 23, No. 6, Pp. 899–917, Dec. 1988).

The parameter estimation methodology is initiated with a first guess obtained visually from the universal transinductance plot. The secant method is then used in a root searching procedure to minimize the error, e*(θ*), between the experimentally measured transimpedance, $v_2/j\omega i_1$, and the predicted transimpedance (M. C. Zaretsky, et al. Continuum properties from Interdigital Electrode Dielectrometry, IEEE Transactions on Electrical Insulation, Vol. 23, No. 6, Pp. 899–917, Dec. 1988; L. Lyung, System Identification: Theory of the Use, Prentice Hall, Inc., NH, 1987). The parameters, $\theta^*_i$, are updated by $\Delta\theta^*_i$ by forming a secant using the most recent two guesses. The fact that the transimpedance is an analytic function of the complex magnetic susceptibility permits the direct use of the secant method with parameter updates determined from (M. C. Zaretsky, et al. Continuum properties from Interdigital Electrode Dielectrometry, IEEE Transactions on Electrical Insulation, Vol. 23, No. 6, Pp. 899–917, Dec. 1988).

$$\Delta\theta^*_i = \frac{e^*(\theta^*_i)}{\left(\frac{e^*(\theta^*_i) - e^*(\theta^*_{i-1})}{\theta^*_i - \theta^*_{i-1}}\right)} \quad (61)$$

Parameter estimation of dispersive complex permeability is now demonstrated for the diamagnetic granular aluminum layer. The initial estimate of the derivative is obtained by simulating a second guess with a 2% variation in the real and imaginary parts of $\chi_m$. The magnitude and phase of the trans-impedance, $v_2/j\omega i_1$, is obtained experimentally using the HP LF 4192 Impedance Analyzer. In order to demonstrate absolute measurement for layered media, a 2 cm layer of granular aluminum is measured for two different heights, $h_a$ (3)=0 and $h_a$ (3)=0.8 mm, above the magnetometer windings. FIG. 51a provides the experimental measurement of trans-impedance magnitude and phase at each frequency and height (note: the precision of the phase measurement with the HP LF 4192 Impedance Analyzer increases incrementally with the magnitude of the trans-impedance). The input to the parameter estimation is the first guess for the real and imaginary parts of $\chi_m$ at each frequency. The program then provides updated predictions for the $\chi_m$ determined from Eq. 61. The first guess and resulting estimates for this example are provided in FIG. 51b.

Figure 52A:
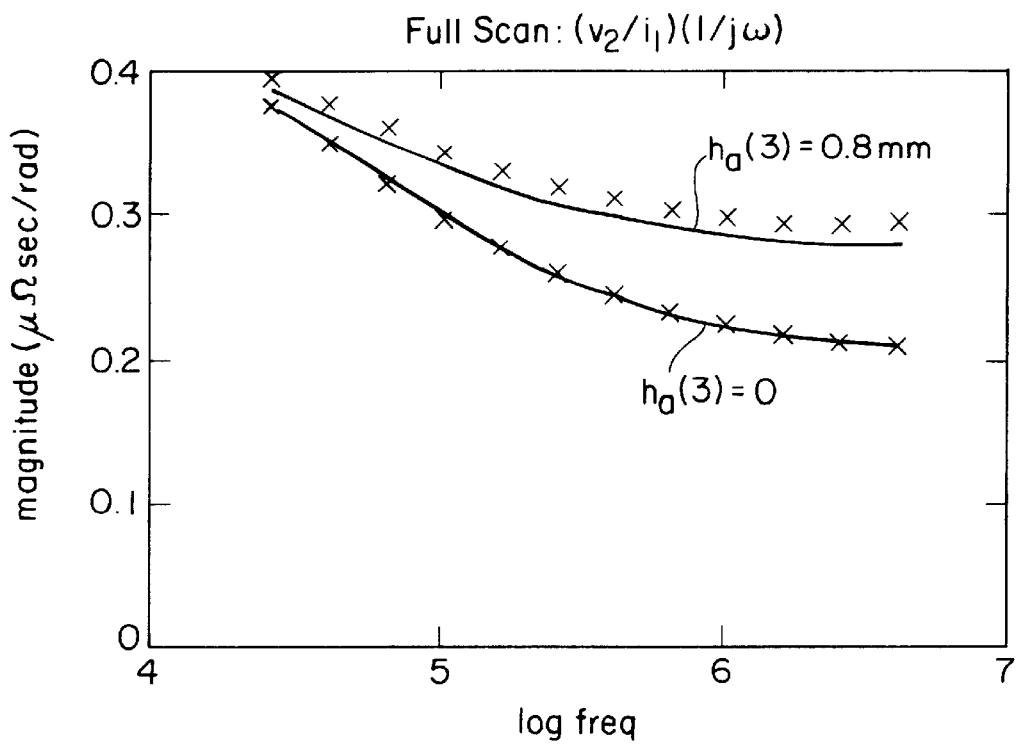
FIGS. 52(a–b) are plots of the experimental (crosses) and predicted (curved line) responses of the transinductance magnitude and phase as a function of the temporal excitation frequency.
Figure 52B:
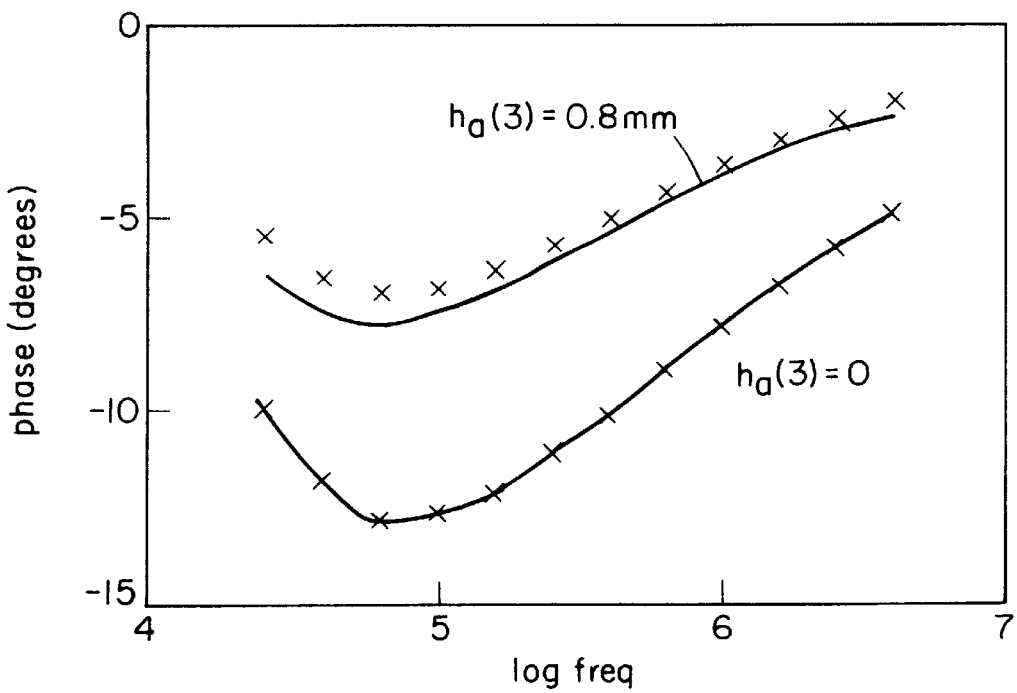

The estimated $\chi_m$ in FIGS. 51(a–b) are now used to predict the response of the sensor with the granular aluminum layer at 0.8 mm above the sensor (note: the estimated aggregate setup error is about 10% for the height above the sensor and possible variations in coverage of the active sensor region with a consistent layer of granular aluminum). FIG. 52 shows the experimental and predicted responses for the two cases ($h_a$ (3)=0 and $h_a$ (3)=0.8 mm) using the estimated values of $\chi_m$ from Table 3. Of course, the predicted and measured responses are identical for $h_a$ (3)=0 since the parameter estimation routines were run for this MUT height. For $h_a$ (3)=0.8 mm, the predicted response is well within the estimated 10% setup error. This result provides solid verification of the algorithms and parameter estimation methodology.

Further verification is obtained by comparison with an analytical model of conducting spheres built up from a magnetic dipole representation. If the effects of contact between the spheres is neglected, a model derived by Inkpen and Melcher (S. L. Inkoen and J. R. Melcher, Smoothing the Electromagnetic Heating Pattern In Polymers," Mid-April 1985, Vol. 25, No. 5, Pp. 289–294) applies directly. This model also neglects the effect of the fields induced in one sphere on the fields induced in neighboring spheres. Thus, some disagreement between this model and the actual measurements is expected. In the Inkpen/Melcher model, it is assumed that the skin depth is small compared to the radius of the spheres. The skin depth for aluminum at 100 KHz is approximately 0.3 pk mm compared to an average particle radius of approximately 1 mm. This model results in the following relation for the complex magnetic susceptibility in terms of the volume fraction of particles, $V_pN$, the particle radius, a, the drive frequency, ω, and the conductivity and permeability of the particles σ, μ

$$\chi^*_m = \frac{-\left[NV^*_p(1+NV_p/2)\frac{\mu_o^2 a^2 \sigma}{\mu}\right]\omega - j\left[NV_p\mu_o a\sqrt{\frac{\sigma}{2\mu}}\right]\omega^{1/2}}{1+\left[\frac{2\mu_o^2 a^2 \sigma}{9\mu}(NV_p/2+1)^2\right]\omega} \quad (62)$$

Figure 53A:
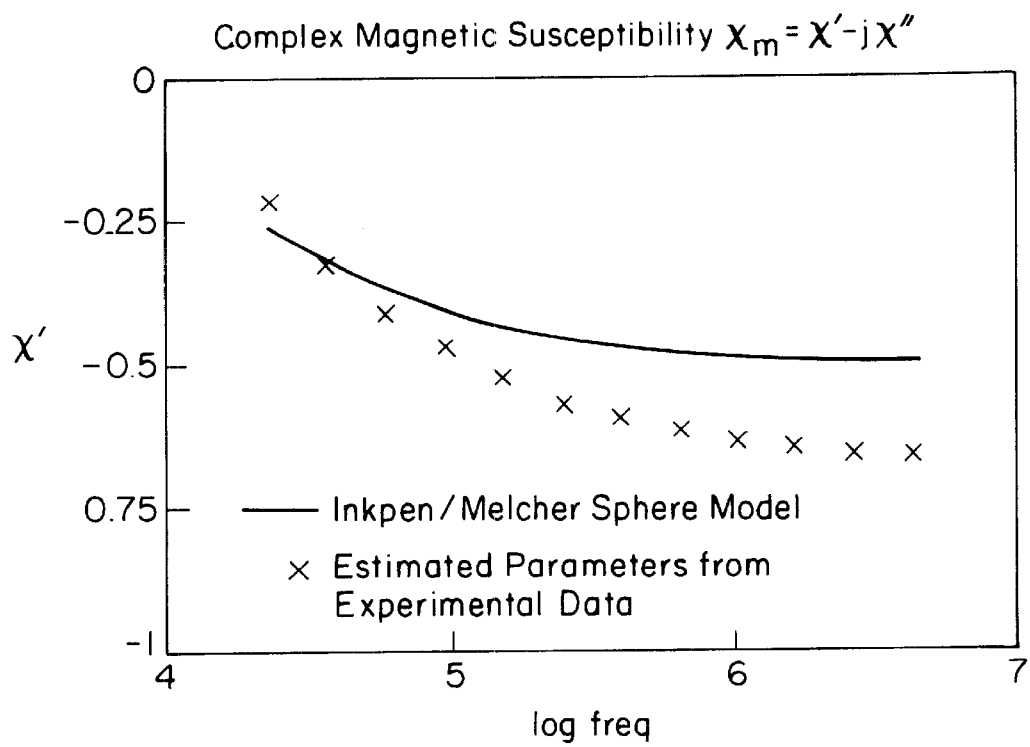
FIGS. 53(a–b) are plots of the predicted and analytically determined complex magnetic susceptibility for the granular aluminum layer.
Figure 53B:
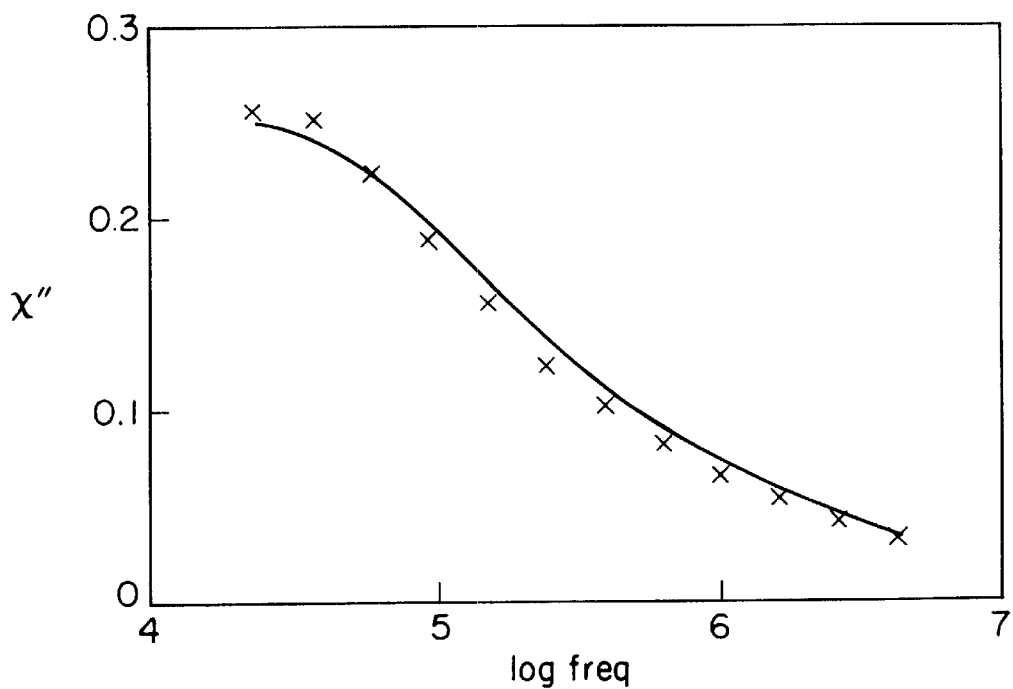

Reasonable values of these parameters for the granular Aluminum used are: a=0.9 mm, NVp=0.4, σ=2E7 mhos/m, and $\mu=\mu_o$. A comparison of the estimated complex permeability denoted by x and the Inkpen/Melcher Sphere Model is provided in FIG. 53. The agreement is again very good considering the limitations of the analytical sphere model.

The examples discussed in this section demonstrate the capability of the Inter-Meander Magnetometer and associated parameter estimation algorithms to estimate complex magnetic susceptibility for diamagnetic materials. This methodology can be applied directly to applications involving layered ferrous media. Care must be taken in that case to ensure the universality of the transimpedance plots. If universal plots are not obtainable the only adjustment in the methodology is the required use of frequency dependent trans impedance plots to obtain a first guess at each frequency.

Conductivity and Permeability Estimation for Homogeneous Infinite Half Space

The bulk conductivity introduces shape variance into the magnitude-phase plots as a function of drive frequency. Although it is possible that universal plots may exist for a properly normalized transimpedance in specific examples, obtaining a general universal plot is unlikely. Furthermore, unlike the real and imaginary parts of the complex permeability, the transimpedance can not be represented over the entire relevant parameter space as an analytic function of a complex parameter incorporating both the permeability and the conductivity (e.g., for electroquasistatics such a parameter is $\epsilon^*=\epsilon'-j\epsilon''=\epsilon-j\sigma/\omega$. However, there are regions of practical importance over which the transimpedance exhibits some of the same properties of an analytic function. This implies that all derivatives exist and are continuous at all points in the region; satisfaction of the Cauchy-Riemann equations is also a necessary condition for analyticity (R. V. Churchill, and G. W. Brown, "Complex Variables and Applications", McGraw-Hill, NY, 1984; F. B. Hildebrand, "Advanced Calculus for Applications", Prentice-Hall, N5, 1976). The graphical analog states that in regions of analyticity with respect to a complex parameter space the magnitude vs. phase plot will always exhibit orthogonality between lines of constant real part and lines of constant imaginary part. In the case discussed here, the magnitude vs. phase plot for conductivity and permeability does approach this property for certain parameter space regions.

Figure 54:
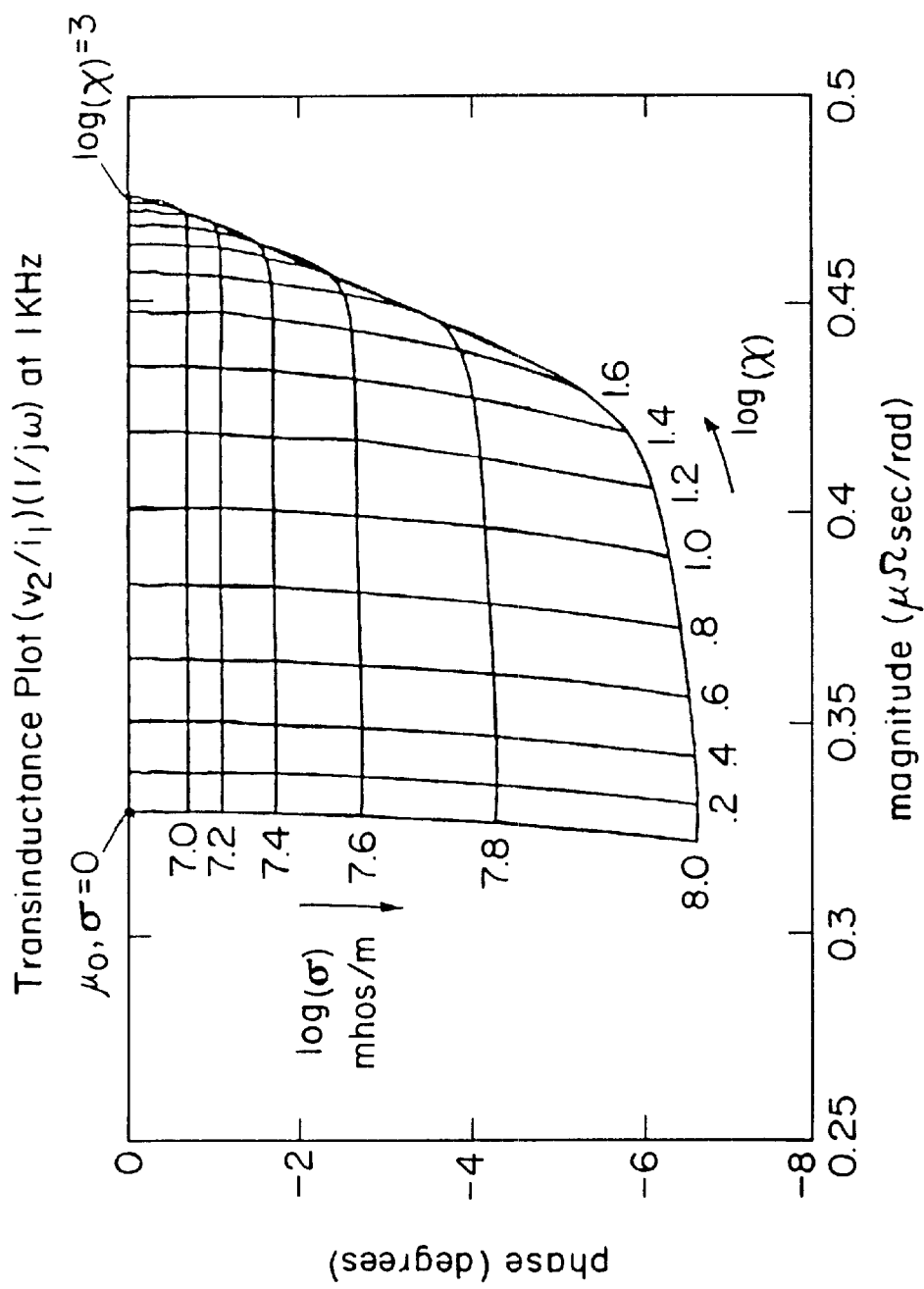
FIG. 54 is a plot of a two-dimensional property estimation grid for conductivity and permeability for the Inter-Meander Magnetometer, with no back-plane, at 1 KHz.
Figure 55:
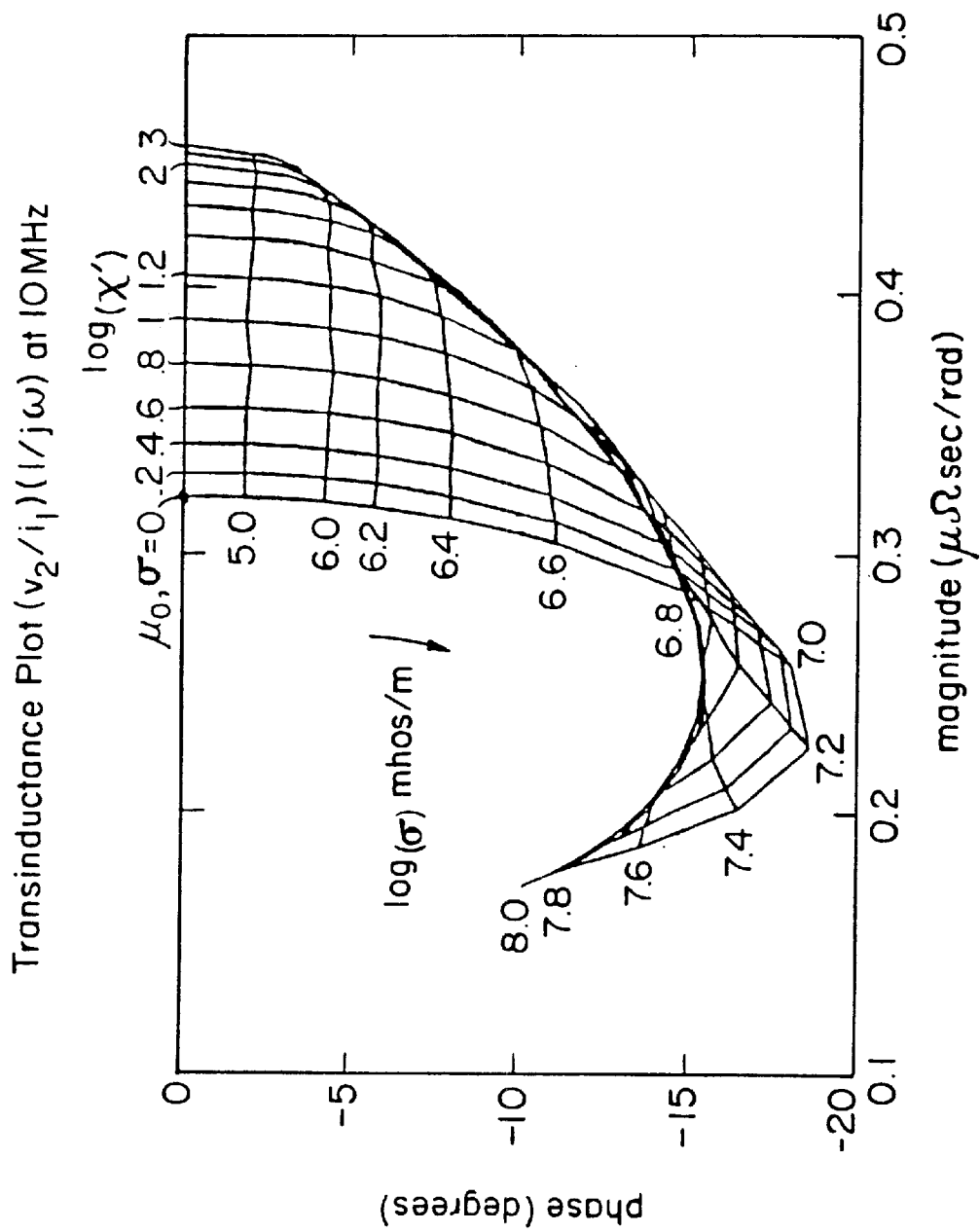
FIG. 55 is a plot of a two-dimensional property estimation grid for conductivity and permeability for the Inter-Meander Magnetometer, with no back-plane, at 10 MHz.

This is demonstrated in FIGS. 54 and 55 for 1 KHz and 10 MHz. Clearly, even by scaling these plots in accordance with Eq. 51 the desired orthogonal characteristic is not exhibited over the entire relevant parameter space. The double-valued nature of the magnitude vs. phase plot at 10 MHz and the saturation of the magnitude for large values of $\mu$, $\sigma$ are related to magnetic diffusion in the MUT. Two characteristics are most apparent. First, as the permeability, $\mu$, increases, the transimpedance magnitude generally increases at a given conductivity, $\sigma$. This is the result of an increased inductive coupling between the primary and secondary windings. Second, as the conductivity increases for a given permeability, the transimpedance magnitude decreases. This is the result of a reduction in inductive coupling to the secondary due to increased shielding associated with decreasing magnetic skin depth in the measured media. In the double valued region, the skin depth, decreases significantly with $\mu$ at 10 MHz resulting in increased shielding. The result is a region over which different combinations of permeability and conductivity result in the same transimpedance magnitude and phase. The independent estimation of $\mu$ and $\sigma$ could also be optimized using the SVD-based method described earlier. This is not shown here.

Anisotropic Permeability Model

In this section, a detailed model of magnetic diffusion for media with anisotropic complex permeability is derived, and the associated transfer relations are formulated. In addition, alternative sensor design configurations are presented. The objective is to demonstrate that more complex media representations can be included in the continuum model simply by changing the media representation subroutines.

First, a permeability tensor is defined as follows:

$$\bar{\mu} = \begin{bmatrix} \mu_x & 0 & 0 \\ 0 & \mu_y & 0 \\ 0 & 0 & \mu_z \end{bmatrix} \quad (63)$$

Faraday's law with the assumption of ohmic conduction ($\vec{J} = \sigma \vec{E}$) is given by $$\nabla \times \frac{\vec{J}}{\sigma} = -\frac{\partial \vec{B}}{\partial t}; \vec{B} = \nabla \times \vec{A} \quad (64)$$

Ampere's law with anisotropic permeability introduced is $$\vec{J} = \nabla \times \vec{H} = \nabla \times (\bar{\mu}^{-1} \vec{B}) = \nabla \times [\bar{\mu}^{-1}(\nabla \times \vec{A})] \quad (65)$$

Combining these two equations gives the following:

$$\nabla \times \left[ \nabla \times \bar{\mu}^{-1}(\nabla \times \vec{A}) + \sigma \frac{\partial \vec{A}}{\partial t} \right] = 0 \quad (66)$$

Since the curl of the gradient of a scalar is zero, the expression inside the brackets can be set equal to $-\nabla \phi$. The homogeneous solution is then obtained by setting the same expression equal to zero. The following three equations result:

$$x\,dir\ 0 = \frac{1}{\mu_z}\frac{\partial}{\partial y}\left(\frac{\partial A_y}{\partial x} - \frac{\partial A_x}{\partial y}\right) - \frac{1}{\mu_y}\frac{\partial}{\partial z}\left(\frac{\partial A_x}{\partial z} - \frac{\partial A_z}{\partial x}\right) + \sigma \frac{\partial A_x}{\partial t} \quad (67)$$

$$y\,dir\ 0 = \frac{1}{\mu_x}\frac{\partial}{\partial z}\left(\frac{\partial A_z}{\partial y} - \frac{\partial A_y}{\partial z}\right) - \frac{1}{\mu_z}\frac{\partial}{\partial x}\left(\frac{\partial A_y}{\partial x} - \frac{\partial A_x}{\partial y}\right) + \sigma \frac{\partial A_y}{\partial t}$$

$$z\,dir\ 0 = \frac{1}{\mu_y}\frac{\partial}{\partial x}\left(\frac{\partial A_x}{\partial z} - \frac{\partial A_z}{\partial x}\right) - \frac{1}{\mu_x}\frac{\partial}{\partial y}\left(\frac{\partial A_z}{\partial y} - \frac{\partial A_y}{\partial z}\right) + \sigma \frac{\partial A_z}{\partial t}$$

For the Inter-Meander Magnetometer $$\frac{\partial}{\partial z} \approx 0 \text{ and } A_x \approx A_y \approx 0.$$

The magnetic diffusion equation then becomes $$-\frac{1}{\mu_y}\frac{\partial^2 A_z}{\partial x^2} - \frac{1}{\mu_x}\frac{\partial^2 A_z}{\partial y^2} + \sigma \frac{\partial A_z}{\partial t} = 0 \quad (68)$$

Now let $$A_z(x, y, t) = Re\hat{A}e^{j(\omega t - ky)} \quad (69)$$

The magnetic diffusion equation then reduces to the familiar form $$\frac{\partial^2 \hat{A}}{\partial x^2} - \gamma^2 \hat{A} = 0 \quad (70)$$

where $$\gamma^2 = \frac{\mu_y}{\mu_x}k^2 + j\mu_y\sigma\omega \quad (71)$$

As a check, this reduces to $k^2 + j\mu\sigma\omega$ for $\mu_x = \mu_y = \mu$, which is the correct expression in the isotropic case. It is useful at this point to define a new magnetic skin depth for the anisotropic permeability case. From the new $\gamma$, it follows that the skin depth is given by $$\delta = \sqrt{\frac{2}{\omega \mu_x \sigma}} \quad (72)$$

Note that $\mu_y$ cancels out.

Now the transfer relations can be derived. From $B = \nabla \times A$ and $H = \bar{\mu}^{-1}B$ $$\hat{H}_y = -\frac{1}{\mu_y}\frac{\partial \hat{A}}{\partial x}; \hat{H}_x = \frac{1}{\mu_x}\frac{\partial \hat{A}}{\partial y} = -jk\frac{\hat{A}}{\mu_x} \quad (73)$$

Solutions to the diffusion equation are of the form, (Melcher, Continuum Electromechanics, Cambridge, Mass., MIT Press, 1981)

$$\hat{A} = \hat{A}^\alpha \frac{\sinh\gamma x}{\sinh\gamma\Delta} - \hat{A}^\beta \frac{\sinh\gamma(x-\Delta)}{\sinh\gamma\Delta} \quad (74)$$

The resulting transfer relations are $$\begin{bmatrix} \hat{H}_y^\alpha \\ \hat{H}_y^\beta \end{bmatrix} = \frac{\gamma}{\mu_y} \begin{bmatrix} -\coth\gamma\Delta & \frac{1}{\sinh\gamma\Delta} \\ -\frac{1}{\sinh\gamma\Delta} & \coth\gamma\Delta \end{bmatrix} \begin{bmatrix} \hat{A}^\alpha \\ \hat{A}^\beta \end{bmatrix} \quad (75)$$

$$\begin{bmatrix} \hat{A}^\alpha \\ \hat{A}^\beta \end{bmatrix} = \frac{j}{k} \begin{bmatrix} \hat{B}_x^\alpha \\ \hat{B}_x^\beta \end{bmatrix} \quad (76)$$

Two new configurations are now proposed for measurement of geometric and anisotropic physical properties of a layer of conducting or magnetic media. The proposed apparatus might incorporate a winding construct similar to the previously discussed Inter-Meander Magnetometer structure shown in FIG. 10.

Figure 56A:
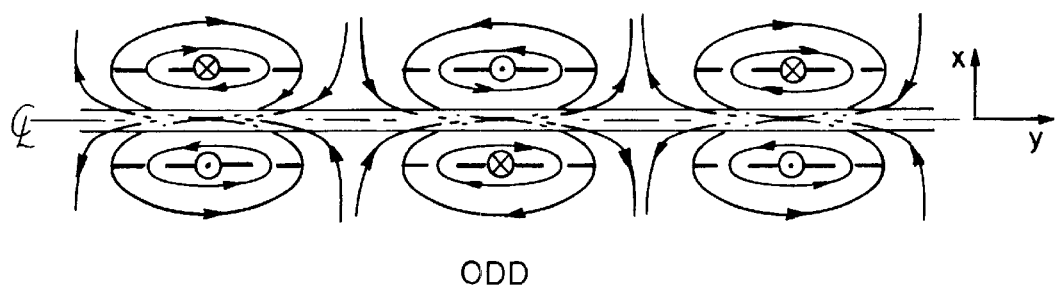
FIGS. 56(a–b) are side views of the magnetic field lines induced by two Inter-Meander Magnetometers located on opposite sides of a material under test layer, operated in the odd and even modes.
Figure 56B:
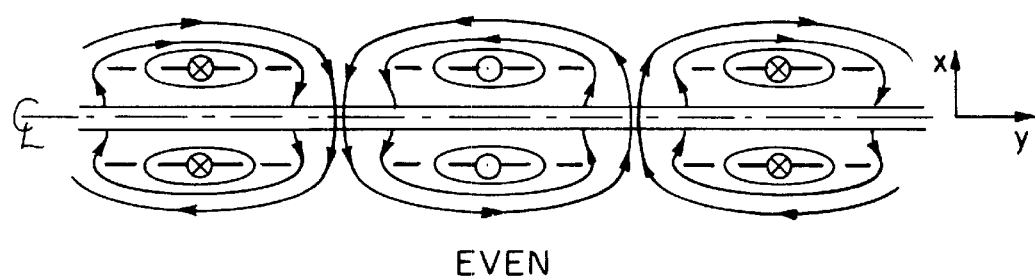

The measurement of anisotropic complex permeability ($\mu^*_y = \mu^*_x$), for example, might be accomplished with a new construct that incorporates a set of two identical Inter-Meander Magnetometer structures located above and below the layer of magnetic media. The inherent symmetry of the resulting apparatus provides for two modes of operation. Schematics of these two operating modes are provided in FIGS. 56(*a–b*). The odd mode is generated by applying the excitation currents or voltages a half wavelength out of phase, as shown in the figure. In this mode, the magnetic flux normal to the center line (in the x direction) of the thin layer is exactly zero for all y. In the even mode, the excitation is in phase, as shown, and the magnetic field intensity in the y direction at the center line of the layer is exactly zero for all y.

Information obtained from measurements in each of these modes is then combined to obtain estimates of the anisotropic property of interest. The variation of these properties as a function of an external bias field could also be considered, since the measurement is based on a perturbation of the excitation fields. The result is a localized estimate for the complex permeability.

Related Document

The present invention is related to "Uncalibrated, Absolute Property Estimation and Measurement Optimization for Conducting and Magnetic Media Using Imposed w-k Magnetometry", unpublished, by Neil Jay Goldfine which is incorporated herein by reference.

Equivalents

While the invention has been particularly shown and described with reference to preferred embodiments thereof, it will be understood to those skilled in the art that various changes in form and details may be made therein without departing from the spirit and scope of the invention as defined by the appended claims.

What is claimed is:

1. A method for generating property estimates of one or more preselected properties of a material comprising:

providing an electromagnetic structure capable of imposing a magnetic field in the material when driven by an electric signal and sensing an electromagnetic response, an analyzer for applying an electric signal to the electromagnetic structure and a property estimator for translating sensed responses into estimates for one or more preselected properties to the material;

defining a dynamic range for the preselected properties of the material;

selecting an electromagnetic winding geometry and configuration for the electromagnetic structure;

generating property estimation grids for the preselected material properties and analyzing the grids and curves to define a measurement strategy;

optimizing operating point properties and winding geometry and configuration;

with the electromagnetic structure, sensing electromagnetic responses at each operating point; and converting electromagnetic responses into estimates of the preselected material properties.

2. A method as claimed in claim 1 where property estimate tolerances are also estimated as a function of values of the estimated preselected properties over the defined dynamic range.

3. A method as claimed in claim 1 where operating point response curves are also generated for operating point properties.

* * * * *

UNITED STATES PATENT AND TRADEMARK OFFICE
CERTIFICATE OF CORRECTION

PATENT NO. : 6,433,542 B2  Page 1 of 1
DATED : August 13, 2002
INVENTOR(S) : Neil J. Goldfine and James R. Melcher It is certified that error appears in the above-identified patent and that said Letters Patent is hereby corrected as shown below:

<u>Column 58,</u>
Line 22, change "to" to -- of --.
Line 28, delete "and curves".
Line 30, after "properties" insert -- of operating points --.

Signed and Sealed this

Twelfth Day of November, 2002

Attest:

Attesting Officer

JAMES E. ROGAN
*Director of the United States Patent and Trademark Office*